US011957763B2

(12) United States Patent
Van Berkel et al.

(10) Patent No.: US 11,957,763 B2
(45) Date of Patent: *Apr. 16, 2024

(54) SULFAMIDE LINKERS FOR USE IN BIOCONJUGATES

(71) Applicant: SYNAFFIX B.V., Oss (NL)

(72) Inventors: Sander Sebastiaan Van Berkel, Wijchen (NL); Ryan Heesbeen, Nijmegen (NL); Jorge Merijn Mathieu Verkade, Eindhoven (NL); Maria Antonia Wijdeven, Lent (NL); Floris Louis Van Delft, Nijmegen (NL)

(73) Assignee: SYNAFFIX B.V., Oss (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/135,703

(22) Filed: Dec. 28, 2020

(65) Prior Publication Data

US 2021/0353766 A1 Nov. 18, 2021

Related U.S. Application Data

(63) Continuation of application No. 16/076,310, filed as application No. PCT/EP2017/052719 on Feb. 8, 2017, now Pat. No. 10,874,746.

(30) Foreign Application Priority Data

Feb. 8, 2016 (EP) ..................................... 16154739

(51) Int. Cl.
| | | |
|---|---|---|
| *C07K 14/00* | (2006.01) | |
| *A61K 47/68* | (2017.01) | |
| *C07K 14/435* | (2006.01) | |
| *C07K 16/32* | (2006.01) | |

(52) U.S. Cl.
CPC ...... *A61K 47/6889* (2017.08); *A61K 47/6803* (2017.08); *A61K 47/6855* (2017.08); *C07K 14/00* (2013.01); *C07K 14/435* (2013.01); *C07K 16/32* (2013.01)

(58) Field of Classification Search
None
See application file for complete search history.

(56) References Cited

U.S. PATENT DOCUMENTS

| | | | |
|---|---|---|---|
| 5,602,119 | A | 2/1997 | Vazquez et al. |
| 8,207,303 | B2 | 6/2012 | Cardarelli et al. |
| 2005/0256030 | A1 | 11/2005 | Feng |
| 2005/0276812 | A1 | 12/2005 | Ebens, Jr. et al. |
| 2007/0190597 | A1 | 8/2007 | Agnew et al. |
| 2009/0047248 | A1 | 2/2009 | Sun et al. |
| 2010/0260709 | A1 | 10/2010 | Brandl et al. |
| 2017/0029490 | A1 | 2/2017 | Winters et al. |

FOREIGN PATENT DOCUMENTS

| | | |
|---|---|---|
| CN | 104623687 A | 5/2015 |
| EP | 2 481 725 A1 | 8/2012 |
| WO | WO-01/88535 A1 | 11/2001 |
| WO | WO-03/082842 A1 | 10/2003 |
| WO | WO-2006/000085 A1 | 1/2006 |
| WO | WO-2008/060927 A2 | 5/2008 |
| WO | WO-2008/070291 A2 | 6/2008 |
| WO | WO-2009/067108 A1 | 5/2009 |
| WO | WO-2011/136645 A1 | 11/2011 |
| WO | WO-2014/065661 A1 | 5/2014 |
| WO | WO-2014/100762 A1 | 6/2014 |
| WO | WO-2014/177771 A1 | 11/2014 |
| WO | WO-2015/057063 A1 | 4/2015 |
| WO | WO-2015/057064 A1 | 4/2015 |

(Continued)

OTHER PUBLICATIONS

Babic et al., "Synthesis of 1-C-linked diphosphate analogues of UDP-N-Ac-glucosamine and UDP-N-Ac-muramic acid", Tetrahedron, vol. 64, No. 38, pp. 9093-9100, 2008 (8 pages).
Beerli et al., "Sortase Enzyme-Mediated Generation of Site-Specifically Conjugated Antibody Drug Conjugates with High In Vitro and In Vivo Potency", Public Library of Science, vol. 10, No. 7, 2015 (17 pages).
Erickson, et al., "The Effect of Different Linkers on Target Cell Catabolismand Pharmacokinetics/Pharmacodynamics of Trastuzumab Maytansinoid Conjugages", Molecular Cancer Therapeutics 11(5): 1133-1142 (2012).

(Continued)

*Primary Examiner* — Samantha L Shterengarts
(74) *Attorney, Agent, or Firm* — Sunit Talapatra; Foley & Lardner LLP

(57) ABSTRACT

The invention relates to a novel linker for use in bioconjugates such as antibody-drug-conjugates. The linker according to the invention is represented by formula:

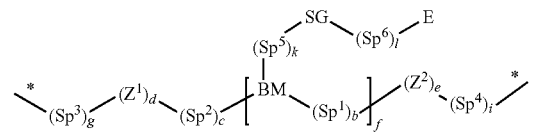

wherein:
BM is a branching moiety;
E is a capping group;
SG is a sulfamide group;
b, c, d, e, g, i, k, l are independently 0 or 1;
f is an integer in the range of 1 to 10;
$Sp^1$, $Sp^2$, $Sp^3$, $Sp^4$, $Sp^5$ and $Sp^6$ are a spacer moieties;
$Z^1$ and $Z^2$ are connecting groups.
The linker according to the invention is useful in the preparation of linker-conjugates and bioconjugates, and can be used for (a) improving conjugation efficiency in the preparation of the bioconjugate, (b) reducing aggregation during the preparation of the bioconjugate and/or of the bioconjugate, (c) increasing stability of the bioconjugate, and/or (d) increasing therapeutic index of the bioconjugate.

20 Claims, 5 Drawing Sheets

Specification includes a Sequence Listing.

(56) References Cited

FOREIGN PATENT DOCUMENTS

| WO | WO-2015/057065 A1 | 4/2015 |
|----|-------------------|--------|
| WO | WO-2015/057066 A1 | 4/2015 |
| WO | WO-2015/095952 A1 | 7/2015 |
| WO | WO-2015/095953 A1 | 7/2015 |
| WO | WO-2016/022027 A1 | 4/2016 |
| WO | WO-2016/053107 A1 | 4/2016 |
| WO | WO-2016/170186 A1 | 10/2016 |

OTHER PUBLICATIONS

International Search Report and Written Opinion of the International Searching Authority for PCT/EP2017/052719 dated Jun. 7, 2017 (14 pages).

International Search Report and Written Opinion of the International Searching Authority for PCT/EP2017/052788 dated May 12, 2017 (13 pages).

International Search Report and Written Opinion of the International Searching Authority for PCT/EP2017/052790 dated Jun. 27, 2017 (16 pages).

International Search Report and Written Opinion of the International Searching Authority for PCT/EP2017/052791 dated May 29, 2017 (13 pages).

Jeffrey et al., "Development and Properties of ß-Glucuronide Linkers for Monoclonal Antibody-Drug Conjugates", Bioconjugate Chemistry, vol. 17, No. 3, pp. 831-840, 2006 (10 pages).

Krueger et al., "Inhibitors of HCV NS5B polymerase: Synthesis and structure-activity relationships of N-alkyl-4-hydroxyquinolon-3-yl-benzothiadiazine sulfamides", Bioorganic & Medicinal Chemistry Letters, vol. 16, No. 13, pp. 3367-3370, 2006 (4 pages).

Lhospice et al., "Site-Specific Conjugation of Monomethyl Auristatin E to Anti-CD30 Antibodies Improves Their Pharmacokinetics and Therapeutic Index in Rodent Models", Molecular Pharmaceutics, vol. 12, pp. 1863-1871, 2015 (9 pages).

Li et al., "An anti-HER2 antibody conjugated with monomethyl auristatin E is highly effective in HER2-positive human gastric cancer", Cancer Biology & Therapy, vol. 17, No. 4, pp. 346-354, 2016 (10 pages).

Lu et al., "Designed Semisynthetic Protein Inhibiotrs of Ub/Ubl E1 Activating Enzymes", J. Am. Chem. Soc. 2010, 132, 1747-1749.

Lyon et al., "Self-hydrolyzing maleimides improve the stability and pharmacological properties of antibody-drug conjugates", Nature Biotechnology, vol. 32, No. 10, Oct. 2014, pp. 1059-1064 (7 pages).

Melagraki et al., "Identification of a series of novel derivatives as potent HCV inhibitors by a ligand-based virtual screening optimized procedure", Bioorganic & Medicinal Chemistry, vol. 15, 2007, pp. 7237-7247 (11 pages).

Murphy-Benenato et al., "Discovery of Efficacious Pseudomonas aeruginosa-Targeted Siderophore-Conjugated Monocarbams by Application of a Semi-mechanistic Pharmacokinetic/Pharmacodynamic Model", Journal of Medicinal Chemistry, vol. 58, pp. 2195-2205, 2015 (11 pages).

Phillips et al., "Targeting HER2-Positive Breast Cancer with Trastuzumab-DM1, an Antibody-Cytotoxic Drug Conjugate", Cancer Research, vol. 68, pp. 9280-9290, 2008 (12 pages).

Pillow et al., "Site-Specific Trastuzumab Maytansinoid Antibody-Drug Conjugates with Improved Therapeutic Activity through Linker and Antibody Engineering", Journal of Medicinal Chemistry, vol. 57, pp. 7890-7899, 2014 (10 pages).

Senter et al., "Self-hydrolyzing maleimides improve the stability and pharmacological properties of antibody-drug conjugates", Nature Biotechnology, 2014, 32(10) (7 pages).

Somu et al., "Antitubercular Nucleosides That Inhibit Siderophore Biosynthesis: SAR of the Glycosyl Domain", Journal of Medicinal Chemistry, vol. 49, No. 26, 2006, pp. 7623-7635 (13 pages).

Van Geel et al., "Chemoenzymatic Conjugation of Toxic Payloads to the Globally Conserved N-Glycan of Native mAbs Provides Homogeneous and Highly Efficacious Antibody-Drug Conjugates", Bioconjugate Chemistry, vol. 26, pp. 2233-2242, 2015 (10 pages).

Yao et al., "A novel humanized anti-HER2 antibody conjugated with MMAE exerts potent anti-tumor activity", Breast Cancer Res Treat, vol. 153, pp. 123-133, 2015 (11 pages).

"Seattle Genetics' Antibody-Drug Conjugate Receives FDA Okay to Treat Lymphomas", Genetic Engineering & Biotechnology News, downloaded from https://www.genengnews.com/topics/drug-discovery/seattle-genetics-antibody-drug-conjugate-receives-fda-okay-to-treat-lymphomas/ on Nov. 18, 2021 (Year: 2011), (3 pages).

Horwitz et al., "MDX-060 Monoclonal Antibody in Treating Patients With Refractory or Relapsed Lymphoma", US National Library of Medicine, downloaded from https://clinicaltrials.gov/ct2/show/NCT00059995?term= iratumumab&draw=2&rank=1 on Nov. 18, 2021 (Year: 2003), (9 pages).

BOI = biomolecule of interest
D = MOI = molecule of interest (or target molecule)
$F_1$ = native or engineered functional group
$Q_1$ = reactive group specific for $F_1$
n = 1,2,3...

BOI =   peptide/protein   or   glycan   or   nucleic acid

11a $R^1$ = OH; $R^2$ = $(CH_2)_2SH$
11b $R^1$ = OH; $R^2$ = $CH_2N_3$
11c $R^1$ = OH; $R^2$ = $CF_2N_3$
11d $R^1$ = $N_3$; $R^2$ = $CH_3$

SEQUENCE LISTING

<160> NUMBER OF SEQ ID NOS: 2

<210> SEQ ID NO 1
<211> LENGTH: 1258
<212> TYPE: PRT
<213> ORGANISM: Artificial sequence
<220> FEATURE:
<223> OTHER INFORMATION: Fusion protein EndoSH

<400> SEQUENCE: 1

```
Met Pro Ser Ile Asp Ser Leu His Tyr Leu Ser Glu Asn Ser Lys Lys
1               5                   10                  15

Glu Phe Lys Glu Glu Leu Ser Lys Ala Gly Gln Glu Ser Gln Lys Val
            20                  25                  30

Lys Glu Ile Leu Ala Lys Ala Gln Gln Ala Asp Lys Gln Ala Gln Glu
        35                  40                  45

Leu Ala Lys Met Lys Ile Pro Glu Lys Ile Pro Met Lys Pro Leu His
    50                  55                  60

Gly Pro Leu Tyr Gly Gly Tyr Phe Arg Thr Trp His Asp Lys Thr Ser
65                  70                  75                  80

Asp Pro Thr Glu Lys Asp Lys Val Asn Ser Met Gly Glu Leu Pro Lys
                85                  90                  95

Glu Val Asp Leu Ala Phe Ile Phe His Asp Trp Thr Lys Asp Tyr Ser
            100                 105                 110

Leu Phe Trp Lys Glu Leu Ala Thr Lys His Val Pro Lys Leu Asn Lys
        115                 120                 125

Gln Gly Thr Arg Val Ile Arg Thr Ile Pro Trp Arg Phe Leu Ala Gly
    130                 135                 140

Gly Asp Asn Ser Gly Ile Ala Glu Asp Thr Ser Lys Tyr Pro Asn Thr
145                 150                 155                 160

Pro Glu Gly Asn Lys Ala Leu Ala Lys Ala Ile Val Asp Glu Tyr Val
                165                 170                 175

Tyr Lys Tyr Asn Leu Asp Gly Leu Asp Val Asp Val Glu His Asp Ser
            180                 185                 190

Ile Pro Lys Val Asp Lys Lys Glu Asp Thr Ala Gly Val Glu Arg Ser
        195                 200                 205

Ile Gln Val Phe Glu Glu Ile Gly Lys Leu Ile Gly Pro Lys Gly Val
    210                 215                 220

Asp Lys Ser Arg Leu Phe Ile Met Asp Ser Thr Tyr Met Ala Asp Lys
225                 230                 235                 240

Asn Pro Leu Ile Glu Arg Gly Ala Pro Tyr Ile Asn Leu Leu Leu Val
                245                 250                 255
```

Gln Val Tyr Gly Ser Gln Gly Glu Lys Gly Trp Glu Pro Val Ser
            260                 265                 270

Asn Arg Pro Glu Lys Thr Met Glu Arg Trp Gln Gly Tyr Ser Lys
        275                 280                 285

Tyr Ile Arg Pro Glu Gln Tyr Met Ile Gly Phe Ser Phe Tyr Glu Glu
    290                 295                 300

Asn Ala Gln Glu Gly Asn Leu Trp Tyr Asp Ile Asn Ser Arg Lys Asp
305                 310                 315                 320

Glu Asp Lys Ala Asn Gly Ile Asn Thr Asp Ile Thr Gly Thr Arg Ala
                325                 330                 335

Glu Arg Tyr Ala Arg Trp Gln Pro Lys Thr Gly Gly Val Lys Gly Gly
            340                 345                 350

Ile Phe Ser Tyr Ala Ile Asp Arg Asp Gly Val Ala His Gln Pro Lys
        355                 360                 365

Lys Tyr Ala Lys Gln Lys Glu Phe Lys Asp Ala Thr Asp Asn Ile Phe
    370                 375                 380

His Ser Asp Tyr Ser Val Ser Lys Ala Leu Lys Thr Val Met Leu Lys
385                 390                 395                 400

Asp Lys Ser Tyr Asp Leu Ile Asp Glu Lys Asp Phe Pro Asp Lys Ala
                405                 410                 415

Leu Arg Glu Ala Val Met Ala Gln Val Gly Thr Arg Lys Gly Asp Leu
            420                 425                 430

Glu Arg Phe Asn Gly Thr Leu Arg Leu Asp Asn Pro Ala Ile Gln Ser
        435                 440                 445

Leu Glu Gly Leu Asn Lys Phe Lys Lys Leu Ala Gln Leu Asp Leu Ile
    450                 455                 460

Gly Leu Ser Arg Ile Thr Lys Leu Asp Arg Ser Val Leu Pro Ala Asn
465                 470                 475                 480

Met Lys Pro Gly Lys Asp Thr Leu Glu Thr Val Leu Glu Thr Tyr Lys
                485                 490                 495

Lys Asp Asn Lys Glu Glu Pro Ala Thr Ile Pro Pro Val Ser Leu Lys
            500                 505                 510

Val Ser Gly Leu Thr Gly Leu Lys Glu Leu Asp Leu Ser Gly Phe Asp
        515                 520                 525

Arg Glu Thr Leu Ala Gly Leu Asp Ala Ala Thr Leu Thr Ser Leu Glu
    530                 535                 540

Lys Val Asp Ile Ser Gly Asn Lys Leu Asp Leu Ala Pro Gly Thr Glu
545                 550                 555                 560

Asn Arg Gln Ile Phe Asp Thr Met Leu Ser Thr Ile Ser Asn His Val
                565                 570                 575

Gly Ser Asn Glu Gln Thr Val Lys Phe Asp Lys Gln Lys Pro Thr Gly
            580                 585                 590

His Tyr Pro Asp Thr Tyr Gly Lys Thr Ser Leu Arg Leu Pro Val Ala
        595                 600                 605

Asn Glu Lys Val Asp Leu Gln Ser Gln Leu Leu Phe Gly Thr Val Thr
    610                 615                 620

Asn Gln Gly Thr Leu Ile Asn Ser Glu Ala Asp Tyr Lys Ala Tyr Gln
625                 630                 635                 640

Asn His Lys Ile Ala Gly Arg Ser Phe Val Asp Ser Asn Tyr His Tyr
                645                 650                 655

Asn Asn Phe Lys Val Ser Tyr Glu Asn Tyr Thr Val Lys Val Thr Asp
            660                 665                 670

Ser Thr Leu Gly Thr Thr Thr Asp Lys Thr Leu Ala Thr Asp Lys Glu

-continued

```
                675                 680                 685
Glu Thr Tyr Lys Val Asp Phe Phe Ser Pro Ala Asp Lys Thr Lys Ala
690                 695                 700
Val His Thr Ala Lys Val Ile Val Gly Asp Glu Lys Thr Met Met Val
705                 710                 715                 720
Asn Leu Ala Glu Gly Ala Thr Val Ile Gly Gly Ser Ala Asp Pro Val
                725                 730                 735
Asn Ala Arg Lys Val Phe Asp Gly Gln Leu Gly Ser Glu Thr Asp Asn
                740                 745                 750
Ile Ser Leu Gly Trp Asp Ser Lys Gln Ser Ile Ile Phe Lys Leu Lys
                755                 760                 765
Glu Asp Gly Leu Ile Lys His Trp Arg Phe Phe Asn Asp Ser Ala Arg
770                 775                 780
Asn Pro Glu Thr Thr Asn Lys Pro Ile Gln Ala Ser Leu Gln Ile
785                 790                 795                 800
Phe Asn Ile Lys Asp Tyr Asn Leu Asp Asn Leu Leu Glu Asn Pro Asn
                805                 810                 815
Lys Phe Asp Asp Glu Lys Tyr Trp Ile Thr Val Asp Thr Tyr Ser Ala
                820                 825                 830
Gln Gly Glu Arg Ala Thr Ala Phe Ser Asn Thr Leu Asn Asn Ile Thr
                835                 840                 845
Ser Lys Tyr Trp Arg Val Val Phe Asp Thr Lys Gly Asp Arg Tyr Ser
850                 855                 860
Ser Pro Val Val Pro Glu Leu Gln Ile Leu Gly Tyr Pro Leu Pro Asn
865                 870                 875                 880
Ala Asp Thr Ile Met Lys Thr Val Thr Thr Ala Lys Glu Leu Ser Gln
                885                 890                 895
Gln Lys Asp Lys Phe Ser Gln Lys Met Leu Asp Glu Leu Lys Ile Lys
                900                 905                 910
Glu Met Ala Leu Glu Thr Ser Leu Asn Ser Lys Ile Phe Asp Val Thr
                915                 920                 925
Ala Ile Asn Ala Asn Ala Gly Val Leu Lys Asp Cys Ile Glu Lys Arg
930                 935                 940
Gln Leu Leu Lys Lys Gly Gly Gly Ser Gly Gly Gly Gly Ser Gly
945                 950                 955                 960
Gly Gly Gly Ser His His His His His Glu Phe Gly Gly Gly
                965                 970                 975
Ser Gly Gly Gly Gly Ser Gly Gly Gly Ser Ala Pro Ala Pro Val
                980                 985                 990
Lys Gln Gly Pro Thr Ser Val Ala Tyr Val Glu Val Asn Asn Ser
                995                 1000                1005
Met Leu Asn Val Gly Lys Tyr Thr Leu Ala Asp Gly Gly Gly Asn
                1010                1015                1020
Ala Phe Asp Val Ala Val Ile Phe Ala Ala Asn Ile Asn Tyr Asp
                1025                1030                1035
Thr Gly Thr Lys Thr Ala Tyr Leu His Phe Asn Glu Asn Val Gln
                1040                1045                1050
Arg Val Leu Asp Asn Ala Val Thr Gln Ile Arg Pro Leu Gln Gln
                1055                1060                1065
Gln Gly Ile Lys Val Leu Leu Ser Val Leu Gly Asn His Gln Gly
                1070                1075                1080
Ala Gly Phe Ala Asn Phe Pro Ser Gln Gln Ala Ala Ser Ala Phe
                1085                1090                1095
```

```
Ala Lys Gln Leu Ser Asp Ala Val Ala Lys Tyr Gly Leu Asp Gly
    1100            1105                1110

Val Asp Phe Asp Asp Glu Tyr Ala Glu Tyr Gly Asn Asn Gly Thr
    1115            1120                1125

Ala Gln Pro Asn Asp Ser Ser Phe Val His Leu Val Thr Ala Leu
    1130            1135                1140

Arg Ala Asn Met Pro Asp Lys Ile Ile Ser Leu Tyr Asn Ile Gly
    1145            1150                1155

Pro Ala Ala Ser Arg Leu Ser Tyr Gly Gly Val Asp Val Ser Asp
    1160            1165                1170

Lys Phe Asp Tyr Ala Trp Asn Pro Tyr Tyr Gly Thr Trp Gln Val
    1175            1180                1185

Pro Gly Ile Ala Leu Pro Lys Ala Gln Leu Ser Pro Ala Ala Val
    1190            1195                1200

Glu Ile Gly Arg Thr Ser Arg Ser Thr Val Ala Asp Leu Ala Arg
    1205            1210                1215

Arg Thr Val Asp Glu Gly Tyr Gly Val Tyr Leu Thr Tyr Asn Leu
    1220            1225                1230

Asp Gly Gly Asp Arg Thr Ala Asp Val Ser Ala Phe Thr Arg Glu
    1235            1240                1245

Leu Tyr Gly Ser Glu Ala Val Arg Thr Pro
    1250            1255

<210> SEQ ID NO 2
<211> LENGTH: 410
<212> TYPE: PRT
<213> ORGANISM: Artificial sequence
<220> FEATURE:
<223> OTHER INFORMATION: His-TnGalNAcT(33-421)

<400> SEQUENCE: 2

Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
                20                  25                  30

Tyr Asn Ala Thr Gln Pro Thr Leu Arg Asn Val Glu Arg Leu Ala Ala
            35                  40                  45

Asn Trp Pro Lys Lys Ile Pro Ser Asn Tyr Ile Glu Asp Ser Glu Glu
        50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
        115                 120                 125

Thr Glu Asp Gly Val Lys Lys Ala Glu Ala Val Thr Leu Pro Leu
    130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190
```

```
Ile Ile Val Pro Tyr Arg Asp Arg Gln Gln His Leu Ala Ile Phe Leu
        195             200             205
Asn His Met His Pro Phe Leu Met Lys Gln Gln Ile Glu Tyr Gly Ile
    210             215             220
Phe Ile Val Glu Gln Glu Gly Asn Lys Asp Phe Asn Arg Ala Lys Leu
225             230             235             240
Met Asn Val Gly Phe Val Glu Ser Gln Lys Leu Val Ala Glu Gly Trp
            245             250             255
Gln Cys Phe Val Phe His Asp Ile Asp Leu Leu Pro Leu Asp Thr Arg
            260             265             270
Asn Leu Tyr Ser Cys Pro Arg Gln Pro Arg His Met Ser Ala Ser Ile
        275             280             285
Asp Lys Leu His Phe Lys Leu Pro Tyr Glu Asp Ile Phe Gly Gly Val
    290             295             300
Ser Ala Met Thr Leu Glu Gln Phe Thr Arg Val Asn Gly Phe Ser Asn
305             310             315             320
Lys Tyr Trp Gly Trp Gly Gly Glu Asp Asp Asp Met Ser Tyr Arg Leu
            325             330             335
Lys Lys Ile Asn Tyr His Ile Ala Arg Tyr Lys Met Ser Ile Ala Arg
            340             345             350
Tyr Ala Met Leu Asp His Lys Lys Ser Thr Pro Asn Pro Lys Arg Tyr
            355             360             365
Gln Leu Leu Ser Gln Thr Ser Lys Thr Phe Gln Lys Asp Gly Leu Ser
    370             375             380
Thr Leu Glu Tyr Glu Leu Val Gln Val Val Gln Tyr His Leu Tyr Thr
385             390             395             400
His Ile Leu Val Asn Ile Asp Glu Arg Ser
            405             410
```

SULFAMIDE LINKERS FOR USE IN BIOCONJUGATES

CROSS-REFERENCE TO RELATED APPLICATIONS

This application is a continuation of U.S. application Ser. No. 16/076,310, filed Aug. 7, 2018, which is a U.S. national stage application of PCT/EP2017/052719, filed Feb. 8, 2017, which claims the benefit of and priority to European Patent Application No. 16154739.3, filed Feb. 8, 2016, the entire contents of which are incorporated herein by reference.

SEQUENCE LISTING

The instant application contains a Sequence Listing which has been submitted in ASCII format via EFS-WEB and is hereby incorporated by reference in its entirety. Said ASCII copy, created on Aug. 7, 2018, is named 069818-4060_2018-08-07_Sequence_Listing.txt and is 29 KB.

FIELD OF THE INVENTION

The present invention is in the field of bioconjugation. The invention relates to novel sulfamide linkers and conjugates thereof, and to methods for the preparation thereof. More particularly, the invention relates to linkers comprising an acylsulfamide group and/or a carbamoyl sulfamide group and to conjugates comprising said linkers. The invention further relates to a process for the preparation of bioconjugates comprising a linker, the linker comprising an acylsulfamide group and/or a carbamoyl sulfamide group.

BACKGROUND

Bioconjugation is the process of linking two or more molecules, of which at least one is a biomolecule. The biomolecule(s) may also be referred to as "biomolecule(s) of interest", the other molecule(s) may also be referred to as "target molecule" or "molecule of interest". Typically the biomolecule of interest (BOI) will consist of a protein (or peptide), a glycan, a nucleic acid (or oligonucleotide), a lipid, a hormone or a natural drug (or fragments or combinations thereof). The other molecule of interest (MOI) may also be a biomolecule, hence leading to the formation of homo- or heterodimers (or higher oligomers), or the other molecule may possess specific features that are imparted onto the biomolecule of interest by the conjugation process. For example, the modulation of protein structure and function by covalent modification with a chemical probe for detection and/or isolation has evolved as a powerful tool in proteome-based research and biomedical applications. Fluorescent or affinity tagging of proteins is key to studying the trafficking of proteins in their native habitat. Vaccines based on protein-carbohydrate conjugates have gained prominence in the fight against HIV, cancer, malaria and pathogenic bacteria, whereas carbohydrates immobilized on microarrays are instrumental in elucidation of the glycome. Synthetic DNA and RNA oligonucleotides (ONs) require the introduction of a suitable functionality for diagnostic and therapeutic applications, such as microarray technology, antisense and gene-silencing therapies, nanotechnology and various materials sciences applications. For example, attachment of a cell-penetrating ligand is the most commonly applied strategy to tackle the low internalization rate of ONs encountered during oligonucleotide-based therapeutics (antisense, siRNA). Similarly, the preparation of oligonucleotide-based microarrays requires the selective immobilization of ONs on a suitable solid surface, e.g. glass.

There are numerous examples of chemical reactions suitable to covalently link two (or more) molecular structures. However, labelling of biomolecules poses high restrictions on the reaction conditions that can be applied (solvent, concentration, temperature), while the desire of chemoselective labelling limits the choice of reactive groups. For obvious reasons, biological systems generally flourish best in an aqueous environment meaning that reagents for bioconjugation should be suitable for application in aqueous systems. In general, two strategic concepts can be recognized in the field of bioconjugation technology: (a) conjugation based on a functional group already present in the biomolecule of interest, such as for example a thiol, an amine, an alcohol or a hydroxyphenol unit or (b) a two-stage process involving engineering of one (or more) unique reactive groups into a BOI prior to the actual conjugation process.

The first approach typically involves a reactive amino acid side-chain in a protein (e.g. cysteine, lysine, serine and tyrosine), or a functional group in a glycan (e.g. amine, aldehyde) or nucleic acid (e.g. purine or pyrimidine functionality or alcohol). As summarized inter alia in G. T. Hermanson, "*Bioconjugate Techniques*", Elsevier, $3^{rd}$ Ed. 2013, incorporated by reference, a large number of reactive functional groups have become available over the years for chemoselective targeting of one of these functional groups, such as maleimide, haloacetamide, activated ester, activated carbonate, sulfonyl halide, activated thiol derivative, alkene, alkyne, allenamide and more, each of which requiring its own specific conditions for conjugation (pH, concentration, stoichiometry, light, etc.). Most prominently, cysteine-maleimide conjugation stands out for protein conjugation by virtue of its high reaction rate and chemoselectivity. However, when no cysteine is available for conjugation, as in many proteins and certainly in other biomolecules, other methods are often required, each suffering from its own shortcomings.

An elegant and broadly applicable solution for bioconjugation involves the two-stage approach. Although more laborious, two-stage conjugation via engineered functionality typically leads to higher selectivity (site-specificity) than conjugation on a natural functionality. Besides that, full stability can be achieved by proper choice of construct, which can be an important shortcoming of one stage conjugation on native functionality, in particular for cysteine-maleimide conjugation. Typical examples of a functional group that may be imparted onto the BOI include (strained) alkyne, (strained) alkene, norbornene, tetrazine, azide, phosphine, nitrile oxide, nitrone, nitrile imine, diazo compound, carbonyl compound, (O-alkyl)hydroxylamine and hydrazine, which may be achieved by either chemical or molecular biology approach. Each of the above functional groups is known to have at least one reaction partner, in many cases involving complete mutual reactivity. For example, cyclooctynes react selectively and exclusively with 1,3-dipoles, strained alkenes with tetrazines and phosphines with azides, leading to fully stable covalent bonds. However, some of the above functional groups have the disadvantage of being highly lipophilic, which may compromise conjugation efficiency, in particular in combination with a lipophilic molecule of interest (see below).

The final linking unit between the biomolecule and the other molecule of interest should preferentially also be fully compatible with an aqueous environment in terms of solubility, stability and biocompatibility. For example, a highly lipophilic linker may lead to aggregation (during and/or after conjugation), which may significantly increase reaction times and/or reduce conjugation yields, in particular when the MOI is also of hydrophobic nature. Similarly, highly lipophilic linker-MOI combination may lead to unspecific binding to surfaces or specific hydrophobic patches on the same or other biomolecules. If the linker is susceptible to aqueous hydrolysis or other water-induced cleavage reactions, the components comprising the original bioconjugate separate by diffusion. For example, certain ester moieties are not suitable due to saponification while p-hydroxycarbonyl or γ-dicarbonyl compounds could lead to retro-aldol or retro-Michael reaction, respectively. Finally, the linker should be inert to functionalities present in the bioconjugate or any other functionality that may be encountered during application of the bioconjugate, which excludes, amongst others, the use of linkers featuring for example a ketone or aldehyde moiety (may lead to imine formation), an α,β-unsaturated carbonyl compound (Michael addition), thio-esters or other activated esters (amide bond formation).

Compounds made of linear oligomers of ethylene glycol, so-called polyethylene glycol (PEG) linkers, enjoy particular popularity nowadays in biomolecular conjugation processes. PEG linkers are highly water soluble, non-toxic, non-antigenic, and lead to negligible or no aggregation. For this reason, a large variety of linear, bifunctional PEG linkers are commercially available from various sources, which can be selectively modified at either end with a (bio)molecule of interest. PEG linkers are the product of a polymerization process of ethylene oxide and are therefore typically obtained as stochastic mixtures of chain length, which can be partly resolved into PEG constructs with an average weight distribution centered around 1, 2, 4 kDa or more (up to 60 kDa). Homogeneous, discrete PEGs (dPEGs) are also known with molecular weights up to 4 kDa and branched versions thereof go up to 15 kDa. Interestingly, the PEG unit itself imparts particular characteristics onto a biomolecule. In particular, protein PEGylation may lead to prolonged residence in vivo, decreased degradation by metabolic enzymes and a reduction or elimination of protein immunogenicity. Several PEGylated proteins have been FDA-approved and are currently on the market.

By virtue of their polarity, PEG linkers are suitable for bioconjugation of small and/or water-soluble moieties under aqueous conditions. However, in case of conjugation of hydrophobic, water-insoluble molecules of interest, the polarity of a PEG unit may be insufficient to offset hydrophobicity, leading to significantly reduced reaction rates, lower yields and induced aggregation issues. In such case, lengthy PEG linkers and/or significant amounts of organic co-solvents may be required to solubilize the reagents. For example, in the field of antibody-drug conjugates, the controlled attachment of a distinct number of toxic payloads to a monoclonal antibody is key, with a payload typically selected from the group of auristatins, maytansinoids, duocarmycins, enediynes or pyrrolobenzodiazepines (PBDs), with many others are underway. With the exception of auristatin F, all toxic payloads are poorly soluble or water-insoluble, which necessitates organic co-solvents to achieve successful conjugation, such as 25% N,N-dimethylacetamide (DMA) or dimethylformamide (DMF) or up to 50% propylene glycol (PG). In case of hydrophobic payloads, despite the use of aforementioned co-solvents, large stoichiometries of reagents may be required during conjugation while efficiency and yield may be significantly compromised due to aggregation (in process or after product isolation), as for example described by Senter et al. in *Nat. Biotechn.* 2014, 24, 1256-1263, incorporated by reference. The use of long PEG spacers (12 units or more) may partially enhance solubility and/or conjugation efficiency, but it has been shown that long PEG spacers may lead to more rapid in vivo clearance, and hence negatively influence the pharmacokinetic profile of the ADC.

Using conventional linkers (e.g. PEG), effective conjugation is often hampered by the relatively low solubility of the linker-conjugate in aqueous media, especially when a relative water-insoluble or hydrophobic target molecule is used. In their quest for a short, polar spacer that enables fast and efficient conjugation of hydrophobic moieties, the inventors have developed the sulfamide linker, which was found to improve the solubility of the linker-conjugate, which in turn significantly improves the efficiency of the conjugation and reduces both in process and product aggregation. This is disclosed in patent application PCT/NL2015/050697 (WO 2016/053107), which is incorporated herein in its entirety.

Further linkers are known in the art, and disclosed in e.g. WO 2008/070291, incorporated by reference. WO 2008/070291 discloses a linker for the coupling of targeting agents to anchoring components. The linker contains hydrophilic regions represented by polyethylene glycol (PEG) and an extension lacking chiral centers that is coupled to a targeting agent.

WO 01/88535, incorporated by reference, discloses a linker system for surfaces for bioconjugation, in particular a linker system having a novel hydrophilic spacer group. The hydrophilic atoms or groups for use in the linker system are selected from the group consisting of O, NH, C=O (keto group), O—C=O (ester group) and $CR^3R^4$, wherein $R^3$ and $R^4$ are independently selected from the group consisting of H, OH, $C_1$-$C_4$ alkoxy and $C_1$-$C_4$ acyloxy.

WO 2014/100762, incorporated by reference, describes compounds with a hydrophilic self-immolative linker, which is cleavable under appropriate conditions and incorporates a hydrophilic group to provide better solubility of the compound. The compounds comprise a drug moiety, a targeting moiety capable of targeting a selected cell population, and a linker which contains an acyl unit, an optional spacer unit for providing distance between the drug moiety and the targeting moiety, a peptide linker which can be cleavable under appropriate conditions, a hydrophilic self-immolative linker, and an optional second self-immolative spacer or cyclization self-elimination linker. The hydrophilic self-immolative linker is e.g. a benzyloxycarbonyl group.

SUMMARY OF THE INVENTION

The present invention relates to an improved linker that can be used in the field of bioconjugation. The sulfamide linker that has been developed by the inventors has been put to practice in the following aspects of the invention.

In a first aspect, the invention concerns a linker-conjugate as defined herein, comprising the linker according to the invention, as well as the use of said linker-conjugate for preparing a bioconjugate according to the invention. In a second aspect, the invention concerns a linker-construct as defined herein, comprising the linker according to the invention, as well as the use of said linker-construct for preparing a linker-conjugate according to the invention and a process for preparing the linker-conjugate according to the invention using said linker-construct. In a third aspect, the invention concerns a bioconjugate as defined herein, comprising the linker according to the invention. In a fourth aspect, the invention concerns a process for preparing the bioconjugate according to the invention and the bioconjugate obtainable thereby. In a fifth aspect, the invention concerns the use of the linker according to the invention in bioconjugation for improving conjugation efficiency, reducing aggregation, increasing stability and increasing therapeutic index. In a sixth aspect, the invention concerns the medical use of the bioconjugate according to the invention, in particular for the treatment of cancer.

The linker-conjugate according to the invention as a compound wherein a target molecule D is covalently connected to a reactive group $Q^1$, via a linker, wherein the linker is represented by formula:

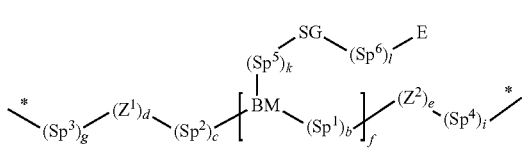

wherein:
BM is a branching moiety;
E is a capping group;
SG is a sulfamide group according to formula (1);
b is independently 0 or 1;
c is 0 or 1;
d is 0 or 1;
e is 0 or 1;
f is an integer in the range of 1 to 10;
g is 0 or 1;
i is 0 or 1;
k is 0 or 1;
l is 0 or 1;
$Sp^1$ is a spacer moiety;
$Sp^2$ is a spacer moiety;
$Sp^3$ is a spacer moiety;
$Sp^4$ is a spacer moiety;
$Sp^5$ is a spacer moiety;
$Sp^6$ is a spacer moiety;
$Z^1$ is a connecting group;
$Z^2$ is a connecting group,
wherein one of the bonds labelled with * is connected to reactive group $Q^1$ and one of the bonds labelled with * is connected to target molecule D, and wherein the sulfamide group SG is represented by formula (1):

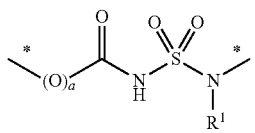

wherein
a is 0 or 1; and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups are optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a further target molecule D, wherein the target molecule is optionally connected to N via a spacer moiety,
and wherein one of the bonds labelled with * is connected to the branching moiety, optionally via spacer $Sp^5$, and the other bond labelled with * to a capping group E, optionally via spacer $Sp^6$.

The bioconjugate according to the invention is a compound wherein a target molecule D is covalently connected to a biomolecule B, via a linker, wherein the linker is represented by formula:

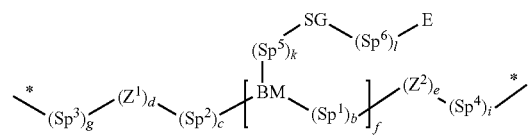

wherein:
BM is a branching moiety;
E is a capping group;
SG is a sulfamide group according to formula (1);
b is independently 0 or 1;
c is 0 or 1;
d is 0 or 1;
e is 0 or 1;
f is an integer in the range of 1 to 10;
g is 0 or 1;
i is 0 or 1;
k is 0 or 1;
l is 0 or 1;
$Sp^1$ is a spacer moiety;
$Sp^2$ is a spacer moiety;
$Sp^3$ is a spacer moiety;
$Sp^4$ is a spacer moiety;
$Sp^5$ is a spacer moiety;
$Sp^6$ is a spacer moiety;
$Z^1$ is a connecting group;
$Z^2$ is a connecting group,
wherein one of the bonds labelled with * is connected to biomolecule B and one of the bonds labelled with * is connected to target molecule D, and wherein the sulfamide group SG is represented by formula (1):

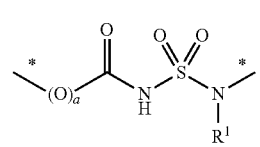

wherein
a is 0 or 1; and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups are optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a further target molecule D, wherein the target molecule is optionally connected to N via a spacer moiety, and wherein one of the bonds labelled with * is connected to the branching moiety, optionally via spacer $Sp^5$, and the other bond labelled with * to a capping group E, optionally via spacer $Sp^6$.

The invention further concerns a process for the preparation of a bioconjugate, comprising reacting a reactive group $Q^1$ of the compound according to any one of claims 1-6 with a functional group $F^1$ of a biomolecule (B).

The invention further concerns the use of the linker-conjugate according to the invention for the preparation of a bioconjugate.

The invention further concerns the use of a linker represented by formula:

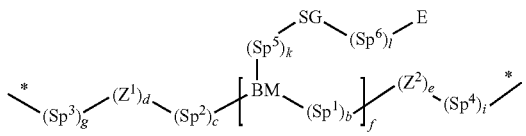

wherein:
BM is a branching moiety;
E is a capping group;
SG is a sulfamide group according to formula (1);
b is independently 0 or 1;
c is 0 or 1;
d is 0 or 1;
e is 0 or 1;
f is an integer in the range of 1 to 10;
g is 0 or 1;
i is 0 or 1;
k is 0 or 1;
l is 0 or 1;
$Sp^1$ is a spacer moiety;
$Sp^2$ is a spacer moiety;
$Sp^3$ is a spacer moiety;
$Sp^4$ is a spacer moiety;
$Sp^5$ is a spacer moiety;
$Sp^6$ is a spacer moiety;
$Z^1$ is a connecting group;
$Z^2$ is a connecting group,
wherein one of the bonds labelled with * is connected to biomolecule B and one of the bonds labelled with * is connected to target molecule D, and wherein the sulfamide group SG is represented by formula (1):

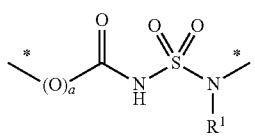

wherein
a is 0 or 1; and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups are optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a further target molecule D, wherein the target molecule is optionally connected to N via a spacer moiety, and wherein one of the bonds labelled with * is connected to the branching moiety, optionally via spacer $Sp^5$, and the other bond labelled with * to a capping group E, optionally via spacer $Sp^6$, in a bioconjugate for:
(a) improving conjugation efficiency in the preparation of the bioconjugate,
(b) reducing aggregation during the preparation of the bioconjugate and/or of the bioconjugate,
(c) increasing stability of the bioconjugate, and/or
(d) increasing therapeutic index of the bioconjugate.

The invention further concerns the bioconjugate according to the invention for use in the treatment of a subject in need thereof.

DETAILED DESCRIPTION

Figure 1:
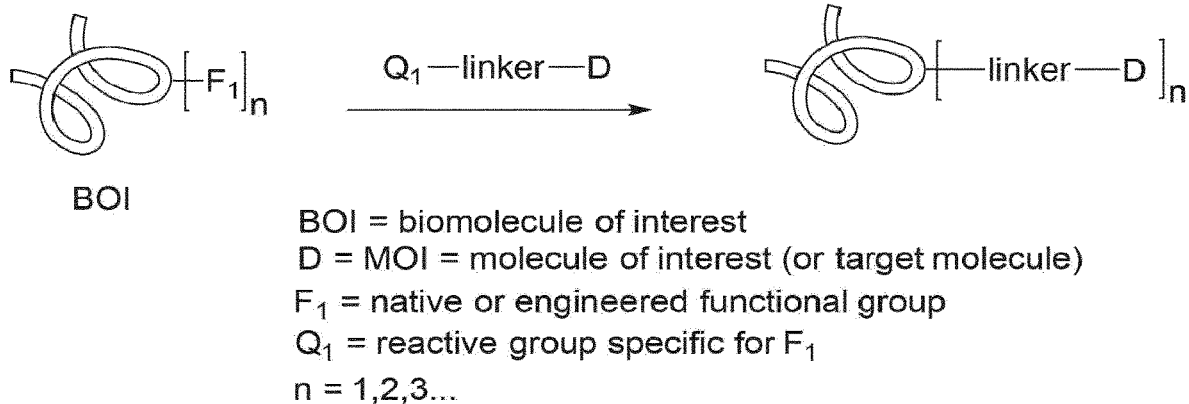
FIG. 1 describes the general concept of conjugation of biomolecules: a biomolecule of interest (BOI) containing one or more functional groups $F^1$ is incubated with (excess of) a target molecule D (also referred to as molecule of interest or MOI) covalently attached to a reactive group $Q^1$ via a specific linker. In the process of bioconjugation, a chemical reaction between $F^1$ and $Q^1$ takes place, thereby forming a bioconjugate comprising a covalent connection between the BOI and the MOI. The BOI may e.g. be a peptide/protein, a glycan or a nucleic acid.
Figure 1:
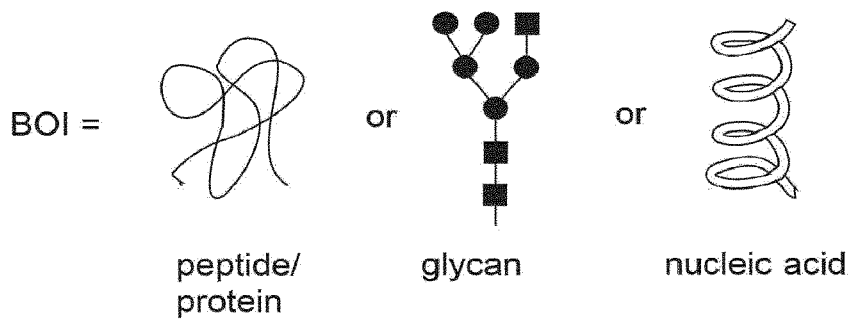

The present invention relates to an improved linker that can be used in the field of bioconjugation. The sulfamide linker that has been developed by the inventors has been put to practice in the following aspects of the invention.

In a first aspect, the invention concerns a linker-conjugate as defined herein, comprising the linker according to the invention, as well as the use of said linker-conjugate for preparing a bioconjugate according to the invention. In a second aspect, the invention concerns a linker-construct as defined herein, comprising the linker according to the invention, as well as the use of said linker-construct for preparing a linker-conjugate according to the invention and a process for preparing the linker-conjugate according to the invention using said linker-construct. In a third aspect, the invention concerns a bioconjugate as defined herein, comprising the linker according to the invention. In a fourth aspect, the invention concerns a process for preparing the bioconjugate according to the invention and the bioconjugate obtainable thereby. In a fifth aspect, the invention concerns the use of the linker according to the invention in bioconjugation for improving conjugation efficiency, reducing aggregation, increasing stability and increasing therapeutic index. In a sixth aspect, the invention concerns the medical use of the bioconjugate according to the invention, in particular for the treatment of cancer.

Key to all of the above aspects to the invention is the linker according to the invention, which comprises a branching moiety BM in the main chain of the linker and a sulfamide group SG in the side chain of the linker. Herein, "main chain" refers to the chain of atoms that connects target molecule D (or $Q^1$) with biomolecule B (or $Q^2$). The branching moiety is located in the main chain. The "side chain" refers to the chain of atoms that connects branching moiety BM to capping group E, also referred to as the "branch". The linker according to the invention is further defined below. The inventors surprisingly found that using a sulfamide group within the side chain (branch), in the configuration according to the present invention, provides many advantages when preparing and using bioconjugates such as antibody-drug-conjugates.

First and foremost, all the advantages associated with sulfamide groups embedded in the chain of a linker, i.e. biomolecule B or reactive group $Q^1$ is connected to one end of the sulfamide group and target molecule D or reactive group $Q^2$ is connected to the other end of the sulfamide group, also hold for the present configuration, wherein the sulfamide moiety is not located in the chain between target molecule and biomolecule, but located in a branch of the chain. The advantages in terms of conjugation efficiency and reduced aggregation are described in PCT/NL2015/020697, which is incorporated herein by reference in its entirety. Using conventional linkers (e.g. PEG), effective conjugation is often hampered by the relatively low solubility of the linker-conjugate in aqueous media, especially when a relative water-insoluble or hydrophobic target molecule is used. In their quest for a short, polar spacer that enables fast and efficient conjugation of hydrophobic moieties, the inventors have developed the sulfamide linker, which was found to improve the solubility of the linker-conjugate, which in turn significantly improves the efficacy efficiency of the conjugation and reduces aggregation both in process and product.

The inventors found that the sulfamide linkers according to the present invention are capable of (a) improving conjugation efficiency in the preparation of the bioconjugate, (b) reducing aggregation during the preparation of the bioconjugate and/or of the bioconjugate, (c) increasing stability of the bioconjugate, and/or (d) increasing therapeutic index of the bioconjugate.

The inventors further found that the bioconjugates according to the present invention, thus comprising the branched sulfamide linker according to the present invention, exhibited a greater therapeutic efficacy compared to the same bioconjugate, i.e. the same biomolecule, the same active substance (drug) and the same biomolecule drug ratio, containing a linker not according to the present invention. That the structure of the linker could have an effect on the therapeutic efficacy of a bioconjugate, such as an antibody-drug-conjugate, could not be envisioned based on the current knowledge. In the field, linkers are considered inert when it comes to treatment and are solely present as a consequence of the preparation of the bioconjugate. That a specific structural element within a linker has an effect on the therapeutic efficacy is unprecedented in the art and a breakthrough discovery in the field of bioconjugates, in particular antibody-drug-conjugates. The bioconjugates according to the invention are thus more therapeutically effective as the same bioconjugates, i.e. the same biomolecule, the same active substance (drug) and the same biomolecule drug ratio, containing a different linker. This finding has dramatic implications on the treatment of subjects with the bioconjugate according to the invention, as treatment doses may be lowered and as a consequence potential, unwanted, side-effects are reduced. Alternatively, as a result of the increased tolerability of the bioconjugate (i.e. increased stability and low aggregation potential) according to the invention, treatment doses might be increased without the potential increase in unwanted side-effects.

Definitions

The verb "to comprise", and its conjugations, as used in this description and in the claims is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there is one and only one of the elements. The indefinite article "a" or "an" thus usually means "at least one".

The compounds disclosed in this description and in the claims may comprise one or more asymmetric centres, and different diastereomers and/or enantiomers may exist of the compounds. The description of any compound in this description and in the claims is meant to include all diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer.

The compounds may occur in different tautomeric forms. The compounds according to the invention are meant to include all tautomeric forms, unless stated otherwise. When the structure of a compound is depicted as a specific tautomer, it is to be understood that the invention of the present application is not limited to that specific tautomer.

The compounds disclosed in this description and in the claims may further exist as exo and endo diastereoisomers. Unless stated otherwise, the description of any compound in the description and in the claims is meant to include both the individual exo and the individual endo diastereoisomers of a compound, as well as mixtures thereof. When the structure of a compound is depicted as a specific endo or exo diastereomer, it is to be understood that the invention of the present application is not limited to that specific endo or exo diastereomer.

Furthermore, the compounds disclosed in this description and in the claims may exist as cis and trans isomers. Unless stated otherwise, the description of any compound in the description and in the claims is meant to include both the individual cis and the individual trans isomer of a compound, as well as mixtures thereof. As an example, when the structure of a compound is depicted as a cis isomer, it is to be understood that the corresponding trans isomer or mixtures of the cis and trans isomer are not excluded from the invention of the present application. When the structure of a compound is depicted as a specific cis or trans isomer, it is to be understood that the invention of the present application is not limited to that specific cis or trans isomer.

The compounds according to the invention may exist in salt form, which are also covered by the present invention. The salt is typically a pharmaceutically acceptable salt, containing a pharmaceutically acceptable anion. The term "salt thereof" means a compound formed when an acidic proton, typically a proton of an acid, is replaced by a cation, such as a metal cation or an organic cation and the like. Where applicable, the salt is a pharmaceutically acceptable salt, although this is not required for salts that are not intended for administration to a patient. For example, in a salt of a compound the compound may be protonated by an inorganic or organic acid to form a cation, with the conjugate base of the inorganic or organic acid as the anionic component of the salt.

The term "pharmaceutically accepted" salt means a salt that is acceptable for administration to a patient, such as a mammal (salts with counter ions having acceptable mammalian safety for a given dosage regime). Such salts may be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions known in the art and include, for example, sodium, potassium, calcium, magnesium, ammonium, tetraalkylammonium, etc., and when the molecule contains a basic functionality, salts of organic or inorganic acids, such as hydrochloride, hydrobromide, formate, tartrate, besylate, mesylate, acetate, maleate, oxalate, etc.

Unsubstituted alkyl groups have the general formula $C_nH_{2n+1}$ and may be linear or branched. Optionally, the alkyl groups are substituted by one or more substituents further specified in this document. Examples of alkyl groups include methyl, ethyl, propyl, 2-propyl, t-butyl, 1-hexyl, 1-dodecyl, etc.

A cycloalkyl group is a cyclic alkyl group. Unsubstituted cycloalkyl groups comprise at least three carbon atoms and have the general formula $C_nH_{2n-1}$. Optionally, the cycloalkyl groups are substituted by one or more substituents further specified in this document. Examples of cycloalkyl groups include cyclopropyl, cyclobutyl, cyclopentyl and cyclohexyl.

An alkenyl group comprises one or more carbon-carbon double bonds, and may be linear or branched. Unsubstituted alkenyl groups comprising one C—C double bond have the general formula $C_nH_{2n-1}$. Unsubstituted alkenyl groups comprising two C—C double bonds have the general formula $C_nH_{2n-3}$. An alkenyl group may comprise a terminal carbon-carbon double bond and/or an internal carbon-carbon double bond. A terminal alkenyl group is an alkenyl group wherein a carbon-carbon double bond is located at a terminal position of a carbon chain. An alkenyl group may also comprise two or more carbon-carbon double bonds. Examples of an alkenyl group include ethenyl, propenyl, isopropenyl, t-butenyl, 1,3-butadienyl, 1,3-pentadienyl, etc. Unless stated otherwise, an alkenyl group may optionally be substituted with one or more, independently selected, substituents as defined below. Unless stated otherwise, an alkenyl group may optionally be interrupted by one or more heteroatoms independently selected from the group consisting of O, N and S.

An alkynyl group comprises one or more carbon-carbon triple bonds, and may be linear or branched. Unsubstituted alkynyl groups comprising one C—C triple bond have the general formula $C_nH_{2n-3}$. An alkynyl group may comprise a terminal carbon-carbon triple bond and/or an internal carbon-carbon triple bond. A terminal alkynyl group is an alkynyl group wherein a carbon-carbon triple bond is located at a terminal position of a carbon chain. An alkynyl group may also comprise two or more carbon-carbon triple bonds. Unless stated otherwise, an alkynyl group may optionally be substituted with one or more, independently selected, substituents as defined below. Examples of an alkynyl group include ethynyl, propynyl, isopropynyl, t-butynyl, etc. Unless stated otherwise, an alkynyl group may optionally be interrupted by one or more heteroatoms independently selected from the group consisting of O, N and S.

An aryl group comprises six to twelve carbon atoms and may include monocyclic and bicyclic structures. Optionally, the aryl group may be substituted by one or more substituents further specified in this document. Examples of aryl groups are phenyl and naphthyl.

Arylalkyl groups and alkylaryl groups comprise at least seven carbon atoms and may include monocyclic and bicyclic structures. Optionally, the arylalkyl groups and alkylaryl may be substituted by one or more substituents further specified in this document. An arylalkyl group is for example benzyl. An alkylaryl group is for example 4-t-butylphenyl.

Heteroaryl groups comprise at least two carbon atoms (i.e. at least $C_2$) and one or more heteroatoms N, O, P or S. A heteroaryl group may have a monocyclic or a bicyclic structure. Optionally, the heteroaryl group may be substituted by one or more substituents further specified in this document. Examples of suitable heteroaryl groups include pyridinyl, quinolinyl, pyrimidinyl, pyrazinyl, pyrazolyl, imidazolyl, thiazolyl, pyrrolyl, furanyl, triazolyl, benzofuranyl, indolyl, purinyl, benzoxazolyl, thienyl, phospholyl and oxazolyl.

Heteroarylalkyl groups and alkylheteroaryl groups comprise at least three carbon atoms (i.e. at least $C_3$) and may include monocyclic and bicyclic structures. Optionally, the heteroaryl groups may be substituted by one or more substituents further specified in this document.

Where an aryl group is denoted as a (hetero)aryl group, the notation is meant to include an aryl group and a heteroaryl group. Similarly, an alkyl(hetero)aryl group is meant to include an alkylaryl group and a alkylheteroaryl group, and (hetero)arylalkyl is meant to include an arylalkyl group and a heteroarylalkyl group. A $C_2$-$C_{24}$ (hetero)aryl group is thus to be interpreted as including a $C_2$-$C_{24}$ heteroaryl group and a $C_6$-$C_{24}$ aryl group. Similarly, a $C_3$-$C_{24}$ alkyl(hetero)aryl group is meant to include a $C_7$-$C_{24}$ alkylaryl group and a $C_3$-$C_{24}$ alkylheteroaryl group, and a $C_3$-$C_{24}$ (hetero)arylalkyl is meant to include a $C_7$-$C_{24}$ arylalkyl group and a $C_3$-$C_{24}$ heteroarylalkyl group. A cycloalkynyl group is a cyclic alkynyl group. An unsubstituted cycloalkynyl group comprising one triple bond has the general formula $C_nH_{2n-5}$. Optionally, a cycloalkynyl group is substituted by one or more substituents further specified in this document. An example of a cycloalkynyl group is cyclooctynyl.

A heterocycloalkynyl group is a cycloalkynyl group interrupted by heteroatoms selected from the group of oxygen, nitrogen and sulphur. Optionally, a heterocycloalkynyl group is substituted by one or more substituents further specified in this document. An example of a heterocycloalkynyl group is azacyclooctynyl.

A (hetero)aryl group comprises an aryl group and a heteroaryl group. An alkyl(hetero)aryl group comprises an alkylaryl group and an alkylheteroaryl group. A (hetero)arylalkyl group comprises a arylalkyl group and a heteroarylalkyl groups. A (hetero)alkynyl group comprises an alkynyl group and a heteroalkynyl group. A (hetero)cycloalkynyl group comprises an cycloalkynyl group and a heterocycloalkynyl group.

A (hetero)cycloalkyne compound is herein defined as a compound comprising a (hetero)cycloalkynyl group.

Several of the compounds disclosed in this description and in the claims may be described as fused (hetero)cycloalkyne compounds, i.e. (hetero)cycloalkyne compounds wherein a second ring structure is fused, i.e. annulated, to the (hetero)cycloalkynyl group. For example in a fused (hetero)cyclooctyne compound, a cycloalkyl (e.g. a cyclopropyl) or an arene (e.g. benzene) may be annulated to the (hetero)cyclooctynyl group. The triple bond of the (hetero)cyclooctynyl group in a fused (hetero)cyclooctyne compound may be located on either one of the three possible locations, i.e. on the 2, 3 or 4 position of the cyclooctyne moiety (numbering according to "IUPAC Nomenclature of Organic Chemistry", Rule A31.2). The description of any fused (hetero)cyclooctyne compound in this description and in the claims is meant to include all three individual regioisomers of the cyclooctyne moiety.

Unless stated otherwise, alkyl groups, cycloalkyl groups, alkenyl groups, alkynyl groups, (hetero)aryl groups, (hetero)arylalkyl groups, alkyl(hetero)aryl groups, alkylene groups, alkenylene groups, alkynylene groups, cycloalkylene groups, cycloalkenylene groups, cycloalkynylene groups, (hetero)arylene groups, alkyl(hetero)arylene groups, (hetero)arylalkylene groups, (hetero)arylalkenylene groups, (hetero)arylalkynylene groups, alkenyl groups, alkoxy groups, alkenyloxy groups, (hetero)aryloxy groups, alkynyloxy groups and cycloalkyloxy groups may be substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo and silyl groups, wherein the silyl groups can be represented by the formula $(R^{20})_3Si$—, wherein $R^{20}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S.

The general term "sugar" is herein used to indicate a monosaccharide, for example glucose (Glc), galactose (Gal), mannose (Man) and fucose (Fuc). The term "sugar derivative" is herein used to indicate a derivative of a monosaccharide sugar, i.e. a monosaccharide sugar comprising substituents and/or functional groups. Examples of a sugar derivative include amino sugars and sugar acids, e.g. glucosamine (GlcNFh), galactosamine (GalNH$_2$)N-acetylglucosamine (GlcNAc), N-acetylgalactosamine (GalNAc), sialic acid (Sia) which is also referred to as N-acetylneuraminic acid (NeuNAc), and N-acetylmuramic acid (MurNAc), glucuronic acid (GlcA) and iduronic acid (IdoA).

The term "nucleotide" is herein used in its normal scientific meaning. The term "nucleotide" refers to a molecule that is composed of a nucleobase, a five-carbon sugar (either ribose or 2-deoxyribose), and one, two or three phosphate groups. Without the phosphate group, the nucleobase and sugar compose a nucleoside. A nucleotide can thus also be called a nucleoside monophosphate, a nucleoside diphosphate or a nucleoside triphosphate. The nucleobase may be adenine, guanine, cytosine, uracil or thymine. Examples of a nucleotide include uridine diphosphate (UDP), guanosine diphosphate (GDP), thymidine diphosphate (TDP), cytidine diphosphate (CDP) and cytidine monophosphate (CMP).

The term "protein" is herein used in its normal scientific meaning. Herein, polypeptides comprising about 10 or more amino acids are considered proteins. A protein may comprise natural, but also unnatural amino acids.

The term "glycoprotein" is herein used in its normal scientific meaning and refers to a protein comprising one or more monosaccharide or oligosaccharide chains ("glycans") covalently bonded to the protein. A glycan may be attached to a hydroxyl group on the protein (O-linked-glycan), e.g. to the hydroxyl group of serine, threonine, tyrosine, hydroxylysine or hydroxyproline, or to an amide function on the protein (N-glycoprotein), e.g. asparagine or arginine, or to a carbon on the protein (C-glycoprotein), e.g. tryptophan. A glycoprotein may comprise more than one glycan, may comprise a combination of one or more monosaccharide and one or more oligosaccharide glycans, and may comprise a combination of N-linked, O-linked and C-linked glycans. It is estimated that more than 50% of all proteins have some form of glycosylation and therefore qualify as glycoprotein. Examples of glycoproteins include PSMA (prostate-specific membrane antigen), CAL (*Candida antartica* lipase), gp41, gp120, EPO (erythropoietin), antifreeze protein and antibodies.

The term "glycan" is herein used in its normal scientific meaning and refers to a monosaccharide or oligosaccharide chain that is linked to a protein. The term glycan thus refers to the carbohydrate-part of a glycoprotein. The glycan is attached to a protein via the C-1 carbon of one sugar, which may be without further substitution (monosaccharide) or may be further substituted at one or more of its hydroxyl groups (oligosaccharide). A naturally occurring glycan typically comprises 1 to about 10 saccharide moieties. However, when a longer saccharide chain is linked to a protein, said saccharide chain is herein also considered a glycan. A glycan of a glycoprotein may be a monosaccharide. Typically, a monosaccharide glycan of a glycoprotein consists of a single N-acetylglucosamine (GlcNAc), glucose (Glc), mannose (Man) or fucose (Fuc) covalently attached to the protein. A glycan may also be an oligosaccharide. An oligosaccharide chain of a glycoprotein may be linear or branched. In an oligosaccharide, the sugar that is directly attached to the protein is called the core sugar. In an oligosaccharide, a sugar that is not directly attached to the protein and is attached to at least two other sugars is called an internal sugar. In an oligosaccharide, a sugar that is not directly attached to the protein but to a single other sugar, i.e. carrying no further sugar substituents at one or more of its other hydroxyl groups, is called the terminal sugar. For the avoidance of doubt, there may exist multiple terminal sugars in an oligosaccharide of a glycoprotein, but only one core sugar. A glycan may be an O-linked glycan, an N-linked glycan or a C-linked glycan. In an O-linked glycan a monosaccharide or oligosaccharide glycan is bonded to an O-atom in an amino acid of the protein, typically via a hydroxyl group of serine (Ser) or threonine (Thr). In an N-linked glycan a monosaccharide or oligosaccharide glycan is bonded to the protein via an N-atom in an amino acid of the protein, typically via an amide nitrogen in the side chain of asparagine (Asn) or arginine (Arg). In a C-linked glycan a monosaccharide or oligosaccharide glycan is bonded to a C-atom in an amino acid of the protein, typically to a C-atom of tryptophan (Trp).

The term "antibody" is herein used in its normal scientific meaning. An antibody is a protein generated by the immune system that is capable of recognizing and binding to a specific antigen. An antibody is an example of a glycoprotein. The term antibody herein is used in its broadest sense and specifically includes monoclonal antibodies, polyclonal antibodies, dimers, multimers, multi-specific antibodies (e.g. bispecific antibodies), antibody fragments, and double and single chain antibodies. The term "antibody" is herein also meant to include human antibodies, humanized antibodies, chimeric antibodies and antibodies specifically binding cancer antigen. The term "antibody" is meant to include whole antibodies, but also antigen-binding fragments of an antibody, for example an antibody Fab fragment, $F(ab')_2$, Fv fragment or Fc fragment from a cleaved antibody, a scFv-Fc fragment, a minibody, a diabody or a scFv. Furthermore, the term includes genetically engineered antibodies and derivatives of an antibody. Antibodies, fragments of antibodies and genetically engineered antibodies may be obtained by methods that are known in the art. Typical examples of antibodies include, amongst others, abciximab, rituximab, basiliximab, palivizumab, infliximab, trastuzumab, alemtuzumab, adalimumab, tositomomab-I131, cetuximab, ibrituximab tiuxetan, omalizumab, bevacizumab, natalizumab, ranibizumab, panitumumab, eculizumab, certolizumab pegol, golimumab, canakinumab, catumaxomab, ustekinumab, tocilizumab, ofatumumab, denosumab, belimumab, ipilimumab and brentuximab.

A linker is herein defined as a moiety that connects two or more elements of a compound. For example in a bioconjugate, a biomolecule and a target molecule are covalently connected to each other via a linker; in the linker-conjugate a reactive group $Q^1$ is covalently connected to a target molecule via a linker; in a linker-construct a reactive group $Q^1$ is covalently connected to a reactive group $Q^2$ via a linker. A linker may comprise one or more spacer-moieties.

A spacer-moiety is herein defined as a moiety that spaces (i.e. provides distance between) and covalently links together two (or more) parts of a linker. The linker may be part of e.g. a linker-construct, the linker-conjugate or a bioconjugate, as defined below.

A linker-construct is herein defined as a compound wherein a reactive group $Q^1$ is covalently connected to a reactive group $Q^2$ via a linker. A linker-construct comprises a reactive group $Q^1$ capable of reacting with a reactive group present on a biomolecule, and a reactive group $Q^2$ capable of reacting with a reactive group present on a target molecule. $Q^1$ and $Q^2$ may be the same, or different. A linker-construct may also comprise more than one reactive group $Q^1$ and/or more than one reactive group $Q^2$. A linker-construct may also be denoted as $Q^1$-Sp-$Q^2$, wherein $Q^1$ is a reactive group capable of reacting with a reactive group $F^1$ present on a biomolecule, $Q^2$ is a reactive group capable of reacting with a reactive group $F^2$ present on a target molecule and Sp is a spacer moiety. When a linker-construct comprises more than one reactive group $Q^1$ and/or more than one reactive group $Q^2$, the linker-construct may be denoted as $(Q^1)_y$-Sp-$(Q^2)_z$, wherein y is an integer in the range of 1 to 10 and z is an integer in the range of 1 to 10. Preferably, y is 1, 2, 3 or 4, more preferably y is 1 or 2 and most preferably, y is 1. Preferably, z is 1, 2, 3, 4, 5 or 6, more preferably z is 1, 2, 3 or 4, even more preferably z is 1, 2 or 3, yet even more preferably z is 1 or 2 and most preferably z is 1. More preferably, y is 1 or 2, preferably 1, and z is 1, 2, 3 or 4, yet even more preferably y is 1 or 2, preferably 1, and z is 1, 2 or 3, yet even more preferably y is 1 or 2, preferably 1, and z is 1 or 2, and most preferably y is 1 and z is 1.

A bioconjugate is herein defined as a compound wherein a biomolecule is covalently connected to a target molecule via a linker. A bioconjugate comprises one or more biomolecules and/or one or more target molecules. The linker may comprise one or more spacer moieties.

When a compound is herein referred to as a compound comprising an alpha-end and an omega-end, said compound comprises two (or more) ends, the first end being referred to as the alpha-end and the second end being referred to as the omega-end. Said compound may comprise more than two ends, i.e. a third, fourth etc. end may be present in the compound.

A biomolecule is herein defined as any molecule that can be isolated from nature or any molecule composed of smaller molecular building blocks that are the constituents of macromolecular structures derived from nature, in particular nucleic acids, proteins, glycans and lipids. Examples of a biomolecule include an enzyme, a (non-catalytic) protein, a polypeptide, a peptide, an amino acid, an oligonucleotide, a monosaccharide, an oligosaccharide, a polysaccharide, a glycan, a lipid and a hormone.

A target molecule, also referred to as a molecule of interest (MOI), is herein defined as molecular structure possessing a desired property that is imparted onto the biomolecule upon conjugation.

Herein, a sulfamide linker and conjugates of said sulfamide linker are disclosed. The term "sulfamide linker" refers to a linker comprising a sulfamide group, more particularly an acylsulfamide group [—C(O)—N(H)—S(O)$_2$—N(R$^1$)—] and/or a carbamoyl sulfamide group [—O—C(O)—N(H)—S(O)$_2$—N(R$^1$)—].

Herein, the term "therapeutic index" (TI) has the conventional meaning well known to a person skilled in the art, and refers to the ratio of the dose of drug that is toxic (i.e. causes adverse effects at an incidence or severity not compatible with the targeted indication) for 50% of the population (TD$_{50}$) divided by the dose that leads to the desired pharmacological effect in 50% of the population (effective dose or $ED_{50}$). Hence, $TI=TD_{50}/ED_{50}$. The therapeutic index may be determined by clinical trials or for example by plasma exposure tests. See also Muller, et al. *Nature Reviews Drug Discovery* 2012, 11, 751-761.

Herein, the term "therapeutic efficacy" denotes the capacity of a substance to achieve a certain therapeutic effect, e.g. reduction in tumour volume. Therapeutic effects can be measured determining the extent in which a substance can achieve the desired effect, typically in comparison with another substance under the same circumstances. A suitable measure for the therapeutic efficacy is the $ED_{50}$ value, which may for example be determined during clinical trials or by plasma exposure tests. In case of preclinical therapeutic efficacy determination, the therapeutic effect of a bioconjugate (e.g. an ADC), can be validated by patient-derived tumour xenografts in mice in which case the efficacy refers to the ability of the ADC to provide a beneficial effect. Alternatively the tolerability of said ADC in a rodent safety study can also be a measure of the therapeutic effect.

Herein, the term "tolerability" refers to the maximum dose of a specific substance that does not cause adverse effects at an incidence or severity not compatible with the targeted indication. A suitable measure for the tolerability for a specific substance is the $TD_{50}$ value, which may for example be determined during clinical trials or by plasma exposure tests.

Linker

A linker is herein defined as a moiety that connects two or more elements of a compound. For example in a bioconjugate, a biomolecule and a target molecule are covalently connected to each other via a linker; in a linker-conjugate a reactive group $Q^1$ is covalently connected to a target molecule via a linker; in a linker-construct a reactive group $Q^1$ is covalently connected to a reactive group $Q^2$ via a linker.

In the context of the present invention, the linker-construct, linker-conjugate and bioconjugate according to the invention comprise a branched sulfamide linker. The term "branched sulfamide linker" refers to a linker comprising a sulfamide group, more particularly an acylsulfamide group [—C(O)—N(H)—S(O)$_2$—N(R$^1$)—] and/or a carbamoyl sulfamide group [—O—C(O)—N(H)—S(O)$_2$—N(R$^1$)—]. The linker according to the invention further comprises branching moiety (BM).

Branching Moiety BM

A "branching moiety" in the context of the present invention refers to a moiety that is embedded in a linker connecting two moieties, in particular a target molecule D and a reactive group $Q^1$, or a target molecule D and a biomolecule B, or a reactive group $Q^1$ and a reactive group $Q^2$, and further comprises a branch points that connects to the sulfamide group according to the present invention. In other words, the branching moiety comprises at least three bonds to other moieties, one bond to reactive group $Q^2$ or target molecule D, optionally via a spacer, one bond to reactive group $Q^1$ or biomolecule B, optionally via a spacer, and one bond to sulfamide group SG, optionally via a spacer. Branching moiety BM may contain additional bonds to other moieties, such as two or more bonds to target molecules, two or more bonds to reactive groups or biomolecules and/or two or more bonds to sulfamide groups. In one embodiment, the branching moiety comprises 3, 4, 5 or 6 bonds to other moieties, preferably 3 or 4 bonds to other moieties. In case the branching moiety contains more than 3 bonds to other moieties, it is preferred that two or more bonds are to a target molecule. Any moiety that contains at least three bonds to other moieties is suitable as branching moiety in the context of the present invention. Suitable branching moieties include a carbon atom (BM-1 and BM-2), a nitrogen atom (amine (BM-3) and ammonium (BM-4)), a phosphorus atom (phosphine (BM-5) and phosphine oxide (BM-6)), aromatic rings such as a phenyl ring (e.g. BM-7 and BM-8) or a pyridyl ring (e.g. BM-9 and BM-10), a (hetero)cycle (e.g. BM-11 and BM-12) and polycyclic moieties (e.g. BM-13, BM-14 and BM-15). Preferred branching moieties are selected from carbon atoms and phenyl rings, most preferably BM is a carbon atom. Structures (BM-1) to (BM-15) are depicted here below, wherein the three or four branches, i.e. bonds to other moieties as defined above, are indicated by —*— (a bond labelled with *).

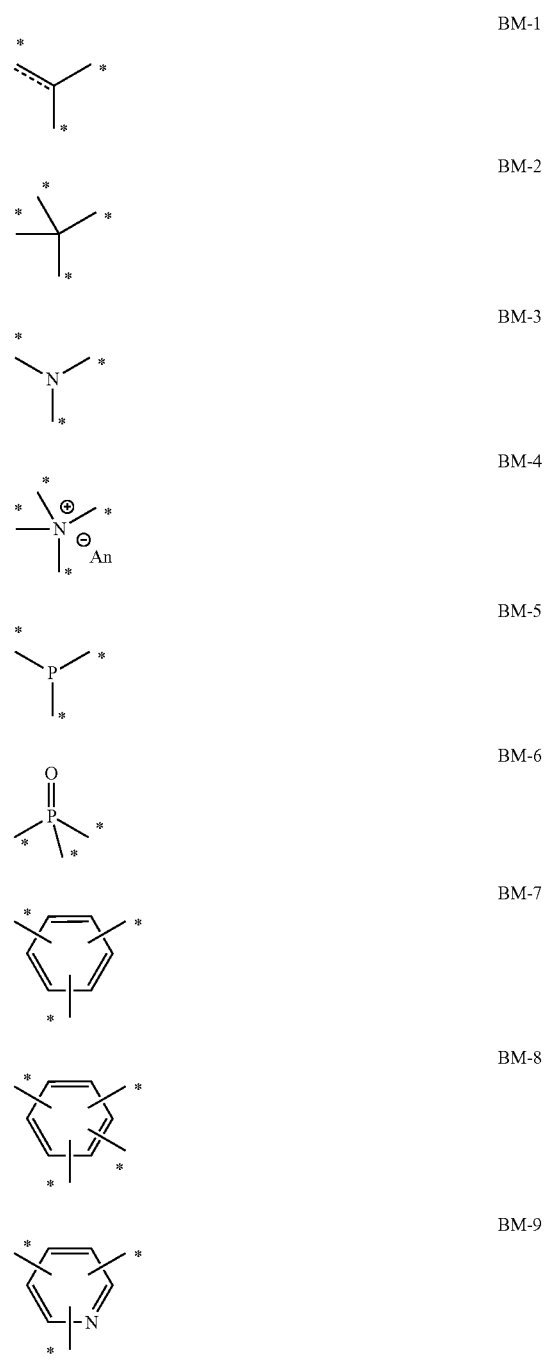

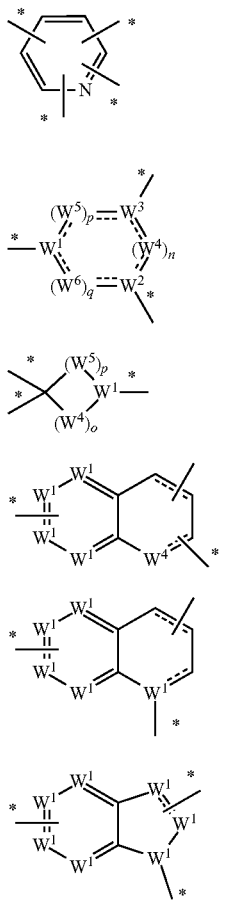

In (BM-1), one of the branches labelled with * may be a single or a double bond, indicated with ----. In (BM-4), An⁻ is an anion, typically a pharmaceutically acceptable anion. In (BM-11) to (BM-15), the following applies:
- each of p, q and q is individually an integer in the range of 0-5, preferably 0 or 1, most preferably 1;
- each of $W^1$, $W^2$ and $W^3$ is independently selected from $C(R^{21})_r$ and N;
- each of $W^4$, $W^5$ and $W^6$ is independently selected from $C(R^{21})_{r+1}$, $N(R^{22})_r$, O and S;
- each ---- represents a single or double bond;
- r is 0 or 1 or 2, preferably 0 or 1;
- each $R^{21}$ is independently selected from the group consisting of hydrogen, OH, $C_1$-$C_{24}$ alkyl groups, $C_1$-$C_{24}$ alkoxy groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the $C_1$-$C_{24}$ alkyl groups, $C_1$-$C_{24}$ alkoxy groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups are optionally substituted and optionally interrupted by one or more heteroatoms selected from O, S and $NR^3$ wherein $R^3$ is independently selected from the group consisting of hydrogen and $C_1$-$C_4$ alkyl groups, or $R^{21}$ is a further branch —*—, connected to a further occurrence of SG, D, $Q^1$, $Q^2$ or B, optionally via a spacer; and
- each $R^{22}$ is independently selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the $C_1$-$C_{24}$ alkyl groups, $C_1$-$C_{24}$ alkoxy groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups are optionally substituted and optionally interrupted by one or more heteroatoms selected from O, S and $NR^3$ wherein $R^3$ is independently selected from the group consisting of hydrogen and $C_1$-$C_4$ alkyl groups, or $R^{22}$ is a further branch —*—, connected to a further occurrence of SG, D, $Q^1$, $Q^2$ or B, optionally via a spacer The skilled person appreciates that the values of r and the bond order of the bonds represented by ---- are interdependent. Thus, whenever an occurrence of W is bonded to an endocyclic double bond, r=1 for that occurrence of W, while whenever an occurrence of W is bonded to two endocyclic single bonds, r=0 for that occurrence of W. For BM-12, at least one of 0 and p is not 0.

Representative examples of branching moieties according to structure (BM-11) and (BM-12) include cyclopropyl, cyclobutyl, cyclopentyl, cyclohexyl, cycloheptyl, cyclooctyl, cyclopropenyl, cyclobutenyl, cyclopentenyl, cyclohexenyl, cycloheptenyl, cyclooctenyl, aziridine, azetidine, diazetidine, oxetane, thietane, pyrrolidine, dihydropyrrolyl, tetrahydrofuranyl, dihydrofuranyl, thiolanyl, imidazolinyl, pyrazolidinyl, oxazolidinyl, isoxazolidinyl, thiazolidinyl, isothiazolidinyl, dioxolanyl, dithiolanyl, piperidinyl, oxanyl, thianyl, piperazinyl, morpholino, thiomorpholino, dioxanyl, trioxanyl, dithyanyl, trithianyl, azepanyl, oxepanyl and thiepanyl. Preferred cyclic moieties for use as branching moiety include cyclopropenyl, cyclohexyl, oxanyl and dioxanyl. The substitution pattern of the three branches determines whether the branching moiety is of structure (BM-11) or of structure (BM-12). In one embodiment, BM is not cyclopropyl. In one embodiment, BM is not pyrrolidine.

Representative examples of branching moieties according to structure (BM-13) to (BM-15) include decalin, tetralin, dialin, naphthalene, indene, indane, isoindene, indole, isoindole, indoline, isoindoline, and the like.

At least one, preferably one or two, of the branches indicated with * in structures (BM-1) to (BM-15) is connected to reactive group $Q^2$ or target molecule D. At least one, preferably one, of the branches indicated with * in structures (BM-1) to (BM-15) is connected to reactive group $Q^1$ or biomolecule B. At least one, preferably one or two, of the branches indicated with * in structures (BM-1) to (BM-15) is connected to sulfamide group SG.

In case a branching moiety contains four branches (bonds labelled with *), two of those may be connected or may be part of a single occurrence of SG, D, $Q^1$, $Q^2$ or B, via a cyclic moiety. For example, in case the branching moiety is the carbon atom of BM-2, one bond may be to SG, one bond may be to D and two bonds may form a cycle, e.g. a cyclopropyl ring, that is part of $Q^1$, for example part of a cyclooctyne ring.

In a preferred embodiment, BM is a carbon atom. In case the carbon atom is according to structure (BM-2) and two of the branches indicated with * are connected to identical moieties, than the carbon atom is not chiral. Such two identical moieties may be two target molecules D, optionally linked via a spacer, two biomolecules B, optionally linked via a spacer, or two sulfamide groups SG-E, optionally linked via a spacer, preferably two target molecules D, optionally linked via a spacer. However, in case the carbon atom is according to structure (BM-1) or is according to structure (BM-2) and all four bonds are to distinct moieties, e.g. when two target molecules D, optionally linked via a spacer, are linked to the branching moiety according to structure (BM-2), wherein the target molecules and/or the spacer differ, the carbon atom is chiral. The stereochemistry of the carbon atom is not crucial for the present invention, and may be S or R. The same holds for the quaternary ammonium ion of (BM-4) and phosphine (BM-6). Most preferably, the carbon atom is according to structure (BM-1).

One of the branches indicated with * in the carbon atom according to structure (BM-1) may be a double bond, in which case the carbon atom may be part of an alkene or imine. In case BM is a carbon atom, the carbon atom may be part of a larger functional group, such as an acetal, a ketal, a hemiketal, an orthoester, an orthocarbonate ester, and the like. This also holds in case BM is a nitrogen or phosphorus atom, in which case it may be part of an amide, an imide, an imine, a phosphine oxide (as in BM-6) or a phosphotriester.

In a preferred embodiment, BM is a phenyl ring. Phenyl rings may be tri-, tetra-, penta- or hexa-substituted, preferably they are tri- or tetra-substituted, i.e. according to structure (BM-7) or structure (BM-8), respectively. Most preferably, the phenyl ring is according to structure (BM-7). The substitution pattern of the phenyl ring may be of any regiochemistry, such as 1,2,3-substituted phenyl rings, 1,2,4-substituted phenyl rings, 1,3,5-substituted phenyl rings, 1,2,3,4-substituted phenyl rings, 1,2,3,5-substituted phenyl rings or 1,2,4,5-substituted phenyl rings. To allow optimal flexibility and conformational freedom, it is preferred that the phenyl ring is according to structure (BM-7), most preferably the phenyl ring is 1,3,5-substituted. The same holds for the pyridine rings of (BM-9) and (BM-10).

Sulfamide Group SG

In the linker of the present invention, branching moiety BM is connected to the sulfamide group SG according to formula (1). Herein, the bonds to the other moieties of the compounds according to the inventions are indicated by 1 and 2. Sulfamide group SG is connected via one of the bonds indicated with 1 and 2 to branching moiety BM, optionally via a spacer, and with the other bond indicated with 1 or 2 to capping group E, optionally via a spacer.

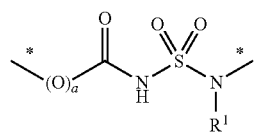

(1)

Herein:
a is 0 or 1; and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups are optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a further target molecule D, wherein the target molecule is optionally connected to N via a spacer moiety.

The linker according to the invention comprises a group according to formula (1) as defined above. In a preferred embodiment, the linker according to the invention comprises a group according to formula (1) wherein a is 0, or a salt thereof. In this embodiment, the compound thus comprises a group according to formula (2) or a salt thereof:

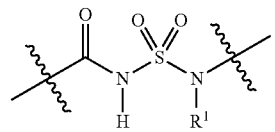

2 wherein $R^1$ is as defined above.

In another preferred embodiment, the linker according to the invention comprises a group according to formula (1) wherein a is 1. In this embodiment, the linker thus comprises a group according to formula (3) or a salt thereof:

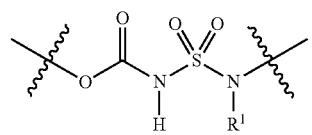

3 wherein $R^1$ is as defined above.

In the groups according to formula (1), (2) and (3), $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a target molecule D, wherein the target molecule is optionally connected to N via a spacer moiety. In one embodiment, in case $R^1$ is a target molecule D, optionally connected via a spacer, D is not a drug or a prodrug, preferably not an active substance. In one embodiment, $R^1$ is not D.

In a preferred embodiment, $R^1$ is hydrogen or a $C_1$-$C_{20}$ alkyl group, more preferably $R^1$ is hydrogen or a $C_1$-$C_{16}$ alkyl group, even more preferably $R^1$ is hydrogen or a $C_1$-$C_{10}$ alkyl group, wherein the alkyl group is optionally substituted and optionally interrupted by one or more heteroatoms selected from O, S and $NR^3$, preferably O, wherein $R^3$ is independently selected from the group consisting of hydrogen and $C_1$-$C_4$ alkyl groups. In a preferred embodiment, $R^1$ is hydrogen. In another preferred embodiment, $R^1$ is a $C_1$-$C_{20}$ alkyl group, more preferably a $C_1$-$C_{16}$ alkyl group, even more preferably a $C_1$-$C_{10}$ alkyl group, wherein the alkyl group is optionally interrupted by one or more O-atoms, and wherein the alkyl group is optionally substituted with an —OH group, preferably a terminal —OH group. In this embodiment, it is further preferred that $R^1$ is a (poly)ethylene glycol chain comprising a terminal —OH group. In another preferred embodiment, $R^1$ is selected from the group consisting of hydrogen, methyl, ethyl, n-propyl, i-propyl, n-butyl, s-butyl and t-butyl, more preferably from the group consisting of hydrogen, methyl, ethyl, n-propyl and i-propyl, and even more preferably from the group consisting of hydrogen, methyl and ethyl. Yet even more preferably $R^1$ is hydrogen or methyl, and most preferably $R^1$ is hydrogen.

In another preferred embodiment, $R^1$ is a target molecule D. Optionally, the target molecule D is connected to N via one or more spacer-moieties. The spacer-moiety, if present, is defined as a moiety that spaces, i.e. provides a certain distance between, and covalently links target molecule D and N. The target molecule D and preferred embodiments thereof are described in more detail below.

Capping Group E

Sulfamide group SG is connected to capping group E, optionally via a spacer moiety. Any group or moiety known in the art to act as capping group may be used as capping group E. Suitable capping groups include hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups, $C_3$-$C_{24}$ (hetero)arylalkyl groups, polyethylene glycol groups represented by —$(CH_2CH_2O)_pCH_3$ (wherein p=1-10, preferably 2-4), wherein the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups are optionally substituted and optionally interrupted by one or more heteroatoms selected from O, S and $NR^3$ wherein $R^3$ is independently selected from the group consisting of hydrogen and $C_1$-$C_4$ alkyl groups, or E is a further target molecule D. In one embodiment, in case E is a target molecule D, D is not a drug or a prodrug, preferably not an active substance. In one embodiment, E is not D.

In one embodiment, both $R^1$ and E are further target molecules D, which may be the same or different and the same or different as the target molecule D in the main chain. In one embodiment, one of $R^1$ and E is a further target molecule D, which may be the same or different as the target molecule D in the main chain. In one embodiment, both $R^1$ and E are not a further target molecule D.

In one embodiment, E is a polyethylene glycol groups, which is typically represented by —$(CH_2CH_2O)_sCH_3$, wherein s is an integer in the range of 1-10, preferably 2-4. In one embodiment, E is a $C_1$-$C_{24}$ alkyl group, $C_2$-$C_{24}$ (hetero)aryl group or a $C_3$-$C_{24}$ alkyl(hetero)aryl group, preferably a $C_6$-$C_{12}$ alkaryl group, most preferably a benzyl group.

The linker according to the present invention connects reactive group $Q^2$ or target molecule D on one hand, and reactive group $Q^1$ or biomolecule B on the other hand.

Preferred Linkers

Sulfamide linkers according to the present invention are preferably represented by formula (2):

$$\underset{(Sp^3)_g}{*}\!\!-\!\!(Z^1)_d\!\!-\!\!(Sp^2)_c\!\!-\!\!\underset{\underset{f}{|}}{\overset{\overset{(Sp^5)_k\!\!-\!\!SG\!\!-\!\!(Sp^6)_l\!\!-\!\!E}{|}}{BM}}\!\!-\!\!(Sp^1)_b\!\!-\!\!(Z^2)_e\!\!-\!\!(Sp^4)_i\!\!-\!\!* \quad (2)$$

Herein:
BM is a branching moiety as defined above;
E is a capping group as defined above;
SG is a sulfamide group according to formula (1), wherein a and $R^1$ are as defined above;
b is independently 0 or 1;
c is 0 or 1;
d is 0 or 1;
e is 0 or 1;
f is an integer in the range of 1 to 10;
g is 0 or 1;
i is 0 or 1;
k is 0 or 1;
l is 0 or 1;
$Sp^1$ is a spacer moiety;
$Sp^2$ is a spacer moiety;
$Sp^3$ is a spacer moiety;
$Sp^4$ is a spacer moiety;
$Sp^5$ is a spacer moiety;
$Sp^6$ is a spacer moiety;
$Z^1$ is a connecting group; and
$Z^2$ is a connecting group.

The bonds labelled with * in structure (2) are the bonds to the other moieties that are connected by the linker within the compounds according to the invention.

As will be understood by the person skilled in the art, preferred embodiments of the linker of structure (2) will depend on e.g. the nature of reactive groups $Q^1$ and D in the linker-conjugate, the synthetic method to prepare the linker-construct and linker-conjugate (e.g. the nature of complementary functional group $F^2$ on a target molecule), the nature of a bioconjugate that is prepared using the linker-conjugate (e.g. the nature of complementary functional group $F^1$ on the biomolecule).

When $Q^1$ is for example a cyclooctynyl group according to formula (9n), (9o), (9p), (9q) or (9zk) as defined below, then preferably $Sp^3$ is present (g is 1). When for example the linker-conjugate was prepared via reaction of a reactive group $Q^2$ that is a cyclooctynyl group according to formula (9n), (9o), (9p), (9q) or (9zk) with an azido functional group $F^2$, then preferably $Sp^4$ is present (i is 1). Furthermore, it is preferred that at least one of $Sp^1$, $Sp^2$, $Sp^3$ and $Sp^4$ is present, i.e. at least one of b, c, g, and i is not 0. In another preferred embodiment, at least one of $Sp^1$ and $Sp^4$ and at least one of $Sp^2$ and $Sp^3$ are present. When f is 2 or more, it is preferred that $Sp^1$ is present (b is 1). Preferred embodiments of $Sp^1$, $Sp^2$, $Sp^3$ and $Sp^4$ are as defined below.

As defined above, $Z^1$ is a connecting group that connects $Q^1$ or B or $Sp^3$ to $Sp^2$ or BM, and $Z^2$ is a connecting group that connects $Q^2$ or D or $Sp^4$ to $Sp^1$ or BM. As described in more detail above, the term "connecting group" refers to a structural element connecting one part of a compound and another part of the same compound.

In a compound according to formula (2), connecting group $Z^1$, when present (i.e. when d is 1), connects $Q^1$ or B (optionally via a spacer moiety $Sp^3$) to branching moiety BM, optionally via a spacer moiety $Sp^2$. More particularly, when $Z^1$ is present (i.e. d is 1), and when $Sp^3$ and $Sp^2$ are absent (i.e. g is 0 and c is 0), $Z^1$ connects $Q^1$ or B to BM of the linker according to formula (2). When $Z^1$ is present (i.e. when d is 1), $Sp^3$ is present (i.e. g is 1) and $Sp^2$ is absent (i.e. c is 0), $Z^1$ connects spacer moiety $Sp^3$ to BM of the linker according to formula (2). When $Z^1$ is present (i.e. d is 1), and when $Sp^3$ and $Sp^2$ are present (i.e. g is 1 and c is 1), $Z^1$ connects spacer moiety $Sp^3$ to spacer moiety $Sp^2$ of the linker according to formula (2). When $Z^1$ is present (i.e. when d is 1), $Sp^3$ is absent (i.e. g is 0) and $Sp^2$ is present (i.e. c is 1), $Z^1$ connects $Q^1$ or B to spacer moiety $Sp^2$ of the linker according to formula (2). In the compound according to formula (2), when c, d and g are all 0, then $Q^1$ or B is attached directly to BM of the linker according to formula (2).

In a compound according to formula (2), connecting group $Z^2$, when present (i.e. when e is 1), connects D or $Q^2$ (optionally via a spacer moiety $Sp^4$) to BM of the linker according to formula (2), optionally via a spacer moiety $Sp^1$. More particularly, when $Z^2$ is present (i.e. e is 1), and when $Sp^1$ and $Sp^4$ are absent (i.e. b is 0 and i is 0), $Z^2$ connects D or $Q^2$ to BM of the linker according to formula (2). When $Z^2$ is present (i.e. when e is 1), $Sp^4$ is present (i.e. i is 1) and $Sp^1$ is absent (i.e. b is 0), $Z^2$ connects spacer moiety $Sp^4$ to BM of the linker according to formula (2). When $Z^2$ is present (i.e. e is 1), and when $Sp^4$ and $Sp^1$ are present (i.e. b is 1 and i is 1), $Z^2$ connects spacer moiety $Sp^4$ to spacer moiety $Sp^1$ of the linker according to formula (2). When $Z^2$ is present (i.e. when e is 1), $Sp^4$ is absent (i.e. i is 0) and $Sp^1$ is present (i.e. c is b), $Z^2$ connects D or $Q^2$ to spacer moiety $Sp^1$ of the linker according to formula (2). In the compound according to formula (2), when b, e and i are all 0, then D or $Q^2$ is attached directly to BM of the linker according to formula (2).

As will be understood by the person skilled in the art, the nature of a connecting group depends on the type of organic reaction with which the connection between the specific parts of said compound was obtained. A large number of organic reactions are available for connecting a reactive group $Q^1$ to a spacer moiety, and for connecting a target molecule to a spacer-moiety. Consequently, there is a large variety of connecting groups $Z^1$ and $Z^2$.

In a preferred embodiment of the linker according to formula (2), $Z^1$ and $Z^2$ are independently selected from the group consisting of —O—, —S—, —S—S—, —NR$^2$—, —N=N—, —C(O)—, —C(O)—NR$^2$—, —O—C(O)—, —O—C(O)—O—, —O—C(O)—NR$^2$, —NR$_2$—C(O)—, —NR$^2$—C(O)—O—, —NR$^2$—C(O)—NR$^2$—, —S—C(O)—, —S—C(O)—O—, —S—C(O)—NR$^2$—, —S(O)—, —S(O)$_2$—, —O—S(O)$_2$—, —O—S(O)$_2$—O—, —O—S(O)$_2$—NR$^2$—, —O—S(O)—, —O—S(O)—O—, —O—S(O)—NR$^2$—, —O—NR$^2$—C(O)—, —O—NR$^2$—C(O)—O—, —O—NR$^2$—C(O)—NR$^2$—, —NR$^2$—O—C(O)—, —NR$^2$—O—C(O)—O—, —NR$^2$—O—C(O)—NR$^2$—, —ONR$^2$—C(S)—, —O—NR$^2$—C(S)—O—, —O—NR$^2$—C(S)—NR$^2$—, —NR$^2$—O—C(S)—, —NR$^2$—O—C(S)—O—, —NR$^2$—O—C(S)—NR$^2$—, —O—C(S)—, —O—C(S)—O—, —O—C(S)—NR$^2$—, —NR$^2$—C(S)—, —NR$^2$—C(S)—O—, —NR$^2$—C(S)—NR$^2$—, —S—S(O)$_2$—, —S—S(O)$_2$—O—, —S—S(O)$_2$—NR$^2$—, —NR$^2$—O—S(O)—, —NR$^2$—O—S(O)—O—, —NR$^2$—O—S(O)—NR$^2$—, —NR$^2$—O—S(O)$_2$—, —NR$^2$—O—S(O)$_2$—O—, —NR$^2$—O—S(O)$_2$—NR$^2$—, —O—NR$^2$—S(O)$_2$—O—, —O—NR$^2$—S(O)—, —O—NR$^2$—S(O)—O—, —O—NR$^2$—S(O)—NR$^2$—, —O—NR$^2$—S(O)$_2$—O—, —O—NR$^2$—S(O)$_2$—NR$^2$—, —O—NR$^2$—S(O)$_2$—, —O—P(O)(R$^2$)$_2$—, —S—P(O)(R$^2$)$_2$—, —NR$^2$—P(O)(R$^2$)$_2$— and combinations of two or more thereof, wherein $R^2$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

As described above, in the compound according to formula (2), $Sp^1$, $Sp^2$, $Sp^3$, $Sp^4$, $Sp^5$ and $Sp^6$ are spacer-moieties. $Sp^1$, $Sp^2$, $Sp^3$, $Sp^4$, $Sp^5$ and $Sp^6$ may be, independently, absent or present (b, c, g, i, k and l are, independently, 0 or 1). Each spacer, if present, may be different from any other spacer, if present.

Spacer-moieties are known to a person skilled in the art. Examples of suitable spacer-moieties include (poly)ethylene glycol diamines (e.g. 1,8-diamino-3,6-dioxaoctane or equivalents comprising longer ethylene glycol chains), polyethylene glycol chains or polyethylene oxide chains, polypropylene glycol chains or polypropylene oxide chains and 1,x-diaminoalkanes wherein x is the number of carbon atoms in the alkane. Another class of suitable spacer-moieties comprises cleavable spacer-moieties, or cleavable linkers. Cleavable linkers are well known in the art. For example Shabat et al. *Soft Matter* 2012, 6, 1073, incorporated by reference herein, discloses cleavable linkers comprising self-immolative moieties that are released upon a biological trigger, e.g. an enzymatic cleavage or an oxidation event. Some examples of suitable cleavable linkers are disulfide-linkers that are cleaved upon reduction, peptide-linkers that are cleaved upon specific recognition by a protease, e.g. cathepsin, plasmin or metalloproteases, or glycoside-based linkers that are cleaved upon specific recognition by a glycosidase, e.g. glucoronidase, or nitroaromatics that are reduced in oxygen-poor, hypoxic areas. Herein, suitable cleavable spacer-moieties also include spacer moieties comprising a specific, cleavable, sequence of amino acids. Examples include e.g. spacer-moieties comprising a Val-Ala (valine-alanine) or Val-Cit (valine-citrulline) moiety. Bioconjugates containing a cleavable linker, such as Val-Cit linker, in particular Val-Cit-PABC, suffer considerably from aggregation in view of their limited water-solubility. For such bioconjugates, incorporating the sulfamide linker according to the invention is particularly beneficial. Also, conjugation reactions with a linker comprising a cleavable linker are hampered by the limited water-solubility of the linker. Hence, linker comprising a cleavable linker, such as Val-Cit linker, in particular Val-Cit-PABC, and the sulfamide linker according to the invention outperform linkers comprising such a cleavable linker but lacking such sulfamide linker in conjugation to biomolecules. Thus, in a preferred embodiment of the linker according to formula (2), spacer moieties $Sp^1$, $Sp^2$, $Sp^3$, $Sp^4$, $Sp^5$ and/or $Sp^6$, if present, comprise a sequence of amino acids. Spacer-moieties comprising a sequence of amino acids are known in the art, and may also be referred to as peptide linkers. Examples include spacer-moieties comprising a Val-Cit moiety, e.g. Val-Cit-PABC, Val-Cit-PABC, Fmoc-Val-Cit-PABC, etc. Preferably, a Val-Cit-PABC moiety is employed in the linker.

In a preferred embodiment of the linker according to formula (2), spacer moieties $Sp^1$, $Sp^2$, $Sp^3$, $Sp^4$, $Sp^5$ and $Sp^6$, if present, are independently selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups and $C_9$-$C_{200}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and NR$^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. When the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are interrupted by one or more heteroatoms as defined above, it is preferred that said groups are interrupted by one or more O-atoms, and/or by one or more S—S groups.

More preferably, spacer moieties $Sp^1$, $Sp^2$, $Sp^3$, $Sp^4$, $Sp^5$ and $Sp^6$, if present, are independently selected from the group consisting of linear or branched $C_1$-$C_{100}$ alkylene groups, $C_2$-$C_{100}$ alkenylene groups, $C_2$-$C_{100}$ alkynylene groups, $C_3$-$C_{100}$ cycloalkylene groups, $C_5$-$C_{100}$ cycloalkenylene groups, $C_5$-$C_{100}$ cycloalkynylene groups, $C_7$-$C_{100}$ alkylarylene groups, $C_7$-$C_{100}$ arylalkylene groups, $C_5$-$C_{100}$ arylalkenylene groups and $C_9$-$C_{100}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Even more preferably, spacer moieties $Sp^1$, $Sp^2$, $Sp^3$, $Sp^4$, $Sp^5$ and $Sp^6$, if present, are independently selected from the group consisting of linear or branched $C_1$-$C_{50}$ alkylene groups, $C_2$-$C_{50}$ alkenylene groups, $C_2$-$C_{50}$ alkynylene groups, $C_3$-$C_{50}$ cycloalkylene groups, $C_5$-$C_{50}$ cycloalkenylene groups, $C_8$-$C_{50}$ cycloalkynylene groups, $C_7$-$C_{50}$ alkylarylene groups, $C_7$-$C_{50}$ arylalkylene groups, $C_8$-$C_{50}$ arylalkenylene groups and $C_9$-$C_{50}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Yet even more preferably, spacer moieties $Sp^1$, $Sp^2$, $Sp^3$, $Sp^4$, $Sp^5$ and $Sp^6$, if present, are independently selected from the group consisting of linear or branched $C_1$-$C_{20}$ alkylene groups, $C_2$-$C_{20}$ alkenylene groups, $C_2$-$C_{20}$ alkynylene groups, $C_3$-$C_{20}$ cycloalkylene groups, $C_5$-$C_{20}$ cycloalkenylene groups, $C_8$-$C_{20}$ cycloalkynylene groups, $C_7$-$C_{20}$ alkylarylene groups, $C_7$-$C_{20}$ arylalkylene groups, $C_8$-$C_{20}$ arylalkenylene groups and $C_9$-$C_{20}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

In these preferred embodiments it is further preferred that the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are unsubstituted and optionally interrupted by one or more heteroatoms selected from the group of O, S and $NR^3$, preferably O, wherein $R^3$ is independently selected from the group consisting of hydrogen and $C_1$-$C_4$ alkyl groups, preferably hydrogen or methyl.

Most preferably, spacer moieties $Sp^1$, $Sp^2$, $Sp^3$, $Sp^4$, $Sp^5$ and $Sp^6$, if present, are independently selected from the group consisting of linear or branched $C_1$-$C_{20}$ alkylene groups, the alkylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. In this embodiment, it is further preferred that the alkylene groups are unsubstituted and optionally interrupted by one or more heteroatoms selected from the group of O, S and $NR^3$, preferably O and/or or S—S, wherein $R^3$ is independently selected from the group consisting of hydrogen and $C_1$-$C_4$ alkyl groups, preferably hydrogen or methyl.

Preferred spacer moieties $Sp^1$, $Sp^2$, $Sp^3$, $Sp^4$, $Sp^5$ and $Sp^6$ thus include —$(CH_2)_n$—, —$(CH_2CH_2)_n$—, —$(CH_2CH_2O)_n$—, —$(OCH_2CH_2)_n$—, —$(CH_2CH_2CO)_nCH_2CH_2$—, —$CH_2CH_2(OCH_2CH_2)_n$—, —$(CH_2CH_2CH_2O)_n$—, —$(OCH_2CH_2CH_2)_n$—, —$(CH_2CH_2CH_2CO)_nCH_2CH_2CH_2$— and —$CH_2CH_2CH_2(OCH_2CH_2CH_2)_n$—, wherein n is an integer in the range of 1 to 50, preferably in the range of 1 to 40, more preferably in the range of 1 to 30, even more preferably in the range of 1 to 20 and yet even more preferably in the range of 1 to 15. More preferably n is 1, 2, 3, 4, 5, 6, 7, 8, 9 or 10, more preferably 1, 2, 3, 4, 5, 6, 7 or 8, even more preferably 1, 2, 3, 4, 5 or 6, yet even more preferably 1, 2, 3 or 4.

Since $Sp^1$, $Sp^2$, $Sp^3$, $Sp^4$, $Sp^5$ and $Sp^6$ are independently selected, $Sp^1$, if present, may be different from $Sp^2$, if present, which may be different from $Sp^3$, if present, which may be different from $Sp^4$, if present, which may be different from $Sp^5$, if present, which may be different from $Sp^6$, if present.

As described above, $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is D, -[$(Sp^1)_b$-$(Z^2)_e$-$(Sp^4)_i$-D] or -[$(Sp^2)_c$-$(Z^1)_d$-$(Sp^3)_g$-$Q^1$], wherein $Sp^1$, $Sp^2$, $Sp^3$, $Sp^4$, $Z^1$, $Z^2$, D, $Q^1$, b, c, d, e, g and i are as defined above.

In a preferred embodiment, $R^1$ is hydrogen or a $C_1$-$C_{20}$ alkyl group, more preferably $R^1$ is hydrogen or a $C_1$-$C_{16}$ alkyl group, even more preferably $R^1$ is hydrogen or a $C_1$-$C_{10}$ alkyl group, wherein the alkyl group is optionally substituted and optionally interrupted by one or more heteroatoms selected from O, S and $NR^3$, preferably O, wherein $R^3$ is independently selected from the group consisting of hydrogen and $C_1$-$C_4$ alkyl groups. In a further preferred embodiment, $R^1$ is hydrogen. In another further preferred embodiment, $R^1$ is a $C_1$-$C_{20}$ alkyl group, more preferably a $C_1$-$C_{16}$ alkyl group, even more preferably a $C_1$-$C_{10}$ alkyl group, wherein the alkyl group is optionally interrupted by one or more O-atoms, and wherein the alkyl group is optionally substituted with an —OH group, preferably a terminal —OH group. In this embodiment it is further preferred that $R^1$ is a polyethylene glycol chain comprising a terminal —OH group. In another further preferred embodiment, $R^1$ is a $C_1$-$C_{12}$ alkyl group, more preferably a $C_1$-$C_6$ alkyl group, even more preferably a $C_1$-$C_4$ alkyl group, and yet even more preferably $R^1$ is selected from the group consisting of methyl, ethyl, n-propyl, i-propyl, n-butyl, s-butyl and t-butyl.

In another preferred embodiment, $R^1$ is a target molecule D, -[($Sp^1$)$_b$-($Z^2$)$_e$-($Sp^4$)$_i$-D] or -[($Sp^2$)$_c$-($Z^1$)$_d$-($Sp^3$)$_g$-$Q^1$], wherein $Sp^1$, $Sp^2$, $Sp^3$, $Sp^4$, $Z^1$, $Z^2$, D, $Q^1$, b, c, d, e, g and i are as defined above.

In the linker according to formula (2), f is an integer in the range of 1 to 10, preferably 1-5. The linker may thus comprise more than one group according to formula (1), the group according to formula (1) being as defined above. When more than one group according to formula (1) is present, i.e. When f is 2 or more, then BM, b, $Sp^1$, $Sp^5$, k, SG $Sp^6$, l and E are independently selected. In other words, when f is 2 or more, each b is independently 0 or 1, each k is independently 0 or 1, each l is independently 0 or 1, each $Sp^1$ may be the same or different, each $Sp^5$ may be the same or different, each $Sp^6$ may be the same or different each SG may be the same or different and each E may be the same or different, f is 1, 2, 3, 4, 5, 6, 7, 8, 9 or 10, preferably f is 1, 2, 3, 4, or 5, even more preferably f is 1, 2, 3 or 4, even more preferably f is 1, 2 or 3, even more preferably f is 1 or 2, and most preferably f is 1 in this embodiment. In another preferred embodiment, f is an integer in the range of 2 to 10, i.e. f is 2, 3, 4, 5, 6, 7, 8, 9 or 10, preferably f is 2, 3, 4 or 5, more preferably f is 2, 3 or 4, even more preferably f is 2 or 3, and most preferably f is 2 in this embodiment.

These preferred embodiments of the linker of structure (2) also hold for the linker-moiety in linker-conjugates, linker-constructs and bioconjugates according to the invention as described in more detail below.

Linker-Conjugate

In the context of the present invention, "linker-conjugate" refers to the target molecule D which is functionalized with a linker according to the invention, comprising a branching moiety BM and a sulfamide group SG, which further bears a reactive group $Q^1$. In other words, the linker-conjugate is a compound wherein a target molecule is covalently connected to a reactive group $Q^1$, via a linker. In a first aspect, the invention concerns linker-conjugates as defined herein. The linker-conjugate according to the invention comprises the linker according to the invention as defined above, preferably the linker according to structure (2).

The linker-conjugate according to the invention may comprise more than one target molecule D. Similarly, the linker-conjugate may comprise more than one reactive group $Q^1$. When more than one reactive group $Q^1$ is present the groups $Q^1$ may be the same or different, and when more than one target molecule D is present the target molecules D may be the same or different. The linker-conjugate according to the invention may therefore also be denoted as $(Q^1)_y$-Sp-$(D)_z$, wherein y is an integer in the range of 1 to 10 and z is an integer in the range of 1 to 10. The invention thus also relates to a compound according to the formula: $(Q^1)_y$-Sp-$(D)_z$, wherein:

y is an integer in the range of 1 to 10, preferably in the range 1-5, more preferably y=1;

z is an integer in the range of 1 to 10, preferably in the range 1-5;

$Q^1$ is a reactive group capable of reacting with a functional group $F^1$ present on a biomolecule;

D is a target molecule;

Sp is a spacer moiety, wherein a spacer moiety is defined as a moiety that spaces (i.e. provides a certain distance between) and covalently links reactive group $Q^1$ and target molecule D, wherein said spacer moiety comprises the linker according to the invention as defined above.

Preferably, y is 1, 2, 3 or 4, more preferably y is 1 or 2 and most preferably, y is 1. Preferably, z is 1, 2, 3, 4, 5 or 6, more preferably z is 1, 2, 3 or 4, even more preferably z is 1, 2 or 3, yet even more preferably z is 1 or 2 and most preferably z is 1. More preferably, y is 1 or 2, preferably 1, and z is 1, 2, 3 or 4, yet even more preferably y is 1 or 2, preferably 1, and z is 1, 2 or 3, yet even more preferably y is 1 or 2, preferably 1, and z is 1 or 2, and most preferably y is 1 and z is 1. In a preferred embodiment, the linker-conjugate is according to the formula $Q^1$-Sp-$(D)_4$, $Q^1$-Sp-$(D)_3$, $Q^1$-Sp-$(D)_2$ or $Q^1$-Sp-D.

Target Molecule D

Target molecules in the field of bioconjugation are known to the skilled person, and may also be referred to as payload. In a preferred embodiment of the linker-conjugate according to the invention, the target molecule is selected from the group consisting of an active substance, a reporter molecule, a polymer, a solid surface, a hydrogel, a nanoparticle, a microparticle and a biomolecule. The inventors found that the use of a sulfamide linker according to the invention improves the solubility of the linker-conjugate, which in turn significantly improves the efficiency of the conjugation. Using conventional linkers, effective conjugation is often hampered by the relatively low solubility of the linker-conjugate in aqueous media, especially when a relative water-insoluble or hydrophobic target molecule is used. In a particularly preferred embodiment, the target molecule in its unconjugated form is hydrophobic, typically having a water solubility of at most 1% (w/w), preferably at most 0.1% (w/w), most preferably at most 0.01% (w/w), determined at 20° C. and 100 kPa. Even such water-insoluble target molecules are effectively subjected to conjugation when functionalized with a sulfamide linker according to the invention. Herein, the "unconjugated form" refers to the target molecule not being functionalized with or conjugated to the linker according to the invention. Such unconjugated forms of target molecules are known to the skilled person.

The term "active substance" herein relates to a pharmacological and/or biological substance, i.e. a substance that is biologically and/or pharmaceutically active, for example a drug, a prodrug, a diagnostic agent, a protein, a peptide, a polypeptide, a peptide tag, an amino acid, a glycan, a lipid, a vitamin, a steroid, a nucleotide, a nucleoside, a polynucleotide, RNA or DNA. Examples of peptide tags include cell-penetrating peptides like human lactoferrin or polyarginine. An example of a glycan is oligomannose. An example of an amino acid is lysine.

When the target molecule is an active substance, the active substance is preferably selected from the group consisting of drugs and prodrugs. More preferably, the active substance is selected from the group consisting of pharmaceutically active compounds, in particular low to medium molecular weight compounds (e.g. about 200 to about 2500 Da, preferably about 300 to about 1750 Da). In a further preferred embodiment, the active substance is selected from the group consisting of cytotoxins, antiviral agents, antibacterials agents, peptides and oligonucleotides. Examples of cytotoxins include colchicine, vinca alkaloids, anthracyclines, camptothecins, doxorubicin, daunorubicin, taxanes, calicheamycins, tubulysins, irinotecans, an inhibitory peptide, amanitin, deBouganin, duocarmycins, maytansines, auristatins or pyrrolobenzodiazepines (PBDs). In view of their poor water solubility, preferred active substances include vinca alkaloids, anthracyclines, camptothecins, taxanes, tubulysins, amanitin, duocarmycins, maytansines, auristatins and pyrrolobenzodiazepines, in particular vinca alkaloids, anthracyclines, camptothecins, taxanes, tubulysins, amanitin, maytansines and auristatins.

The term "reporter molecule" herein refers to a molecule whose presence is readily detected, for example a diagnostic agent, a dye, a fluorophore, a radioactive isotope label, a contrast agent, a magnetic resonance imaging agent or a mass label.

A wide variety of fluorophores, also referred to as fluorescent probes, is known to a person skilled in the art. Several fluorophores are described in more detail in e.g. G. T. Hermanson, "*Bioconjugate Techniques*", Elsevier, 3$^{rd}$ Ed. 2013, Chapter 10: "Fluorescent probes", p. 395-463, incorporated by reference. Examples of a fluorophore include all kinds of Alexa Fluor (e.g. Alexa Fluor 555), cyanine dyes (e.g. Cy3 or Cy5) and cyanine dye derivatives, coumarin derivatives, fluorescein and fluorescein derivatives, rhodamine and rhodamine derivatives, boron dipyrromethene derivatives, pyrene derivatives, naphthalimide derivatives, phycobiliprotein derivatives (e.g. allophycocyanin), chromomycin, lanthanide chelates and quantum dot nanocrystals. In view of their poor water solubility, preferred fluorophores include cyanine dyes, coumarin derivatives, fluorescein and derivatives thereof, pyrene derivatives, naphthalimide derivatives, chromomycin, lanthanide chelates and quantum dot nanocrystals, in particular coumarin derivatives, fluorescein, pyrene derivatives and chromomycin.

Examples of a radioactive isotope label include $^{99m}$Tc, $^{111}$In, $^{114m}$In, $^{115}$In, $^{18}$F, $^{14}$C, $^{64}$Cu, $^{131}$I, $^{125}$I, $^{123}$I, $^{212}$Bi, $^{88}$Y, $^{90}$Y, $^{67}$Cu, $^{186}$Rh, $^{188}$Rh, $^{66}$Ga, $^{67}$Ga and $^{10}$B, which is optionally connected via a chelating moiety such as e.g. DTPA (diethylenetriaminepentaacetic anhydride), DOTA (1,4,7,10-tetraazacyclododecane-N,N',N'',N'''-tetraacetic acid), NOTA (1,4,7-triazacyclononane N,N',N''-triacetic acid), TETA (1,4,8,11-tetraazacyclotetradecane-N,N',N'', N'''-tetraacetic acid), DTTA (N$^1$-(p-isothiocyanatobenzyl)-diethylenetriamine-N$^1$,N$^2$,N$^3$-tetraacetic acid), deferoxamine or DFA (N'-[5-[[4-[[5-(acetylhydroxyamino)pentyl]amino]-1,4-dioxobutyl]hydroxyamino]pentyl]-N-(5-aminopentyl)-N-hydroxybutanediamide) or HYNIC (hydrazinonicotinamide). Isotopic labelling techniques are known to a person skilled in the art, and are described in more detail in e.g. G. T. Hermanson, "*Bioconjugate Techniques*", Elsevier, 3$^{rd}$ Ed. 2013, Chapter 12: "Isotopic labelling techniques", p. 507-534, incorporated by reference.

Polymers suitable for use as a target molecule D in the compound according to the invention are known to a person skilled in the art, and several examples are described in more detail in e.g. G. T. Hermanson, "*Bioconjugate Techniques*", Elsevier, 3$^{rd}$ Ed. 2013, Chapter 18: "PEGylation and synthetic polymer modification", p. 787-838, incorporated by reference. When target molecule D is a polymer, target molecule D is preferably independently selected from the group consisting of a polyethylene glycol) (PEG), a polyethylene oxide (PEO), a polypropylene glycol (PPG), a polypropylene oxide (PPO), a 1,x-diaminoalkane polymer (wherein x is the number of carbon atoms in the alkane, and preferably x is an integer in the range of 2 to 200, preferably 2 to 10), a (poly)ethylene glycol diamine (e.g. 1,8-diamino-3,6-dioxaoctane and equivalents comprising longer ethylene glycol chains), a polysaccharide (e.g. dextran), a poly(amino acid) (e.g. a poly(L-lysine)) and a poly(vinyl alcohol). In view of their poor water solubility, preferred polymers include a 1,x-diaminoalkane polymer and poly(vinyl alcohol).

Solid surfaces suitable for use as a target molecule D are known to a person skilled in the art. A solid surface is for example a functional surface (e.g. a surface of a nanomaterial, a carbon nanotube, a fullerene or a virus capsid), a metal surface (e.g. a titanium, gold, silver, copper, nickel, tin, rhodium or zinc surface), a metal alloy surface (wherein the alloy is from e.g. aluminium, bismuth, chromium, cobalt, copper, gallium, gold, indium, iron, lead, magnesium, mercury, nickel, potassium, plutonium, rhodium, scandium, silver, sodium, titanium, tin, uranium, zinc and/or zirconium), a polymer surface (wherein the polymer is e.g. polystyrene, polyvinylchloride, polyethylene, polypropylene, poly(dimethylsiloxane) or poly(methylmethacrylate), poly(acrylamide)), a glass surface, a silicone surface, a chromatography support surface (wherein the chromatography support is e.g. a silica support, an agarose support, a cellulose support or an alumina support), etc. When target molecule D is a solid surface, it is preferred that D is independently selected from the group consisting of a functional surface or a polymer surface.

Hydrogels are known to the person skilled in the art. Hydrogels are water-swollen networks, formed by cross-links between the polymeric constituents. See for example A. S. Hoffman, *Adv. Drug Delivery Rev.* 2012, 64, 18, incorporated by reference. When the target molecule is a hydrogel, it is preferred that the hydrogel is composed of poly(ethylene)glycol (PEG) as the polymeric basis.

Micro- and nanoparticles suitable for use as a target molecule D are known to a person skilled in the art. A variety of suitable micro- and nanoparticles is described in e.g. G. T. Hermanson, "*Bioconjugate Techniques*", Elsevier, 3$^{rd}$ Ed. 2013, Chapter 14: "Microparticles and nanoparticles", p. 549-587, incorporated by reference. The micro- or nanoparticles may be of any shape, e.g. spheres, rods, tubes, cubes, triangles and cones. Preferably, the micro- or nanoparticles are of a spherical shape. The chemical composition of the micro- and nanoparticles may vary. When target molecule D is a micro- or a nanoparticle, the micro- or nanoparticle is for example a polymeric micro- or nanoparticle, a silica micro- or nanoparticle or a gold micro- or nanoparticle. When the particle is a polymeric micro- or nanoparticle, the polymer is preferably polystyrene or a copolymer of styrene (e.g. a copolymer of styrene and divinylbenzene, butadiene, acrylate and/or vinyltoluene), poly(methylmethacrylate) (PMMA), poly(vinyltoluene), poly(hydroxyethyl methacrylate) p(HEMA) or polyethylene glycol dimethacrylate/2-hydroxyethylmethacrylate) p(EDGMA/HEMA). Optionally, the surface of the micro- or nanoparticles is modified, e.g. with detergents, by graft polymerization of secondary polymers or by covalent attachment of another polymer or of spacer moieties, etc.

Target molecule D may also be a biomolecule. Biomolecules, and preferred embodiments thereof, are described in more detail below. When target molecule D is a biomolecule, it is preferred that the biomolecule is selected from the group consisting of proteins (including glycoproteins and antibodies), polypeptides, peptides, glycans, lipids, nucleic acids, oligonucleotides, polysaccharides, oligosaccharides, enzymes, hormones, amino acids and monosaccharides.

Reactive Moiety Q$^1$

The linker-conjugate according to the invention comprises a reactive group Q$^1$ that is capable of reacting with a functional group F$^1$ present on a biomolecule. Functional groups are known to a person skilled in the art and may be defined as any molecular entity that imparts a specific property onto the molecule harbouring it. For example, a functional group in a biomolecule may constitute an amino group, a thiol group, a carboxylic acid, an alcohol group, a carbonyl group, a phosphate group, or an aromatic group. The functional group in the biomolecule may be naturally present or may be placed in the biomolecule by a specific technique, for example a (bio)chemical or a genetic technique. The functional group that is placed in the biomolecule may be a functional group that is naturally present in nature, or may be a functional group that is prepared by chemical synthesis, for example an azide, a terminal alkyne or a phosphine moiety. Herein, the term "reactive group" may refer to a certain group that comprises a functional group, but also to a functional group itself. For example, a cyclooctynyl group is a reactive group comprising a functional group, namely a C—C triple bond. Similarly, an N-maleimidyl group is a reactive group, comprising a C—C double bond as a functional group. However, a functional group, for example an azido functional group, a thiol functional group or an amino functional group, may herein also be referred to as a reactive group. The linker-conjugate may comprise more than one reactive group $Q^1$. When the linker-conjugate comprises two or more reactive groups $Q^1$, the reactive groups $Q^1$ may differ from each other. Preferably, the linker-conjugate comprises one reactive group $Q^1$.

Reactive group $Q^1$ that is present in the linker-conjugate, is able to react with a functional group $F^1$ that is present in a biomolecule. In other words, reactive group $Q^1$ needs to be complementary to a functional group $F^1$ present in a biomolecule. Herein, a reactive group is denoted as "complementary" to a functional group when said reactive group reacts with said functional group selectively, optionally in the presence of other functional groups. Complementary reactive and functional groups are known to a person skilled in the art, and are described in more detail below. Preferably, reactive group $Q^1$ and functional group $F^1$ are capable of reacting in a bioorthogonal reaction, as those reactions do not interfere with the biomolecules present during this reaction. Bioorthogonal reactions and functional groups suitable therein are known to the skilled person, for example from Gong and Pan, *Tetrahedron Lett.* 2015, 56, 2123-2132, and include Staudinger ligations and copper-free Click chemistry. It is thus preferred that $Q^1$ is selected from the group consisting of 1,3-dipoles, alkynes, (hetero)cyclooctynes, cyclooctenes, tetrazines, ketones, aldehydes, alkoxyamines, hydrazines and triphenylphosphine. In a preferred embodiment, reactive group $Q^1$ is selected from the group consisting of, optionally substituted, N-maleimidyl groups, halogenated N-alkylamido groups, sulfonyloxy N-alkylamido groups, ester groups, carbonate groups, sulfonyl halide groups, thiol groups or derivatives thereof, alkenyl groups, alkynyl groups, (hetero)cycloalkynyl groups, bicyclo[6.1.0]non-4-yn-9-yl] groups, cycloalkenyl groups, tetrazinyl groups, azido groups, phosphine groups, nitrile oxide groups, nitrone groups, nitrile imine groups, diazo groups, ketone groups, (O-alkyl)hydroxylamino groups, hydrazine groups, halogenated N-maleimidyl groups, 1,1-bis(sulfonylmethyl)methylcarbonyl groups or elimination derivatives thereof, carbonyl halide groups, allenamide groups, 1,2-quinone groups or triazine groups.

In a preferred embodiment, $Q^1$ is an N-maleimidyl group. When $Q^1$ is an N-maleimidyl group, $Q^1$ is preferably unsubstituted. $Q^1$ is thus preferably according to formula (9a), as shown below. Suitable maleimidyl moieties include diaminopropionyl maleimdyl moieties. A preferred example of such a maleimidyl group is 2,3-diaminopropionic acid (DPR) maleimidyl, which may be connected to the remainder of the linker-conjugate through the carboxylic acid moiety or the remaining amine moiety. In another preferred embodiment, $Q^1$ is a halogenated N-alkylamido group. When $Q^1$ is a halogenated N-alkylamido group, it is preferred that $Q^1$ is according to formula (9b), as shown below, wherein k is an integer in the range of 1 to 10 and $R^4$ is selected from the group consisting of —Cl, —Br and —I. Preferably k is 1, 2, 3 or 4, more preferably k is 1 or 2 and most preferably k is 1. Preferably, $R^4$ is —I or —Br. More preferably, k is 1 or 2 and $R^4$ is —I or —Br, and most preferably k is 1 and $R^4$ is —I or Br.

In another preferred embodiment, $Q^1$ is a sulfonyloxy N-alkylamido group. When $Q^1$ is a sulfonyloxy N-alkylamido group, it is preferred that $Q^1$ is according to formula (9b), as shown below, wherein k is an integer in the range of 1 to 10 and $R^4$ is selected from the group consisting of —O-mesyl, —O-phenylsulfonyl and —O-tosyl. Preferably k is 1, 2, 3 or 4, more preferably k is 1 or 2, even more preferably k is 1. Most preferably k is 1 and $R^4$ is selected from the group consisting of —O-mesyl, —O-phenylsulfonyl and —O-tosyl.

In another preferred embodiment, $Q^1$ is an ester group. When $Q^1$ is an ester group, it is preferred that the ester group is an activated ester group. Activated ester groups are known to the person skilled in the art. An activated ester group is herein defined as an ester group comprising a good leaving group, wherein the ester carbonyl group is bonded to said good leaving group. Good leaving groups are known to the person skilled in the art. It is further preferred that the activated ester is according to formula (9c), as shown below, wherein $R^5$ is selected from the group consisting of —N-succinimidyl (NHS), —N-sulfo-succinimidyl (sulfo-NHS), -(4-nitrophenyl), -pentafluorophenyl or -tetrafluorophenyl (TFP).

In another preferred embodiment, $Q^1$ is a carbonate group. When $Q^1$ is a carbonate group, it is preferred that the carbonate group is an activated carbonate group. Activated carbonate groups are known to a person skilled in the art. An activated carbonate group is herein defined as a carbonate group comprising a good leaving group, wherein the carbonate carbonyl group is bonded to said good leaving group. It is further preferred that the carbonate group is according to formula (9d), as shown below, wherein $R^7$ is selected from the group consisting of —N-succinimidyl, —N-sulfo-succinimidyl, -(4-nitrophenyl), -pentafluorophenyl or -tetrafluorophenyl.

In another preferred embodiment, $Q^1$ is a sulfonyl halide group according to formula (9e) as shown below, wherein X is selected from the group consisting of F, Cl, Br and I. Preferably X is Cl or Br, more preferably Cl.

In another preferred embodiment, $Q^1$ is a thiol group (9f), or a derivative or a precursor of a thiol group. A thiol group may also be referred to as a mercapto group. When $Q^1$ is a derivative or a precursor of a thiol group, the thiol derivative is preferably according to formula (9g), (9h) or (9zb) as shown below, wherein $R^8$ is an, optionally substituted, $C_1$-$C_{12}$ alkyl group or a $C_2$-$C_{12}$ (hetero)aryl group, V is O or S and $R^{16}$ is an, optionally substituted, $C_1$-$C_{12}$ alkyl group. More preferably $R^8$ is an, optionally substituted, $C_1$-$C_6$ alkyl group or a $C_2$-$C_6$ (hetero)aryl group, and even more preferably $R^8$ is methyl, ethyl, n-propyl, i-propyl, n-butyl, s-butyl, t-butyl or phenyl. Even more preferably, $R^8$ is methyl or phenyl, most preferably methyl. More preferably $R^{16}$ is an optionally substituted $C_1$-$C_6$ alkyl group, and even more preferably $R^{16}$ is methyl, ethyl, n-propyl, i-propyl, n-butyl, s-butyl or t-butyl, most preferably methyl. When $Q^1$ is a thiol-derivative according to formula (9g) or (9zb), and $Q^1$ is reacted with a reactive group $F^1$ on a biomolecule, said thiol-derivative needs to be converted into a thiol group during the process. When $Q^1$ is according to formula (9h), $Q^1$ is —SC(O)OR$^8$ or —SC(S)OR$^8$, preferably SC(O)OR$^8$, wherein R$^8$, and preferred embodiments thereof, are as defined above.

In another preferred embodiment, $Q^1$ is an alkenyl group, wherein the alkenyl group is linear or branched, and wherein the alkenyl group is optionally substituted. The alkenyl group may be a terminal or an internal alkenyl group. The alkenyl group may comprise more than one C—C double bond, and if so, preferably comprises two C—C double bonds. When the alkenyl group is a dienyl group, it is further preferred that the two C—C double bonds are separated by one C—C single bond (i.e. it is preferred that the dienyl group is a conjugated dienyl group). Preferably said alkenyl group is a $C_2$-$C_{24}$ alkenyl group, more preferably a $C_2$-$C_{12}$ alkenyl group, and even more preferably a $C_2$-$C_6$ alkenyl group. It is further preferred that the alkenyl group is a terminal alkenyl group. More preferably, the alkenyl group is according to formula (9i) as shown below, wherein l is an integer in the range of 0 to 10, preferably in the range of 0 to 6, and p is an integer in the range of 0 to 10, preferably 0 to 6. More preferably, l is 0, 1, 2, 3 or 4, more preferably l is 0, 1 or 2 and most preferably l is 0 or 1. More preferably, p is 0, 1, 2, 3 or 4, more preferably p is 0, 1 or 2 and most preferably p is 0 or 1. It is particularly preferred that p is 0 and l is 0 or 1, or that p is 1 and l is 0 or 1.

In another preferred embodiment, $Q^1$ is an alkynyl group, wherein the alkynyl group is linear or branched, and wherein the alkynyl group is optionally substituted. The alkynyl group may be a terminal or an internal alkynyl group. Preferably said alkynyl group is a $C_2$-$C_{24}$ alkynyl group, more preferably a $C_2$-$C_{12}$ alkynyl group, and even more preferably a $C_2$-$C_6$ alkynyl group. It is further preferred that the alkynyl group is a terminal alkynyl group. More preferably, the alkynyl group is according to formula (9j) as shown below, wherein l is an integer in the range of 0 to 10, preferably in the range of 0 to 6. More preferably, l is 0, 1, 2, 3 or 4, more preferably l is 0, 1 or 2 and most preferably l is 0 or 1.

In another preferred embodiment, $Q^1$ is a cycloalkenyl group. The cycloalkenyl group is optionally substituted. Preferably said cycloalkenyl group is a $C_3$-$C_{24}$ cycloalkenyl group, more preferably a $C_3$-$C_{12}$ cycloalkenyl group, and even more preferably a $C_3$-$C_8$ cycloalkenyl group. In a preferred embodiment, the cycloalkenyl group is a trans-cycloalkenyl group, more preferably a trans-cyclooctenyl group (also referred to as a TCO group) and most preferably a trans-cyclooctenyl group according to formula (9zi) or (9zj) as shown below. In another preferred embodiment, the cycloalkenyl group is a cyclopropenyl group, wherein the cyclopropenyl group is optionally substituted. In another preferred embodiment, the cycloalkenyl group is a norbornenyl group, an oxanorbornenyl group, a norbornadienyl group or an oxanorbornadienyl group, wherein the norbornenyl group, oxanorbornenyl group, norbornadienyl group or an oxanorbornadienyl group is optionally substituted. In a further preferred embodiment, the cycloalkenyl group is according to formula (9k), (9l), (9m) or (9zc) as shown below, wherein T is CH$_2$ or O, R$^9$ is independently selected from the group consisting of hydrogen, a linear or branched $C_1$-$C_{12}$ alkyl group or a $C_4$-$C_{12}$ (hetero)aryl group, and R$^{19}$ is selected from the group consisting of hydrogen and fluorinated hydrocarbons. Preferably, R$^9$ is independently hydrogen or a $C_1$-$C_6$ alkyl group, more preferably R$^9$ is independently hydrogen or a $C_1$-$C_4$ alkyl group. Even more preferably R$^9$ is independently hydrogen or methyl, ethyl, n-propyl, i-propyl, n-butyl, s-butyl ort-butyl. Yet even more preferably R$^9$ is independently hydrogen or methyl. In a further preferred embodiment, R$^{19}$ is selected from the group of hydrogen and —CF$_3$, —C$_2$F$_5$, —C$_3$F$_7$ and —C$_4$F9, more preferably hydrogen and —CF$_3$. In a further preferred embodiment, the cycloalkenyl group is according to formula (9k), wherein one R$^9$ is hydrogen and the other R$_9$ is a methyl group. In another further preferred embodiment, the cycloalkenyl group is according to formula (9l), wherein both R$^9$ are hydrogen. In these embodiments it is further preferred that l is 0 or 1. In another further preferred embodiment, the cycloalkenyl group is a norbornenyl (T is CH$_2$) or an oxanorbornenyl (T is O) group according to formula (9m), or a norbornadienyl (T is CH$_2$) or an oxanorbornadienyl (T is O) group according to formula (9zc), wherein R$^9$ is hydrogen and R$^{19}$ is hydrogen or —CF$_3$, preferably —CF$_3$.

In another preferred embodiment, $Q^1$ is a (hetero)cycloalkynyl group. The (hetero)cycloalkynyl group is optionally substituted. Preferably, the (hetero)cycloalkynyl group is a (hetero)cyclooctynyl group, i.e. a heterocyclooctynyl group or a cyclooctynyl group, wherein the (hetero)cyclooctynyl group is optionally substituted. In a further preferred embodiment, the (hetero)cyclooctynyl group is according to formula (9n), also referred to as a DIBO group, (9o), also referred to as a DIBAC group or (9p), also referred to as a BARAC group, or (9zk), also referred to as a COMBO group, all as shown below, wherein U is O or NR$^9$, and preferred embodiments of R$^9$ are as defined above. The aromatic rings in (9n) are optionally O-sulfonylated at one or more positions, whereas the rings of (9o) and (9p) may be halogenated at one or more positions.

In an especially preferred embodiment, the nitrogen atom attached to R$^1$ in compound (4b) is the nitrogen atom in the ring of the heterocycloalkyne group such as the nitrogen atom in (9o). In other words, c, d and g are 0 in compound (4b) and R$^1$ and $Q^1$, together with the nitrogen atom they are attached to, form a heterocycloalkyne group, preferably a heterocyclooctyne group, most preferably the heterocyclooctyne group according to formula (9o) or (9p). Herein, the carbonyl moiety of (9o) is replaced by the sulfonyl group of the group according to formula (1). Alternatively, the nitrogen atom to which R$^1$ is attached is the same atom as the atom designated as U in formula (9n). In other words, when $Q^1$ is according to formula (9n), U may be the right nitrogen atom of the group according to formula (1), or U=NR$^9$ and R$^9$ is the remainder of the group according to formula (1) and R$^1$ is the cyclooctyne moiety.

In another preferred embodiment, $Q^1$ is an, optionally substituted, bicyclo[6.1.0]non-4-yn-9-yl] group, also referred to as a BCN group. Preferably, the bicyclo[6.1.0] non-4-yn-9-yl] group is according to formula (9q) as shown below.

In another preferred embodiment, $Q^1$ is a conjugated (hetero)diene group capable of reacting in a Diels-Alder reaction. Preferred (hetero)diene groups include optionally substituted tetrazinyl groups, optionally substituted 1,2-quinone groups and optionally substituted triazine groups. More preferably, said tetrazinyl group is according to formula (9r), as shown below, wherein R$^9$ is selected from the group consisting of hydrogen, a linear or branched $C_1$-$C_{12}$ alkyl group or a $C_4$-$C_{12}$ (hetero)aryl group. Preferably, R$^9$ is hydrogen, a $C_1$-$C_6$ alkyl group or a $C_4$-$C_{10}$ (hetero)aryl group, more preferably R$^9$ is hydrogen, a $C_1$-$C_4$ alkyl group or a $C_4$-$C_6$ (hetero)aryl group. Even more preferably R$^9$ is hydrogen, methyl, ethyl, n-propyl, i-propyl, n-butyl, s-butyl, t-butyl or pyridyl. Yet even more preferably R$^9$ is hydrogen, methyl or pyridyl. More preferably, said 1,2-quinone group is according to formula (9zl) or (9zm). Said triazine group may be any regioisomer. More preferably, said triazine group is a 1,2,3-triazine group or a 1,2,4-triazine group, which may be attached via any possible location, such as indicated in formula (9zn). The 1,2,3-triazine is most preferred as triazine group.

In another preferred embodiment, $Q^1$ is an azido group according to formula (9s) as shown below. In another preferred embodiment, $Q^1$ is an, optionally substituted, triarylphosphine group that is suitable to undergo a Staudinger ligation reaction. Preferably, the phosphine group is according to formula (9t) as shown below, wherein $R^{10}$ is a (thio)ester group. When $R^{10}$ is a (thio)ester group, it is preferred that $R^{10}$ is —C(O)—V—$R^{11}$, wherein V is O or S and $R^{11}$ is a $C_1$-$C_{12}$ alkyl group. Preferably, $R^{11}$ is a $C_1$-$C_6$ alkyl group, more preferably a $C_1$-$C_4$ alkyl group. Most preferably, $R^{11}$ is a methyl group.

In another preferred embodiment, $Q^1$ is a nitrile oxide group according to formula (9u) as shown below.

In another preferred embodiment, $Q^1$ is a nitrone group. Preferably, the nitrone group is according to formula (9v) as shown below, wherein $R^{12}$ is selected from the group consisting of linear or branched $C_1$-$C_{12}$ alkyl groups and $C_6$-$C_{12}$ aryl groups. Preferably, $R^{12}$ is a $C_1$-$C_6$ alkyl group, more preferably $R^{12}$ is a $C_1$-$C_4$ alkyl group. Even more preferably $R^{12}$ is methyl, ethyl, n-propyl, i-propyl, n-butyl, s-butyl ort-butyl. Yet even more preferably $R^{12}$ is methyl.

In another preferred embodiment, $Q^1$ is a nitrile imine group. Preferably, the nitrile imine group is according to formula (9w) or (9zd) as shown below, wherein $R^{13}$ is selected from the group consisting of linear or branched $C_1$-$C_{12}$ alkyl groups and $C_6$-$C_{12}$ aryl groups. Preferably, $R^{13}$ is a $C_1$-$C_6$ alkyl group, more preferably $R^{13}$ is a $C_1$-$C_4$ alkyl group. Even more preferably $R^{13}$ is methyl, ethyl, n-propyl, i-propyl, n-butyl, s-butyl ort-butyl. Yet even more preferably $R^{13}$ is methyl.

In another preferred embodiment, $Q^1$ is a diazo group. Preferably, the diazo group is according to formula (9x) as shown below, wherein $R^{14}$ is selected from the group consisting of hydrogen or a carbonyl derivative. More preferably, $R^{14}$ is hydrogen.

In another preferred embodiment, $Q^1$ is a ketone group. More preferably, the ketone group is according to formula (9y) as shown below, wherein $R^{15}$ is selected from the group consisting of linear or branched $C_1$-$C_{12}$ alkyl groups and $C_6$-$C_{12}$ aryl groups. Preferably, $R^{15}$ is a $C_1$-$C_6$ alkyl group, more preferably $R^{15}$ is a $C_1$-$C_4$ alkyl group. Even more preferably $R^{15}$ is methyl, ethyl, n-propyl, i-propyl, n-butyl, s-butyl ort-butyl. Yet even more preferably $R^{15}$ is methyl.

In another preferred embodiment, $Q^1$ is an (O-alkyl) hydroxylamino group. More preferably, the (O-alkyl)hydroxylamino group is according to formula (9z) as shown below.

In another preferred embodiment, $Q^1$ is a hydrazine group. Preferably, the hydrazine group is according to formula (9za) as shown below.

In another preferred embodiment, $Q^1$ is a halogenated N-maleimidyl group or a sulfonylated N-maleimidyl group. When $Q^1$ is a halogenated or sulfonylated N-maleimidyl group, $Q^1$ is preferably according to formula (9ze) as shown below, wherein $R^6$ is independently selected from the group consisting of hydrogen F, Cl, Br, I, —$SR^{18a}$ and —$OS(O)_2 R^{18b}$, wherein $R^{18a}$ is an optionally substituted $C_4$-$C_{12}$ (hetero)aryl groups, preferably phenyl or pyrydyl, and $R^{18b}$ is selected from the group consisting of, optionally substituted, $C_1$-$C_{12}$ alkyl groups and $C_4$-$C_{12}$ (hetero)aryl groups, preferably tolyl or methyl, and with the proviso that at least one $R^6$ is not hydrogen. When $R^6$ is halogen (i.e. when $R^6$ is F, Cl, Br or I), it is preferred that $R^6$ is Br. In one embodiment, the halogenated N-maleimidyl group is halogenated 2,3-diaminopropionic acid (DPR) maleimidyl, which may be connected to the remainder of the linker-conjugate through the carboxylic acid moiety or the remaining amine moiety.

In another preferred embodiment, $Q^1$ is a carbonyl halide group according to formula (9zf) as shown below, wherein X is selected from the group consisting of F, Cl, Br and I. Preferably, X is Cl or Br, and most preferably, X is Cl.

In another preferred embodiment, $Q^1$ is an allenamide group according to formula (9zg).

In another preferred embodiment, $Q^1$ is a 1,1-bis(sulfonylmethyl)methylcarbonyl group according to formula (9zh), or an elimination derivative thereof, wherein $R^{18}$ is selected from the group consisting of, optionally substituted, $C_1$-$C_{12}$ alkyl groups and $C_4$-$C_{12}$ (hetero)aryl groups. More preferably, $R^{18}$ is an, optionally substituted, $C_1$-$C_6$ alkyl group or a $C_4$-$C_6$ (hetero)aryl group, and most preferably a phenyl group.

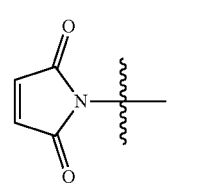

9a

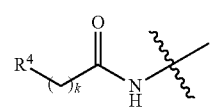

9b

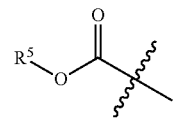

9c

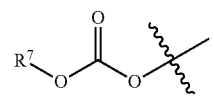

9d

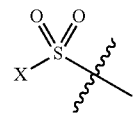

9e

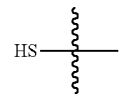

9f

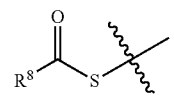

9g

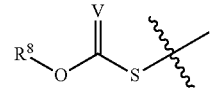

9h

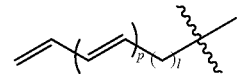

9i

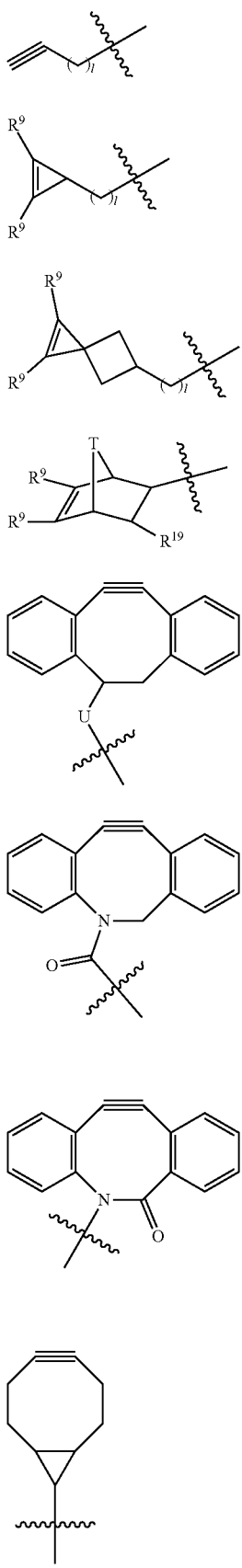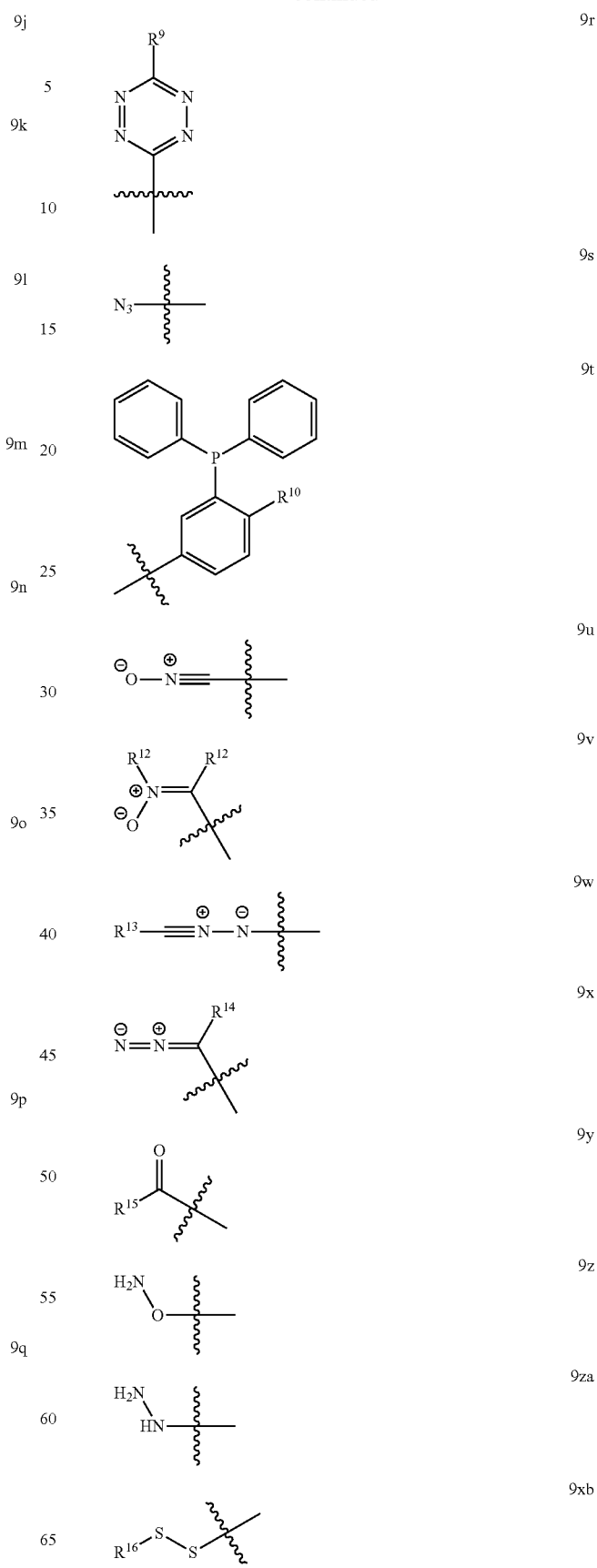

-continued

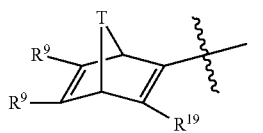
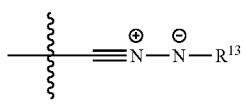
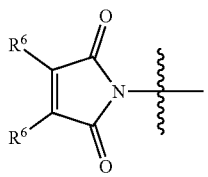
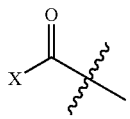
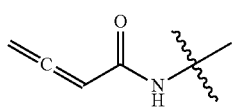
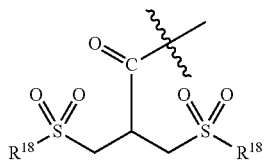
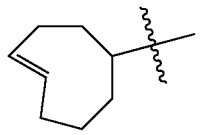
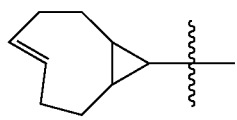
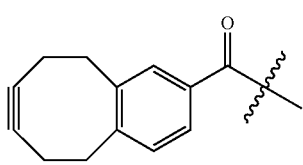
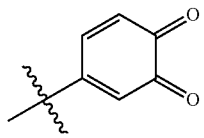
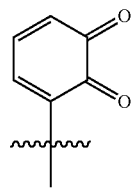

-continued

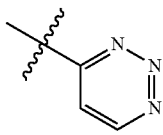

wherein k, l, X, T, U, V, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are as defined above.

In a preferred embodiment of the conjugation process according to the invention as described hereinbelow, conjugation is accomplished via a cycloaddition, such as a Diels-Alder reaction or a 1,3-dipolar cycloaddition, preferably the 1,3-dipolar cycloaddition. According to this embodiment, the reactive group $Q^1$ (as well as $F^1$ on the biomolecule) is selected from groups reactive in a cycloaddition reaction. Herein, reactive groups $Q^1$ and $F^1$ are complementary, i.e. they are capable of reacting with each other in a cycloaddition reaction.

For a Diels-Alder reaction, one of $F^1$ and $Q^1$ is a diene and the other of $F^1$ and $Q^1$ is a dienophile. As appreciated by the skilled person, the term "diene" in the context of the Diels-Alder reaction refers to 1,3-(hetero)dienes, and includes conjugated dienes ($R_2C=CR-CR=CR_2$), imines (e.g. $R_2C=CR-N=CR_2$ or $R_2C=CR-CR=NR$, $R_2C=N-N=CR_2$) and carbonyls (e.g. $R_2C=CR-CR=O$ or $O=CR-CR=O$). Hetero-Diels-Alder reactions with N- and O-containing dienes are known in the art. Any diene known in the art to be suitable for Diels-Alder reactions may be used as reactive group $Q^1$ or $F^1$. Preferred dienes include tetrazines as described above, 1,2-quinones as described above and triazines as described above. Although any dienophile known in the art to be suitable for Diels-Alder reactions may be used as reactive groups $Q^1$ or $F^1$, the dienophile is preferably an alkene or alkyne group as described above, most preferably an alkyne group. For conjugation via a Diels-Alder reaction, it is preferred that $F^1$ is the diene and $Q^1$ is the dienophile. Herein, when $Q^1$ is a diene, $F^1$ is a dienophile and when $Q^1$ is a dienophile, $F^1$ is a diene. Most preferably, $Q^1$ is a dienophile, preferably $Q^1$ is or comprises an alkynyl group, and $F^1$ is a diene, preferably a tetrazine, 1,2-quinone or triazine group.

For a 1,3-dipolar cycloaddition, one of $F^1$ and $Q^1$ is a 1,3-dipole and the other of $F^1$ and $Q^1$ is a dipolarophile. Any 1,3-dipole known in the art to be suitable for 1,3-dipolar cycloadditions may be used as reactive group $Q^1$ or $F^1$. Preferred 1,3-dipoles include azido groups, nitrone groups, nitrile oxide groups, nitrile imine groups and diazo groups. Although any dipolarophile known in the art to be suitable for 1,3-dipolar cycloadditions may be used as reactive groups $Q^1$ or $F^1$, the dipolarophile is preferably an alkene or alkyne group, most preferably an alkyne group. For conjugation via a 1,3-dipolar cycloaddition, it is preferred that $F^1$ is the 1,3-dipole and $Q^1$ is the dipolarophile. Herein, when $Q^1$ is a 1,3-dipole, $F^1$ is a dipolarophile and when $Q^1$ is a dipolarophile, $F^1$ is a 1,3-dipole. Most preferably, $Q^1$ is a dipolarophile, preferably $Q^1$ is or comprises an alkynyl group, and $F^1$ is a 1,3-dipole, preferably an azido group.

Thus, in a preferred embodiment, $Q^1$ is selected from dipolarophiles and dienophiles. Preferably, $Q^1$ is an alkene or an alkyne group. In an especially preferred embodiment, $Q^1$ comprises an alkyne group, preferably selected from the alkynyl group as described above, the cycloalkenyl group as described above, the (hetero)cycloalkynyl group as described above and a bicyclo[6.1.0]non-4-yn-9-yl] group, more preferably $Q^1$ is selected from the formulae (9j), (9n), (9o), (9p), (9q) and (9zk), as defined above and depicted below, more preferably selected from the formulae (9n), (9o), (9p), (9q) and (9zk). Most preferably, $Q^1$ is a bicyclo[6.1.0]non-4-yn-9-yl] group, preferably of formula (9q). These groups are known to be highly effective in the conjugation with azido-functionalized biomolecules as described herein, and when the sulfamide linker according to the invention is employed in such linker-conjugates and bioconjugates, any aggregation is beneficially reduced to a minimum. The sulfamide linker according to the invention provides a significant reduction in aggregation especially for such hydrophobic reactive groups of $Q^1$, and for the conjugated bioconjugates.

Figure 6:
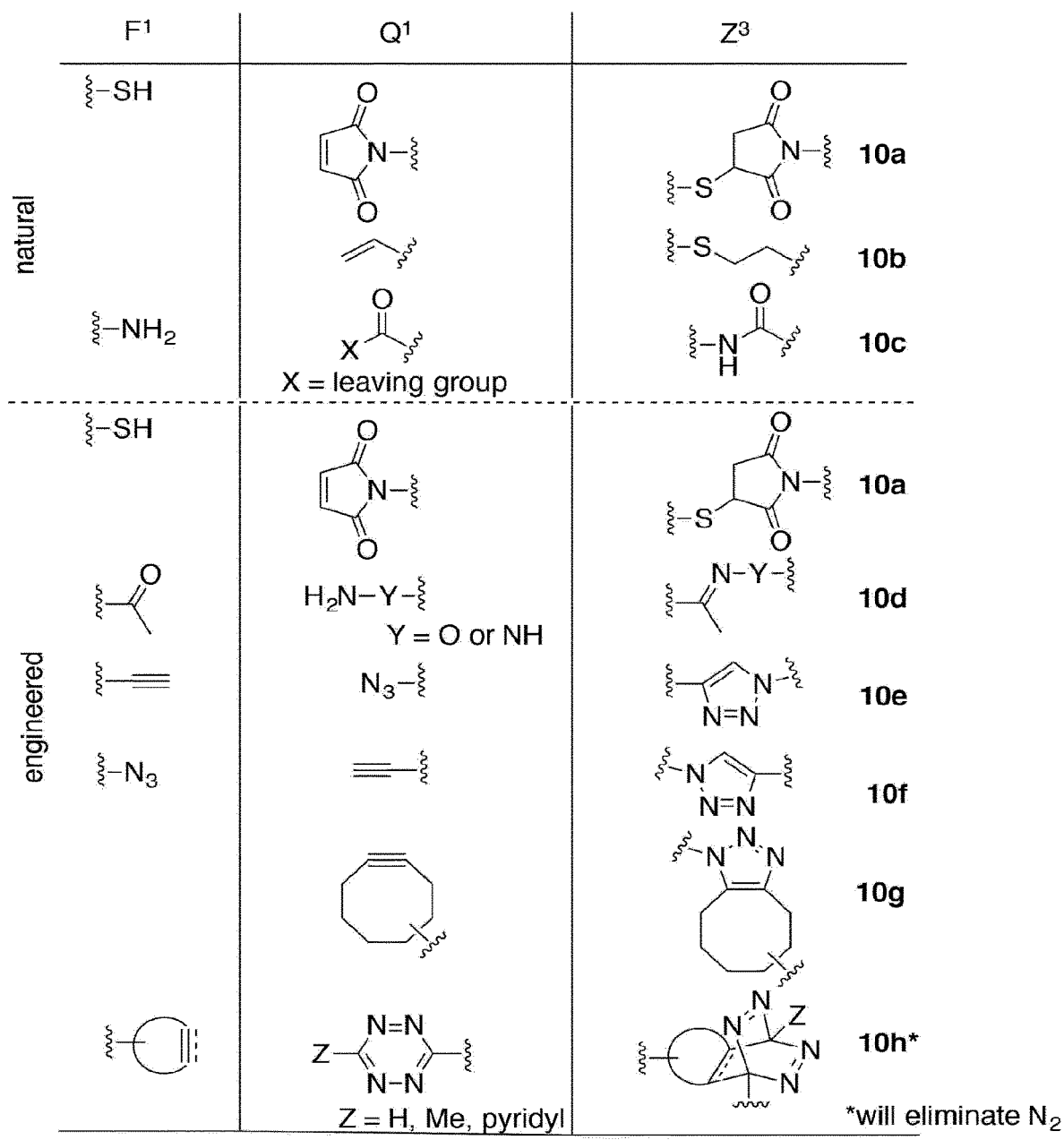
FIG. 6 shows a representative set of functional groups ($F^1$) in a biomolecule, either naturally present or introduced by engineering, which upon reaction with reactive group $Q^1$ lead to connecting group $Z^3$. Functional group $F^1$ may also be artificially introduced (engineered) into a biomolecule at any position of choice. The same functional groups and reactive moieties are suitably used as $F^2$ and $Q^2$, respectively. Connecting group $Z^3$ may also be the result of a reaction between $F^2$ and $Q^2$.

As was described above, in the compound according to the invention, $Q^1$ is capable of reacting with a reactive group $F^1$ that is present on a biomolecule. Complementary reactive groups $F^1$ for reactive group $Q^1$ are known to a person skilled in the art, and are described in more detail below. Some representative examples of reaction between $F^1$ and $Q^1$ and their corresponding products are depicted in FIG. 6.

As described above, D and $Q^1$ are covalently attached in the linker-conjugate according to the invention, via the linker as defined above. Covalent attachment of D to the linker may occur for example via reaction of a functional group $F^2$ present on D with a reactive group $Q^2$ present on the linker. Suitable organic reactions for the attachment of D to a linker are known to a person skilled in the art, as are functional groups $F^2$ that are complementary to a reactive group $Q^2$. Consequently, D may be attached to the linker via a connecting group Z.

The term "connecting group" herein refers to the structural element, e.g. resulting from the reaction between Q and F, connecting one part of a compound and another part of the same compound. As will be understood by the person skilled in the art, the nature of a connecting group depends on the type of organic reaction with which the connection between the parts of said compound was obtained. As an example, when the carboxyl group of R—C(O)—OH is reacted with the amino group of $H_2N$—R' to form R—C(O)—N(H)—R', R is connected to R' via connecting group Z, and Z may be represented by the group —C(O)—N(H)—.

Reactive group $Q^1$ may be attached to the linker in a similar manner. Consequently, $Q^1$ may be attached to the spacer-moiety via a connecting group Z.

Numerous reactions are known in the art for the attachment of an active substance to a linker, and for the attachment of a reactive group $Q^1$ to a linker. Consequently, a wide variety of connecting groups Z may be present in the first precursor. In one embodiment, the reactive group $Q^2$ is selected from the options for reactive group $Q^1$ and preferred embodiments thereof, as defined hereinabove, preferably as depicted in FIG. 6. Complementary functional groups $F^2$ and the thus obtained connecting groups Z are known to a person skilled in the art and disclosed herein.

Preferred Linker-Conjugates

The linker-conjugate according to the invention may also be represented by the formula:

$(Q^1)_y$-$(Z^w)$-Sp-$(Z^x)$-$(D)_z$ wherein:
y is an integer in the range of 1 to 10, preferably in the range 1-5, more preferably y=1;
z is an integer in the range of 1 to 10, preferably in the range 1-5;
$Q^1$ is a reactive group as defined hereinabove;
D is a target molecule as defined hereinabove;

Sp is a spacer moiety, wherein a spacer moiety is defined as a moiety that spaces (i.e. provides a certain distance between) and covalently links reactive group $Q^1$ and target molecule D, wherein said spacer moiety comprises the linker according to the invention as defined above;
$Z^w$ is a connecting group connecting reactive group $Q^1$ to said spacer moiety; and
$Z^x$ is a connecting group connecting target molecule D to said spacer moiety.

Preferred embodiments for y and z are as defined above for $(Q^1)_y$-Sp-$(D)_z$. Preferred embodiments for D and $Q^1$ are as defined above. It is further preferred that the compound is according to the formula $Q^1$-$(Z^w)$-Sp-$(Z^x)$-$(D)_4$, $Q^1$-$(Z^w)$-Sp-$(Z^x)$-$(D)_3$, $Q^1$-$(Z^w)$-Sp-$(Z^x)$-$(D)_2$ or $Q^1$-$(Z^w)$-Sp-$(Z^x)$-D, more preferably $Q^1$-$(Z^w)$-Sp-$(Z^x)$-$(D)_2$ or $Q^1$-$(Z^w)$-Sp-$(Z^x)$-D and most preferably $Q^1$-$(Z^w)$-Sp-$(Z^x)$-D, wherein $Z^w$ and $Z^x$ are as defined above.

Preferably, $Z^w$ and $Z^x$ are independently selected from the group consisting of —O—, —S—, —$NR^2$—, —N=N—, —C(O)—, —C(O)—$NR^2$—, —O—C(O)—, —O—C(O)—O—, —O—C(O)—$NR^2$, —$NR_2$—C(O)—, —$NR^2$—C(O)—O—, —$NR^2$—C(O)—$NR^2$—, —S—C(O)—, —S—C(O)—O—, —S—C(O)—$NR^2$—, —S(O)—, —S(O)$_2$—, —O—S(O)$_2$—, —O—S(O)$_2$—O—, —O—S(O)$_2$—$NR^2$—, —O—S(O)—, —O—S(O)—O—, —O—S(O)—$NR^2$—, —O—$NR^2$—C(O)—, —O—$NR^2$—C(O)—O—, —O—$NR^2$—C(O)—$NR^2$—, —$NR^2$—O—C(O)—, —$NR^2$—O—C(O)—O—, —$NR^2$—O—C(O)—$NR^2$—, —O—$NR^2$—C(S)—, —O—$NR^2$—C(S)—O—, —O—$NR^2$—C(S)—$NR^2$—, —$NR^2$—O—C(S)—, —$NR^2$—O—C(S)—O—, —$NR^2$—O—C(S)—$NR^2$—, —O—C(S)—, —O—C(S)—O—, —O—C(S)—$NR^2$—, —$NR^2$—C(S)—, —$NR^2$—C(S)—O—, —$NR^2$—C(S)—$NR^2$—, —S—S(O)$_2$—, —S—S(O)$_2$—O—, —S—S(O)$_2$—$NR^2$—, —$NR^2$—O—S(O)—, —$NR^2$—O—S(O)—O—, —$NR^2$—O—S(O)—$NR^2$—, —$NR^2$—O—S(O)$_2$—, —$NR^2$—O—S(O)$_2$—O—, —$NR^2$—O—S(O)$_2$—$NR^2$—, —O—$NR^2$—S(O)—, —O—$NR^2$—S(O)—O—, —O—$NR^2$—S(O)—$NR^2$—, —O—$NR^2$—S(O)$_2$—O—, —O—$NR^2$—S(O)$_2$—$NR^2$—, —O—$NR^2$—S(O)$_2$—, —O—P(O)$(R^2)_2$—, —S—P(O)$(R^2)_2$—, —$NR^2$—P(O)$(R^2)_2$— and combinations of two or more thereof, wherein $R^2$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

The linker-conjugate according to the invention may also be represented by formula (4):

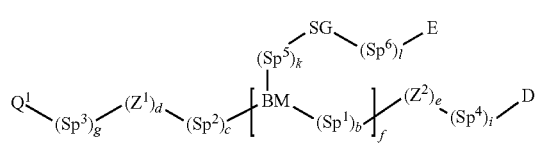

(4)

Herein:
BM is a branching moiety as defined above;
E is a capping group as defined above;
SG is a sulfamide group according to formula (1), wherein a and $R^1$ are as defined above;
D is a target molecule as defined above;
$Q^1$ is a reactive group as defined above;

b is independently 0 or 1;
c is 0 or 1;
d is 0 or 1;
e is 0 or 1;
f is an integer in the range of 1 to 10;
g is 0 or 1;
i is 0 or 1;
k is 0 or 1;
l is 0 or 1;
$Sp^1$ is a spacer moiety;
$Sp^2$ is a spacer moiety;
$Sp^3$ is a spacer moiety;
$Sp^4$ is a spacer moiety;
$Sp^5$ is a spacer moiety;
$Sp^6$ is a spacer moiety;
$Z^1$ is a connecting group that connects $Q^1$ or $Sp^3$ to $Sp^2$ or BM; and
$Z^2$ is a connecting group that connects D or $Sp^4$ to $Sp^1$ or BM.

Definitions and preferred embodiments for each of BM, E, SG, b, c, d, e, f, g, i, k, l, $Sp^1$, $Sp^2$, $Sp^3$, $Sp^4$, $Sp^5$, $Sp^6$, $Z^1$ and $Z^2$ are given above for the linker, and also apply to the linker-conjugate according to structure (4). Definitions and preferred embodiments for each of $Q^1$ and BM are given above, and also apply to the linker-conjugate according to structure (4).

Especially preferred linker-conjugates are represented by the structures by any of the structures (34)-(39):

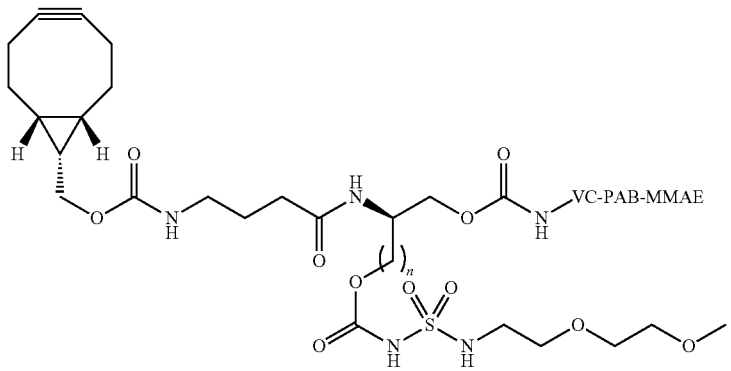

(34)

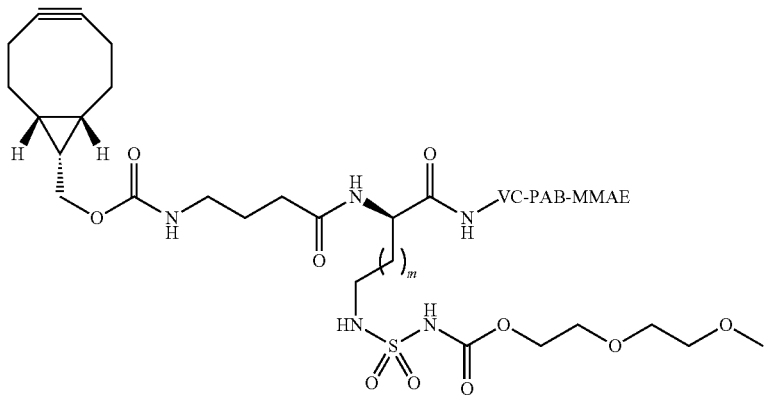

(35)

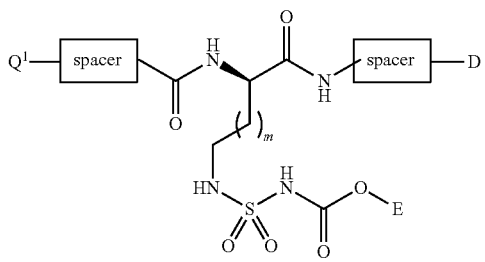

(36)

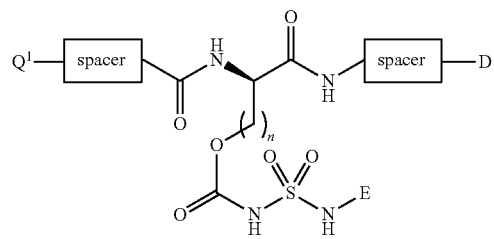

(37)

(38)

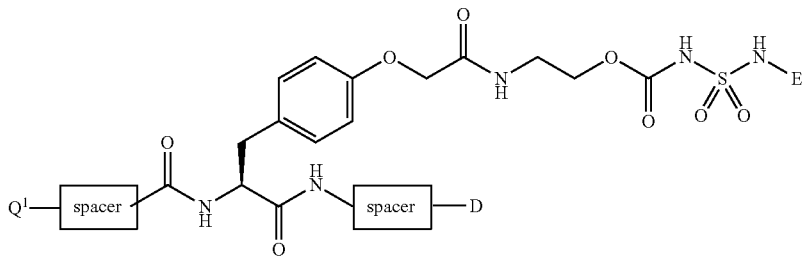

(39)

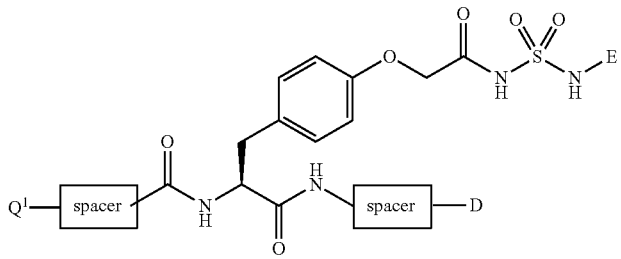

In structures (34)-(39), n and m are individually 0-20, preferably 0-5, most preferably 0 or 1, and $Q^1$, D and E are as defined above. In one embodiment, the linker-conjugate is represented by structure (34), wherein n=0 (corresponding to compound 32 as prepared in Example 9).

The invention further concerns the use of a linker-conjugate according to the invention for the preparation of a bioconjugate according to the invention. Such a process for the preparation is typically referred to as "bioconjugation" or a "bioconjugation reaction", and is further defined below.

Linker-Construct

In the context of the present invention, "linker-construct" refers to a compound wherein a reactive group $Q^1$ is covalently connected to a reactive group $Q^2$ via a linker according to the invention, comprising a branching moiety BM and a sulfamide group SG. In other words, the linker-construct is a compound wherein a reactive group $Q^2$ is covalently connected to a reactive group $Q^1$, via a linker. In a second aspect, the invention concerns linker-constructs as defined herein. The linker-construct according to the invention comprises the linker according to the invention as defined above, preferably the linker according to structure (2).

A linker-construct comprises a reactive group $Q^1$ capable of reacting with a reactive group $F^1$ present on a biomolecule, and a reactive group $Q^2$ capable of reacting with a reactive group $F^2$ present on a target molecule. $Q^1$ and $Q^2$ may be the same, or different. A linker-construct may comprise more than one reactive group $Q^1$ and/or more than one reactive group $Q^2$. When more than one reactive groups $Q^1$ are present the groups $Q^1$ may be the same or different, and when more than one reactive groups $Q^2$ are present the groups $Q^2$ may be the same or different.

The linker-construct according to the invention may be denoted as $(Q^1)_y$-Sp-$(Q^2)_z$, wherein y is an integer in the range of 1 to 10 and z is an integer in the range of 1 to 10.

The invention thus also relates to a linker-construct according to the formula $(Q^1)_y$-Sp-$(Q^2)_z$, wherein:
- y is an integer in the range of 1 to 10, preferably in the range 1-5, more preferably y=1;
- z is an integer in the range of 1 to 10, preferably in the range 1-5;
- $Q^1$ is a reactive group as defined hereinabove;
- $Q^2$ is a reactive group capable of reacting with a functional group $F^2$ present on a target molecule;
- Sp is a spacer moiety, wherein a spacer moiety is defined as a moiety that spaces (i.e. provides a certain distance between) and covalently links reactive group $Q^1$ and target molecule $Q^2$, wherein said spacer moiety comprises the linker according to the invention as defined above.

Preferably, y is 1, 2, 3 or 4, more preferably y is 1 or 2 and most preferably, y is 1. Preferably, z is 1, 2, 3, 4, 5 or 6, more preferably z is 1, 2, 3 or 4, even more preferably z is 1, 2 or 3, yet even more preferably z is 1 or 2 and most preferably z is 1. More preferably, y is 1 or 2, preferably 1, and z is 1, 2, 3 or 4, yet even more preferably y is 1 or 2, preferably 1, and z is 1, 2 or 3, yet even more preferably y is 1 or 2, preferably 1, and z is 1 or 2, and most preferably y is 1 and z is 1. In a preferred embodiment, the linker-construct is according to the formula $Q^1$-Sp-$(Q^2)_4$, $Q^1$-Sp-$(Q^2)_3$, $Q^1$-Sp-$(Q^2)_2$ or $Q^1$-Sp-$Q^2$.

More particular, the linker-construct according to the invention may be represented by the formula: $(Q^1)_y$-$(Z^w)$-Sp-$(Z^x)$-$(Q^2)_z$, wherein:
- y is an integer in the range of 1 to 10, preferably in the range 1-5, more preferably y=1;
- z is an integer in the range of 1 to 10, preferably in the range 1-5;
- $Q^1$ is a reactive group as defined hereinabove;
- $Q^2$ is a reactive group capable of reacting with a functional group $F^2$ present on a target molecule;
- Sp is a spacer moiety, wherein a spacer moiety is defined as a moiety that spaces (i.e. provides a certain distance between) and covalently links reactive group $Q^1$ and reactive group $Q^2$, wherein said spacer moiety comprises the linker according to the invention as defined above;
- $Z^w$ is a connecting group connecting reactive group $Q^1$ to said spacer moiety; and
- $Z^x$ is a connecting group connecting reactive group $Q^2$ to said spacer moiety.

Preferred embodiments for y and z are as defined above for $(Q^1)_y$-Sp-$(Q^2)_z$. It is further preferred that the compound is according to the formula $Q^1$-$(Z^w)$-Sp-$(Z^x)$-$(Q^2)_4$, $Q^1$-$(Z^w)$-

Sp-($Z^x$)-($Q^2$)$_3$, $Q^1$-($Z^w$)—Sp-($Z^x$)-($Q^2$)$_2$ or $Q^1$-($Z^w$)-Sp-($Z^x$)-$Q^2$, more preferably $Q^1$-($Z^w$)-Sp-($Z^x$)-($Q^2$)$_2$ or $Q^1$-($Z^w$)-Sp-($Z^x$)-$Q^2$ and most preferably $Q^1$-($Z^w$)-Sp-($Z^x$)-$Q^2$, wherein $Z^w$ and $Z^x$ are as defined above.

In the linker compound according to the invention, $Z^w$ and $Z^x$ are preferably independently selected from the group consisting of —O—, —S—, —NR$^2$—, —N=N—, —C(O)—, —C(O)—NR$^2$—, —O—C(O)—, —O—C(O)—O—, —O—C(O)—NR$^2$, —NR$_2$—C(O)—, —NR$^2$—C(O)—O—, —NR$^2$—C(O)—NR$^2$—, —S—C(O)—, —S—C(O)—O—, —S—C(O)—NR$^2$—, —S(O)—, —S(O)$_2$—, —O—S(O)$_2$—, —O—S(O)$_2$—O—, —O—S(O)$_2$—NR$^2$—, —O—S(O)—, —O—S(O)—O—, —O—S(O)—NR$^2$—, —O—NR$^2$—C(O)—, —O—NR$^2$—C(O)—O—, —O—NR$^2$—C(O)—NR$^2$—, —NR$^2$—O—C(O)—, —NR$^2$—O—C(O)—O—, —NR$^2$—O—C(O)—NR$^2$—, —O—NR$^2$—C(S)—, —O—NR$^2$—C(S)—O—, —O—NR$^2$—C(S)—NR$^2$—, —NR$^2$—O—C(S)—, —NR$^2$—O—C(S)—O—, —NR$^2$—O—C(S)—NR$^2$—, —O—C(S)—, —O—C(S)—O—, —O—C(S)—NR$^2$—, —NR$^2$—C(S)—, —NR$^2$—C(S)—O—, —NR$^2$—C(S)—NR$^2$—, —S—S(O)$_2$—, —S—S(O)$_2$—O—, —S—S(O)$_2$—NR$^2$—, —NR$^2$—O—S(O)—, —NR$^2$—O—S(O)—O—, —NR$^2$—O—S(O)—NR$^2$—, —NR$^2$—O—S(O)$_2$—, —NR$^2$—O—S(O)$_2$—O—, —NR$^2$—O—S(O)$_2$—NR$^2$—, —O—NR$^2$—S(O)—, —O—NR$^2$—S(O)—O—, —O—NR$^2$—S(O)—NR$^2$—, —O—NR$^2$—S(O)$_2$—O—, —O—NR$^2$—S(O)$_2$—NR$^2$—, —O—NR$^2$—S(O)$_2$—, —O—P(O)(R$^2$)$_2$—, —S—P(O)(R$^2$)$_2$—, —NR$^2$—P(O)(R$^2$)$_2$— and combinations of two or more thereof, wherein R$^2$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Preferred embodiments for $Q^1$ are as defined above for the linker-conjugate. In the linker-construct according to the invention, $Q^2$ is a reactive group capable of reacting with a functional group $F^2$ present on a target molecule. Reactive groups $Q^2$ capable of reacting with such a functional group $F^2$ are known to a person skilled in the art. In a preferred embodiment, $Q^2$ is a reactive group selected from the group consisting of, optionally substituted, N-maleimidyl groups, halogenated N-alkylamido groups, sulfonyloxy N-alkylamido groups, ester groups, carbonate groups, sulfonyl halide groups, thiol groups or derivatives thereof, alkenyl groups, alkynyl groups, (hetero)cycloalkynyl groups, bicyclo[6.1.0]non-4-yn-9-yl] groups, cycloalkenyl groups, tetrazinyl groups, azido groups, phosphine groups, nitrile oxide groups, nitrone groups, nitrile imine groups, diazo groups, ketone groups, (O-alkyl)hydroxylamino groups, hydrazine groups, halogenated N-maleimidyl groups, 1,1-bis(sulfonylmethyl)methylcarbonyl groups or elimination derivatives thereof, carbonyl halide groups and allenamide groups.

In a further preferred embodiment, $Q^2$ is according to formula (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zl), (9zm) or (9zn), wherein (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zl), (9zm), (9zn) and preferred embodiments thereof, are as defined above. In this embodiment it is further preferred that $Q^2$ is according to formula (9a), (9b), (9c), (9f), (9j), (9n), (9o), (9p), (9q), (9s), (9t), (9zh), (9r), (9zl), (9zm) or (9zn), more preferably according to formula (9a), (9n), (9o), (9p), (9q), (9t), (9zh) or (9s), and even more preferably $Q^2$ is according to formula (9a), (9p), (9q), (9n), (9t), (9zh), or (9o), and preferred embodiments thereof, as defined above. Most preferably, $Q^2$ is according to formula (9a), (9p), (9q), (9n), (9t), (9zh) or (9o), and preferred embodiments thereof, as defined above.

In a specific embodiment of the linker-construct according to the invention, $Q^1$ is according to formula (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zl), (9zm) or (9zn), wherein (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zl), (9zm), (9zn) and preferred embodiments thereof, are as defined above; and spacer moiety Sp is selected from the group consisting of linear or branched $C_1$-$C_{20}$ alkylene groups, the alkylene groups being optionally substituted and optionally interrupted by one or more heteroatoms selected from the group consisting of O, S and NR$^3$, wherein R$^3$ is independently selected from the group consisting of hydrogen and $C_1$-$C_4$ alkyl groups; wherein the spacer moiety Sp is interrupted by one or more branching moieties BM, connected to a sulfamide group SG and capping moiety E, optionally vie one or two spacers, as defined above.

In a further preferred embodiment, $Q^1$ is according to formula (9a), (9b), (9c), (9f), (9j), (9n), (9o), (9p), (9q), (9s), (9t), (9zh), (9zk), (9r), (9zl), (9zm) or (9zn). In an even further preferred embodiment, $Q^1$ is according to formula (9a), (9n), (9o), (9p), (9q), (9t), (9zh) or (9s), and in a particularly preferred embodiment, $Q^1$ is according to formula (9a), (9p), (9q), (9n), (9t), (9zh), (9zk) or (9o), and preferred embodiments thereof, as defined above. Most preferably $Q^1$ is according to formula (9a), (9p), (9q), (9n), (9t), (9zh) or (9o), and preferred embodiments thereof, as defined above.

The invention further concerns the use of a linker-construct according to the invention for the preparation of a linker-conjugate according to the invention. The process for preparing the linker-conjugate according to the invention is further defined below.

The invention further relates to the use of a linker-construct according to the invention in a bioconjugation process. The linker-construct according to the invention, and preferred embodiments therefore, are described in detail above.

Process for the Preparation of a Linker-Conjugate

The present invention also relates to a process for the preparation of a linker-conjugate according to the invention. In particular, the invention relates to a process for the preparation of a linker-conjugate according to the invention, the process comprising the step of reacting a functional group $Q^2$ of a linker-construct with a functional group $F^2$ of a target molecule, wherein said linker-construct is as defined above. The linker-construct and preferred embodiments thereof, including preferred embodiments of $Q^1$, $Q^2$ and target molecule D, are described in detail above. In a preferred embodiment of the process for the preparation of a linker-conjugate, the linker-construct is according to $(Q^1)_y$-Sp-$(Q^2)_z$ as defined above. In a further preferred embodiment of the process for the preparation of a linker-conjugate, the linker-construct is according to $(Q^1)_y$-($Z^w$)-Sp-($Z^x$)-$(Q^2)_z$ as defined above.

Bioconjugate

In a third aspect, the invention concerns bioconjugates as defined herein. In the context of the present invention, "bioconjugate" refers to a compound wherein a biomolecule is covalently connected to a target molecule via a linker according to the invention, comprising a branching moiety BM and a sulfamide group SG. In other words, the bioconjugate is a compound wherein a biomolecule is covalently connected to a target molecule, via a linker. A bioconjugate comprises one or more biomolecules and/or one or more target molecules. The bioconjugate according to the invention comprises the linker according to the invention as defined above, preferably the linker according to structure (2).

The bioconjugate according to the invention is typically prepared by the process for preparation of a bioconjugate according to the invention, wherein the linker-conjugate comprising reactive group $Q^1$ is conjugated to a biomolecule comprising reactive group $F^1$. In this conjugation reaction, reactive groups $Q^1$ and $F^1$ react with each other to form a connecting group $Z^3$, which joins the linker-conjugate with the biomolecule. All preferred embodiments described herein for the linker-conjugate and the linker thus equally apply to the bioconjugate according to the invention, except for all said for $Q^1$ and $F^1$, as the bioconjugate according to the invention contains the reaction product of $Q^1$ and $F^1$ as defined herein.

The bioconjugate according to the invention may comprise more than one target molecule. Similarly, the bioconjugate may comprise more than one biomolecule. Biomolecule B and target molecule D, and preferred embodiments thereof, are described in more detail above. Preferred embodiments for D in the bioconjugate according to the invention correspond to preferred embodiments of D in the linker-conjugate according to the invention as were described in more detail above. Preferred embodiments for the linker according to the invention as described above also apply to the linker comprised in the bioconjugate according to the invention.

In the bioconjugate according to the invention, biomolecule B is preferably selected from the group consisting of proteins (including glycoproteins and antibodies), polypeptides, peptides, glycans, lipids, nucleic acids, oligonucleotides, polysaccharides, oligosaccharides, enzymes, hormones, amino acids and monosaccharides. More preferably, biomolecule B is selected from the group consisting of proteins (including glycoproteins and antibodies), polypeptides, peptides, glycans, nucleic acids, oligonucleotides, polysaccharides, oligosaccharides and enzymes. Most preferably, biomolecule B is selected from the group consisting of proteins, including glycoproteins and antibodies, polypeptides, peptides and glycans.

The bioconjugate according to the invention may also be defined as a bioconjugate wherein a biomolecule is conjugated to a target molecule via a spacer-moiety, wherein the spacer-moiety comprises the linker according to the invention. The bioconjugate according to the invention may also be denoted as $(B)_y$-Sp-$(D)_z$, wherein y is an integer in the range of 1 to 10 and z is an integer in the range of 1 to 10. The invention thus also relates to a bioconjugate according to the formula: $(B)_y$-Sp-$(D)_z$, wherein:
y is an integer in the range of 1 to 10, preferably in the range 1-5, more preferably y=1;
z is an integer in the range of 1 to 10, preferably in the range 1-5;
B is a biomolecule as defined herein;
D is a target molecule as defined herein; and
Sp is a spacer moiety, wherein a spacer moiety is defined as a moiety that spaces (i.e. provides a certain distance between) and covalently links biomolecule B and target molecule D, wherein said spacer moiety comprises the linker according to the invention as defined above.

Preferably, y is 1, 2, 3 or 4, more preferably y is 1 or 2 and most preferably, y is 1. Preferably, z is 1, 2, 3, 4, 5 or 6, more preferably z is 1, 2, 3 or 4, even more preferably z is 1, 2 or 3, yet even more preferably z is 1 or 2 and most preferably z is 1. More preferably, y is 1 or 2, preferably 1, and z is 1, 2, 3 or 4, yet even more preferably y is 1 or 2, preferably 1, and z is 1, 2 or 3, yet even more preferably y is 1 or 2, preferably 1, and z is 1 or 2, and most preferably y is 1 and z is 1. In a preferred embodiment, the bioconjugate is according to the formula B-Sp-$(D)_4$, B-Sp-$(D)_3$, B-Sp-$(D)_2$ or B-Sp-D.

In a preferred embodiment, the bioconjugate according to the invention is represented by formula (5):

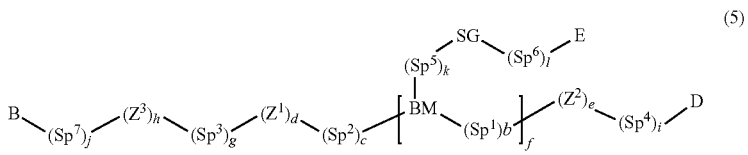

(5)

Herein, b, c, d, e, f, g, i, D, BM, SG, E, $Sp^1$, $Sp^2$, $Sp^3$, $Sp^4$, $Sp^5$, $Sp^6$, $Z^1$ and $Z^2$, and preferred embodiments thereof, are as defined above for the linker according to the invention or the linker-conjugate of the invention, and
h is 0 or 1;
j is 0 or 1;
$Z^3$ is a connecting group that connects B or $Sp^7$ to $Sp^3$, $Z^1$, $Sp^2$ or BM;
$Sp^7$ is a spacer moiety; and
B is a biomolecule as defined herein.

Preferably, h is 1. Preferably, j is 0. Preferred embodiments of biomolecule B are as defined above. Preferred embodiment for $Sp^7$ are according to the preferred embodiments of any one $Sp^1$-$Sp^6$ as defined above. $Z^3$ is a connecting group. As described above, the term "connecting group" herein refers to the structural element connecting one part of a compound and another part of the same compound. Typically, a bioconjugate is prepared via reaction of a reactive group $Q^1$ present in a linker-conjugate with a functional group $F^1$ present in a biomolecule. As will be understood by the person skilled in the art, the nature of connecting group $Z^3$ depends on the type of organic reaction that was used to establish the connection between a biomolecule and a linker-conjugate. In other words, the nature of $Z^3$ depends on the nature of reactive group $Q^1$ of the linker-conjugate and the nature of functional group $F^1$ in the biomolecule. Since there is a large number of different chemical reactions available for establishing the connection between a biomolecule and a linker-conjugate, consequently there is a large number of possibilities for $Z^3$.

Several examples of suitable combinations of $F^1$ and $Q^1$, and of connecting group $Z^3$ that will be present in a bioconjugate when a linker-conjugate comprising $Q^1$ is conjugated to a biomolecule comprising a complementary functional group $F^1$, are shown in FIG. 6.

When $F^1$ is for example a thiol group, complementary groups $Q^1$ include N-maleimidyl groups and alkenyl groups, and the corresponding connecting groups $Z^3$ are as shown in FIG. 6. When $F^1$ is a thiol group, complementary groups $Q^1$ also include allenamide groups.

When $F^1$ is for example an amino group, complementary groups $Q^1$ include ketone groups and activated ester groups, and the corresponding connecting groups $Z^3$ are as shown in FIG. 6.

When $F^1$ is for example a ketone group, complementary groups $Q^1$ include (O-alkyl)hydroxylamino groups and hydrazine groups, and the corresponding connecting groups $Z^3$ are as shown in FIG. 6.

When $F^1$ is for example an alkynyl group, complementary groups $Q^1$ include azido groups, and the corresponding connecting group $Z^3$ is as shown in FIG. 6.

When $F^1$ is for example an azido group, complementary groups $Q^1$ include alkynyl groups, and the corresponding connecting group $Z^3$ is as shown in FIG. 6.

When $F^1$ is for example a cyclopropenyl group, a transcyclooctene group or a cyclooctyne group, complementary groups $Q^1$ include tetrazinyl groups, and the corresponding connecting group $Z^3$ is as shown in FIG. 6. In these particular cases, $Z^3$ is only an intermediate structure and will expel $N_2$, thereby generating a dihydropyridazine (from the reaction with alkene) or pyridazine (from the reaction with alkyne).

Additional suitable combinations of $F^1$ and $Q^1$, and the nature of resulting connecting group $Z^3$ are known to a person skilled in the art, and are e.g. described in G. T. Hermanson, "*Bioconjugate Techniques*", Elsevier, 3$^{rd}$ Ed. 2013 (ISBN:978-0-12-382239-0), in particular in Chapter 3, pages 229-258, incorporated by reference. A list of complementary reactive groups suitable for bioconjugation processes is disclosed in Table 3.1, pages 230-232 of Chapter 3 of G. T. Hermanson, "*Bioconjugate Techniques*", Elsevier, 3$^{rd}$ Ed. 2013 (ISBN:978-0-12-382239-0), and the content of this Table is expressly incorporated by reference herein.

In the bioconjugate according to (5), it is preferred that at least one of $Z^3$, $Sp^3$, $Z^1$ and $Sp^2$ is present, i.e. at least one of h, g, d and c is not 0. It is also preferred that at least one of $Sp^1$, $Z^2$ and $Sp^4$ is present, i.e. that at least one of b, e and i is not 0. More preferably, at least one of $Z^3$, $Sp^3$, $Z^1$ and $Sp^2$ is present and at least one of $Sp^1$, $Z^2$ and $Sp^4$ is present, i.e. it is preferred that at least one of b, e and i is not 0 and at least one of h, g, d and c is not 0.

Process for the Preparation of a Bioconjugate

In a fourth aspect, the present invention also relates to a process for the preparation of a bioconjugate, the process comprising the step of reacting a reactive group $Q^1$ of a linker-conjugate according to the invention with a functional group $F^1$ of a biomolecule. The linker-conjugate according to the invention, and preferred embodiments thereof, are described in more detail above. FIG. 1 shows the general concept of conjugation of biomolecules: a biomolecule of interest (BOI) comprising one or more functional groups $F^1$ is incubated with (excess of) a target molecule D (also referred to as molecule of interest or MOI) covalently attached to a reactive group $Q^1$ via a specific linker. In the process of bioconjugation, a chemical reaction between $F^1$ and $Q^1$ takes place, thereby forming a bioconjugate comprising a covalent bond between the BOI and the MOI. The BOI may e.g. be a peptide/protein, a glycan or a nucleic acid. In the process according to the invention, the linker is a sulfamide linker.

The present invention thus relates to a process for the preparation of a bioconjugate, the process comprising the step of reacting a reactive group $Q^1$ of a linker-conjugate with a functional group $F^1$ of a biomolecule, wherein the linker-conjugate is the linker-conjugate according to the invention as defined above and comprises the linker according to the invention as defined above. The present process occurs under condition such that reactive group $Q^1$ of the linker-conjugate is reacted with the functional group $F^1$ of the biomolecule to covalently link the biomolecule to the linker-conjugate. In the process according to the invention, $Q^1$ reacts with $F^1$, forming a covalent connection between the biomolecule and the linker-moiety. Complementary reactive groups $Q^1$ and functional groups $F^1$ are described in more detail above and below.

In a preferred embodiment, the process according to this aspect of the invention concerns a process for the preparation of a bioconjugate via a cycloaddition or a Michael reaction. A preferred Michael reaction is the thiol-maleimide addition, most preferably wherein $Q^1$ is maleimide and $F^1$ is a thiol group. Preferred cycloadditions are a (4+2)-cycloaddition (e.g. a Diels-Alder reaction) or a (3+2)-cycloaddition (e.g. a 1,3-dipolar cycloaddition). Preferably, the conjugation is the Diels-Alder reaction or the 1,3-dipolar cycloaddition. The preferred Diels-Alder reaction is the inverse-electron demand Diels-Alder cycloaddition. In another preferred embodiment, the 1,3-dipolar cycloaddition is used, more preferably the alkyne-azide cycloaddition, and most preferably wherein $Q^1$ is or comprises an alkyne group and $F^1$ is an azido group. Cycloadditions, such as Diels-Alder reactions and 1,3-dipolar cycloadditions are known in the art, and the skilled person knowns how to perform them. In a further preferred embodiment, the invention concerns a process for the preparation of a bioconjugate, wherein the target molecule is hydrophobic (i.e. poorly soluble in water), most preferably wherein the target molecule has a water solubility of at most 0.1% (w/w) in water (20° C. and 100 kPa). In an especially preferred embodiment, the invention concerns a process for the preparation of a bioconjugate via cycloaddition, preferably a 1,3-dipolar cycloaddition, more preferably the alkyne-azide cycloaddition, and most preferably wherein $Q^1$ is or comprises an alkyne group and $F^1$ is an azido group, and wherein the target molecule is hydrophobic, most preferably wherein the target molecule has a water solubility of at most 0.1% (w/w) in water (20° C. and 100 kPa).

Biomolecules are described in more detail above. Preferably, in the process according to the invention the biomolecule is selected from the group consisting of proteins (including glycoproteins and antibodies), polypeptides, peptides, glycans, lipids, nucleic acids, oligonucleotides, polysaccharides, oligosaccharides, enzymes, hormones, amino acids and monosaccharides. More preferably, biomolecule B is selected from the group consisting of proteins (including glycoproteins and antibodies), polypeptides, peptides, glycans, nucleic acids, oligonucleotides, polysaccharides, oligosaccharides and enzymes. Most preferably, biomolecule B is selected from the group consisting of proteins, including glycoproteins and antibodies, polypeptides, peptides and glycans.

Target molecules are described in more detail above. In a preferred embodiment of the process according to the invention, the target molecule is selected from the group consisting of an active substance, a reporter molecule, a polymer, a solid surface, a hydrogel, a nanoparticle, a microparticle and a biomolecule. Active substances, reporter molecules, polymers, solid surfaces, hydrogels, nanoparticles and microparticles are described in detail above, as are their preferred embodiments. In view of the significantly improved water solubility of the linker-conjugate when the sulfamide linker according to the invention is employed, a preferred embodiment of the process for the preparation of a bioconjugate employs a hydrophobic target molecule. The hydrophobic target molecule in its unconjugated form typically has a water solubility of at most 1% (w/w), preferably at most 0.5% (w/w), most preferably at most 0.1% (w/w), determined at 20° C. and 100 kPa.

Reactive group $Q^1$ are described in more detail above. In the process according to the invention, it is preferred that reactive group $Q^1$ is selected from the group consisting of, optionally substituted, N-maleimidyl groups, halogenated N-alkylamido groups, sulfonyloxy N-alkylamido groups, ester groups, carbonate groups, sulfonyl halide groups, thiol groups or derivatives thereof, alkenyl groups, alkynyl groups, (hetero)cycloalkynyl groups, bicyclo[6.1.0]non-4-yn-9-yl] groups, cycloalkenyl groups, tetrazinyl groups, azido groups, phosphine groups, nitrile oxide groups, nitrone groups, nitrile imine groups, diazo groups, ketone groups, (O-alkyl)hydroxylamino groups, hydrazine groups, halogenated N-maleimidyl groups, 1,1-bis(sulfonylmethyl) methylcarbonyl groups or elimination derivatives thereof, carbonyl halide groups and allenamide groups.

In a further preferred embodiment, $Q^1$ is according to formula (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zl), (9zm) or (9zn), wherein (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zl), (9zm), (9zn) and preferred embodiments thereof, are as defined above for the linker-conjugate according to the invention. More preferably, $Q^1$ is according to formula (9a), (9b), (9c), (9f), (9j), (9n), (9o), (9p), (9q), (9s), (9t), (9zh), (9r), (9zl), (9zm) or (9zn). Even more preferably, $Q^1$ is according to formula (9a), (9n), (9o), (9p), (9q), (9t), (9zh) or (9s), and most preferably, $Q^1$ is according to formula (9a), (9p), (9q), (9n), (9t), (9zh) or (9o), and preferred embodiments thereof, as defined above.

In an especially preferred embodiment, $Q^1$ comprises an alkyne group, preferably selected from the alkynyl group as described above, the cycloalkenyl group as described above, the (hetero)cycloalkynyl group as described above and a bicyclo[6.1.0]non-4-yn-9-yl] group, more preferably $Q^1$ is selected from the formulae (9j), (9n), (9o), (9p), (9q) and (9zk), as defined above. Most preferably, $Q^1$ is a bicyclo [6.1.0]non-4-yn-9-yl] group, preferably of formula (9q).

In a further preferred embodiment of the process according to the invention, the linker-conjugate is according to formula (4), as defined above. Definitions and preferred embodiments for each of $Q^1$, BM, E, SG, D b, c, d, e, f, g, i, k, l, $Sp^1$, $Sp^2$, $Sp^3$, $Sp^4$, $Sp^5$, $Sp^6$, $Z^1$ and $Z^2$ are given above for the linker and the linker-conjugate, and also apply to the linker-conjugate used in the process according to the present aspect.

$Sp^1$, $Sp^2$, $Sp^3$, $Sp^4$, $Sp^5$ and $Sp^6$ are, independently, spacer moieties, in other words, $Sp^1$, $Sp^2$, $Sp^3$, $Sp^4$, $Sp^5$ and $Sp^6$ may differ from each other. $Sp^1$, $Sp^2$, $Sp^3$, $Sp^4$, $Sp^5$ and $Sp^6$ may be present or absent (b, c, g, i, k and l are, independently, 0 or 1). However, it is preferred that at least one of $Sp^1$, $Sp^2$, $Sp^3$, $Sp^4$, $Sp^5$ and $Sp^6$ is present, i.e. it is preferred that at least one of b, c, g, i, k and l is not 0. Preferred embodiment for each of the spacers $Sp^1$, $Sp^2$, $Sp^3$, $Sp^4$, $Sp^5$ and $Sp^6$ are described above for the linker according to the invention.

In a partially preferred process according to the invention, $Sp^1$, $Sp^2$, $Sp^4$, $Sp^5$ and $Sp^6$, if present, are independently selected from the group consisting of linear or branched $C_1$-$C_{20}$ alkylene groups, the alkylene groups being optionally substituted and optionally interrupted by one or more heteroatoms selected from the group consisting of O, S and $NR^3$, wherein $R^3$ is independently selected from the group consisting of hydrogen and $C_1$-$C_4$ alkyl groups, and wherein $Q^1$ is according to formula (9a), (9p), (9q), (9n), (9t), (9zh) or (9o):

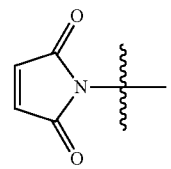

9a

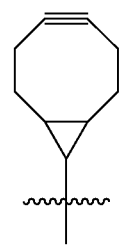

9q

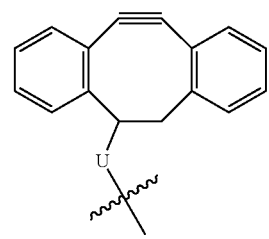

9n

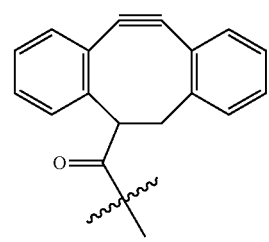

9o

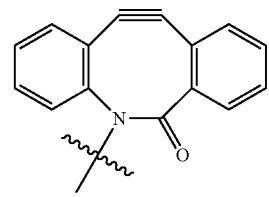

9p

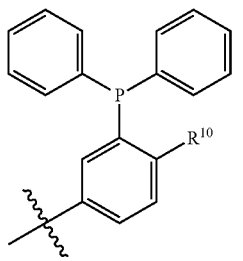
9t

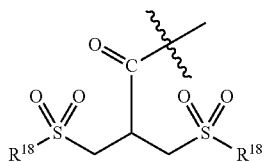
9zh wherein:
R[10] is a (thio)ester group; and
R[18] is selected from the group consisting of, optionally substituted, $C_1$-$C_{12}$ alkyl groups and $C_4$-$C_{12}$ (hetero) aryl groups.

As described above, in the process for the preparation of a bioconjugate, a reactive group $Q^1$ that is present in a linker-conjugate is reacted with a functional group $F^1$ that is present in a biomolecule.

In the process according to the invention, more than one functional group may be present in the biomolecule. When two or more functional groups are present, said groups may be the same or different. Similarly, more than one reactive group may be present in the linker-conjugate. When two or more reactive groups are present, said groups may be the same or different. In a preferred embodiment of the process according to the invention, the linker-conjugate comprises one reactive group $Q^1$, and one or more target molecules D which may be the same or different. The linker-conjugate comprises for example 1, 2, 3, 4, 5 or 6, preferably 1, 2, 3 or 4, more preferably 1, 2 or 3, even more preferably 1 or 2 target molecule D. In a particularly preferred embodiment the linker-conjugate comprises 1 target molecule D. In another particularly preferred embodiment, the linker-conjugate comprises 2 target molecules D, which may be the same or different. In another preferred embodiment, the biomolecule comprises two or more functional groups F, which may be the same or different, and two or more functional groups react with a complementary reactive group Q of a linker-conjugate. For example a biomolecule comprising two functional groups F, i.e. $F^1$ and $F^2$, may react with two linker-conjugates comprising a functional group $Q^1$, which may be the same or different, to form a bioconjugate.

Examples of a functional group $F^1$ in a biomolecule comprise an amino group, a thiol group, a carboxylic acid, an alcohol group, a carbonyl group, a phosphate group, or an aromatic group. The functional group in the biomolecule may be naturally present or may be placed in the biomolecule by a specific technique, for example a (bio)chemical or a genetic technique. The functional group that is placed in the biomolecule may be a functional group that is naturally present in nature, or may be a functional group that is prepared by chemical synthesis, for example an azide, a terminal alkyne, a cyclopropene moiety or a phosphine moiety. In view of the preferred mode of conjugation by cycloaddition, it is preferred that $F^1$ is group capable of reacting in a cycloaddition, such as a diene, a dienophile, a 1,3-dipole or a dipolarophile, preferably $F^1$ is selected from a 1,3-dipole (typically an azido group, nitrone group, nitrile oxide group, nitrile imine group or diazo group) or a dipolarophile (typically an alkenyl or alkynyl group). Herein, $F^1$ is a 1,3-dipole when $Q^1$ is a dipolarophile and $F^1$ is a dipolarophile when $Q^1$ is a 1,3-dipole, or $F^1$ is a diene when $Q^1$ is a dienophile and $F^1$ is a dienophile when $Q^1$ is a diene. Most preferably, $F^1$ is a 1,3-dipole, preferably $F^1$ is or comprises an azido group.

Figure 2:
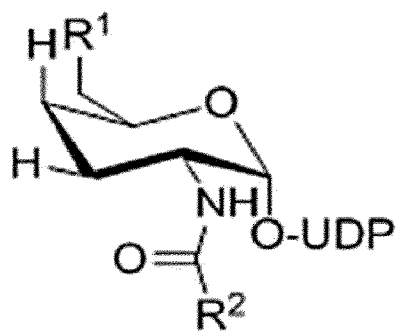
FIG. 2 shows several structures of derivatives of UDP sugars of galactosamine, which may be modified with e.g. a 3-mercaptopropionyl group (11a), an azidoacetyl group (11b), or an azidodifluoroacetyl group (11c) at the 2-position, or with an azido group at the 6-position of N-acetyl galactosamine (11 d).

Several examples of a functional group that is placed into a biomolecule are shown in FIG. 2. FIG. 2 shows several structures of derivatives of UDP sugars of galactosamine, which may be modified with e.g. a thiopropionyl group (11a), an azidoacetyl group (11b), or an azidodifluoroacetyl group (11c) at the 2-position, or with an azido group at the 6-position of N-acetyl galactosamine (11 d).

Figure 3:
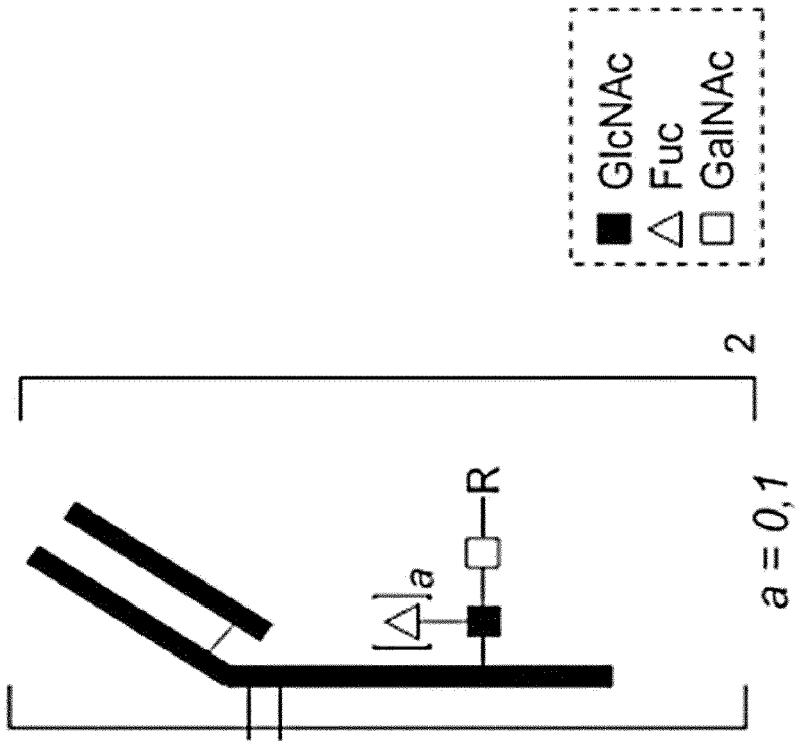
FIG. 3 schematically displays how any of the UDP-sugars 11a-d may be attached to a glycoprotein comprising a GlcNAc moiety 12 (e.g. a monoclonal antibody the glycan of which is trimmed by an endoglycosidase) under the action of a galactosyltransferase mutant or a GalNAc-transferase, thereby generating a β-glycosidic 1-4 linkage between a GalNAc derivative and GlcNAc (compounds 13a-d, respectively).
Figure 3:
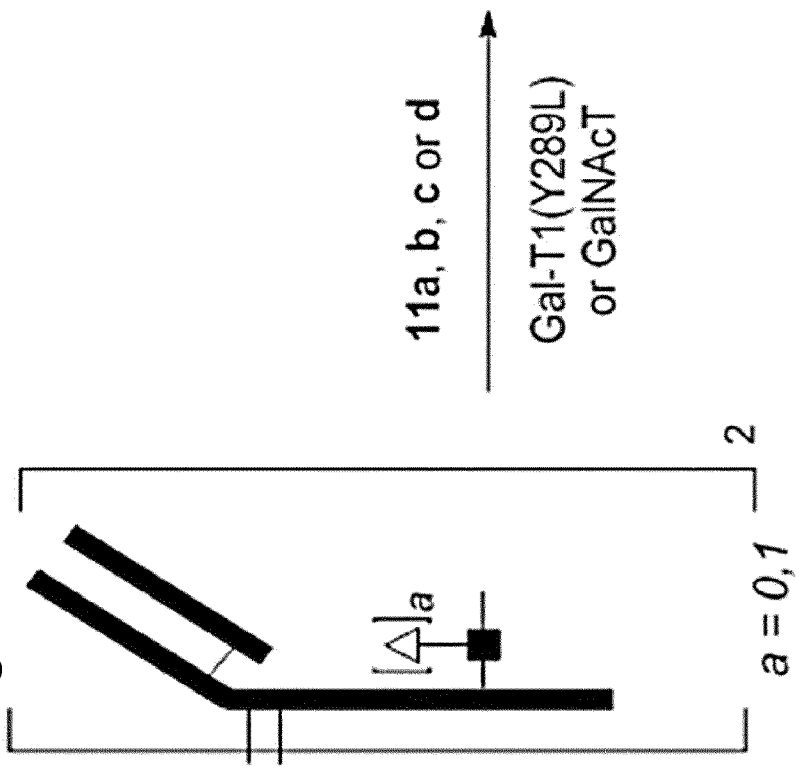

FIG. 3 schematically displays how any of the UDP-sugars 11a-d may be attached to a glycoprotein comprising a GlcNAc moiety 12 (e.g. a monoclonal antibody the glycan of which is trimmed by an endoglycosidase) under the action of a galactosyltransferase mutant or a GalNAc-transferase, thereby generating a β-glycosidic 1-4 linkage between a GalNAc derivative and GlcNAc (compounds 13a-d, respectively).

Preferred examples of naturally present functional groups $F^1$ include a thiol group and an amino group. Preferred examples of a functional group that is prepared by chemical synthesis for incorporation into the biomolecule include a ketone group, a terminal alkyne group, an azide group, a cyclo(hetero)alkyne group, a cyclopropene group, or a tetrazine group.

As was described above, complementary reactive groups $Q^1$ and functional groups $F^1$ are known to a person skilled in the art, and several suitable combinations of $Q^1$ and $F^1$ are described above, and shown in FIG. 6. A list of complementary groups $Q^1$ and $F^1$ is disclosed in in Table 3.1, pages 230-232 of Chapter 3 of G. T. Hermanson, "Bioconjugate Techniques", Elsevier, 3rd Ed. 2013 (ISBN:978-0-12-382239-0), and the content of this Table is expressly incorporated by reference herein.

Figure 4:
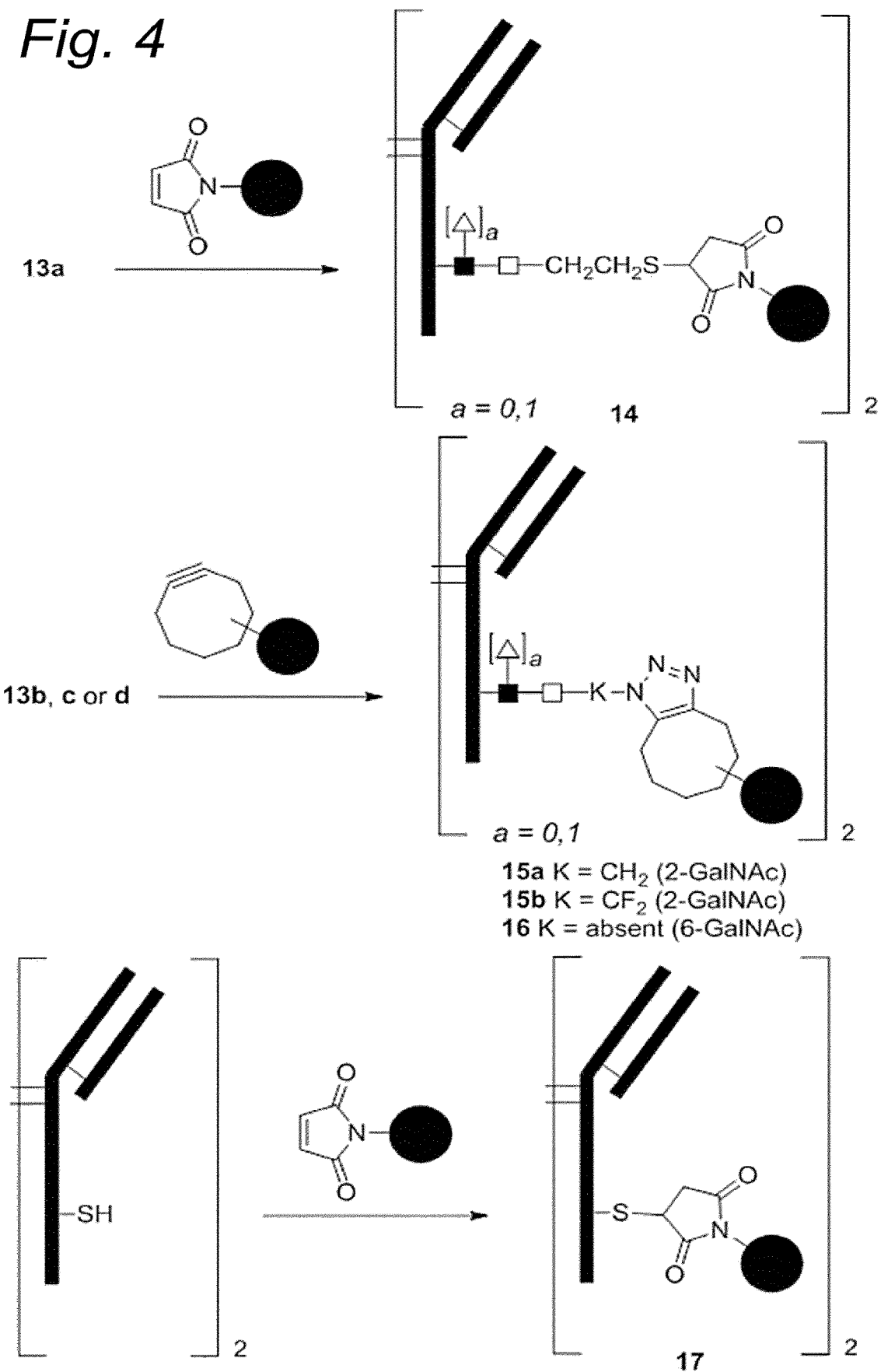
FIG. 4 shows how a modified antibody 13a-d may undergo a bioconjugation process by means of nucleophilic addition to maleimide (as for 3-mercaptopropionyl-galactosamine-modified 13a leading to thioether conjugate 14, or for conjugation to a engineered cysteine residue leading to thioether conjugate 17) or upon strain-promoted cycloaddition with a cyclooctyne reagent (as for 13b, 13c or 13d leading to triazoles 15a, 15b or 16, respectively).
Figure 5A:
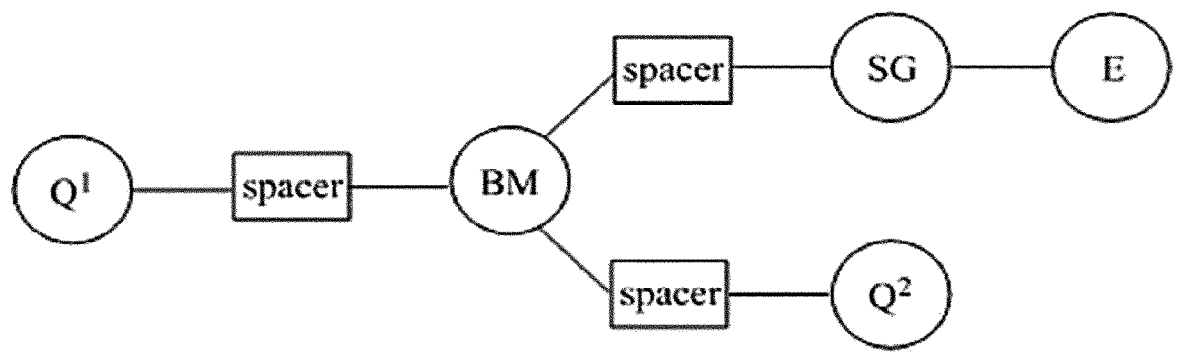
FIG. 5 depicts the general structure of the linker-construct (FIG. 5A), the linker-conjugate (FIG. 5B) and the bioconjugate (FIG. 5C) according to the invention. Herein, B refers to biomolecule, D refers to target molecule, SG refers to sulfamide group, E refers to capping moiety, BM refers to branching moiety and $Q^1$ and $Q^2$ are reactive groups.
Figure 5B:
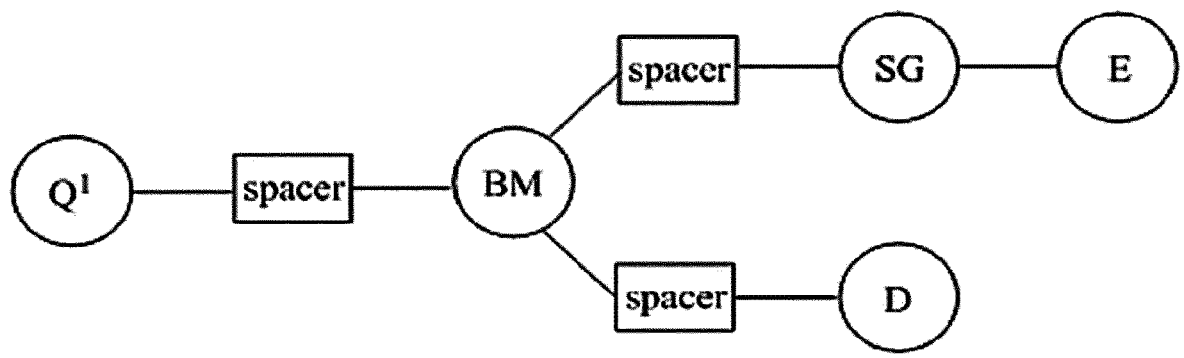
Figure 5C:
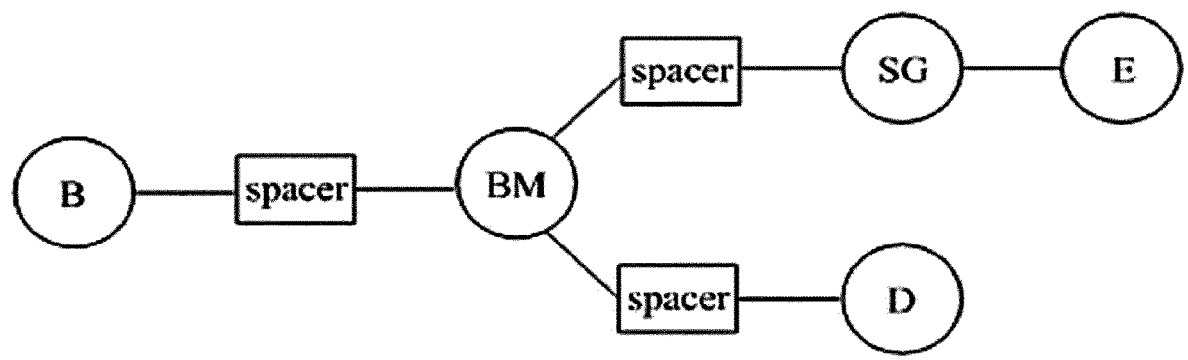

An embodiment of the process according to the invention is depicted in FIG. 4. FIG. 4 shows how a modified antibody 13a-d may undergo a bioconjugation process by means of nucleophilic addition with maleimide (as for 3-mercaptopropionyl-galactosamine-modified 13a leading to thioether conjugate 14, or for conjugation to an engineered cysteine residue leading to thioether conjugate 17) or upon strain-promoted cycloaddition with a cyclooctyne reagent (as for 13b, 13c or 13d, leading to triazoles 15a, 15b or 16, respectively).

The invention further relates to a bioconjugate obtainable by the process according to the invention for the preparation of a bioconjugate.

Use

In a fifth aspect, the invention concerns the use of the linker according to the invention in bioconjugation for (a) improving conjugation efficiency, (b) reducing aggregation, (c) increasing stability of a bioconjugate as defined herein and/or (d) increasing therapeutic index of the bioconjugate. In one embodiment, the use according to the present aspect is for (a) improving conjugation efficiency in a bioconjugation reaction wherein the linker-conjugate according to the present invention reacts with a biomolecule, as described herein. In one embodiment, the use according to the present aspect is for (b) reducing aggregation during the bioconjugation reaction, e.g. the bioconjugation reaction according to the invention (in-process aggregation) and/or for reducing aggregation of the bioconjugate according to the invention (product aggregation). In one embodiment, the use according to the present aspect is for (c) increasing stability of the bioconjugate according to the present invention, in particular for increasing stability towards hydrolysis. In one embodiment, the use according to the present aspect is for (d) increasing therapeutic index of the bioconjugate.

A first advantages of the process for the preparation of a bioconjugate as described herein, and of the linker-conjugates and sulfamide linker according to the invention is that conjugation efficiency increases in case a sulfamide linker is used instead of a typical polyethylene glycol (PEG) spacer. An additional advantage of a sulfamide group, in particular of an acylsulfamide or a carbamoylsulfamide group, is its high polarity, which imparts a positive effect on the solubility of a linker comprising such group, and on the construct as a whole, before, during and after conjugation. In view of this increased polarity, conjugation with first precursor containing the sulfamide linker according to the invention are particularly suited to conjugate hydrophobic target compounds to a biomolecule. The high polarity of the sulfamides also has a positive impact in case hydrophobic moieties are conjugated to a biomolecule of interest, which is known to require large amounts of organic co-solvent during conjugation and/or induce aggregation of the bioconjugate. High levels of co-solvent (up to 50% of DMA, DMF, or DMSO) may induce protein denaturation during the conjugation process and/or may require special equipment in the manufacturing process. Thus, the problem of aggregation associated with the hydrophobic linking moieties in bioconjugates is efficiently solved by using the sulfamide linker according to the invention in the spacer between the target molecule and the reactive group $Q^1$ in the linker-conjugate in the formation of the bioconjugate. An additional advantage of a sulfamide linker according the invention, and its use in bioconjugation processes, is its ease of synthesis and high yields. Furthermore, the inventors have found that the bioconjugates according to the invention are more stable than bioconjugates not according to the present invention, i.e. not comprising the linker according to the invention.

Lastly, the inventors surprisingly found that a bioconjugate according to the invention exhibits a greater therapeutic index compared to the same bioconjugate, i.e. the same biomolecule, the same active substance (drug) and the same biomolecule drug ratio, but not containing a linker according to the invention, i.e. wherein no sulfamide group (SG) is present. That the linker could have an effect on the therapeutic efficacy of a bioconjugate, such as an antibody-drug-conjugate, could not be envisioned based on the current knowledge. In the field, linkers are considered inert when it comes to treatment and are solely present as a consequence of the preparation of the bioconjugate. That the selection of a specific linker has an effect on the therapeutic efficacy is unprecedented and a breakthrough discovery in the field of bioconjugates, in particular antibody-drug-conjugates. The bioconjugates according to the invention are thus more therapeutically effective as the same bioconjugates, i.e. the same biomolecule, the same active substance (drug) and the same biomolecule-active substance ratio, containing a different linker. This finding has dramatic implications on the treatment of subjects with the bioconjugate according to the invention, as treatment doses may be lowered and as a consequence potential, unwanted, side-effects are reduced. Alternatively, as a result of the increased tolerability of the bioconjugate (i.e. increased stability and low aggregation potential) according to the invention, treatment doses might be increased without the potential increase in unwanted side-effects.

The use according to the present aspect is largely non-medical. In one embodiment, the use is a non-medical use for (a) improving conjugation efficiency, (b) reducing aggregation, (c) increasing stability of a bioconjugate as defined herein and/or (d) increasing therapeutic index of the bioconjugate.

The first aspect of the invention can also be worded as the linker according to the invention for use in for (a) improving conjugation efficiency, (b) reducing aggregation, (c) increasing stability of a bioconjugate as defined herein and/or (d) increasing therapeutic index of the bioconjugate. In other words, the present aspect concerns the use of a linker according to the invention for (a) improving conjugation efficiency, (b) reducing aggregation, (c) increasing stability of a bioconjugate as defined herein and/or (d) increasing therapeutic index of the bioconjugate. The invention according to the present aspect can also be worded as the use of a linker according to the invention in a bioconjugate according to the invention, or in the preparation of a bioconjugate according to the invention, for (a) improving conjugation efficiency, (b) reducing aggregation, (c) increasing stability of a bioconjugate as defined herein and/or (d) increasing therapeutic index of the bioconjugate. The use as defined herein may be referred to as a non-medical or non-therapeutic use.

The bioconjugate subject of the use according to the present aspect is preferably obtainable by the process for the preparation of a bioconjugate as defined above, more preferably the bioconjugate is obtained by the process for the preparation of a bioconjugate as defined above. It was found that bioconjugates thus obtained had an even further improved therapeutic index.

The inventors found that the linker according to the invention, as comprised in the bioconjugates according to the invention, has an effect on both aspects of the therapeutic index: (a) on the therapeutic efficacy and (b) on the tolerability. Thus, the method for increasing the therapeutic index is preferably for (a) increasing the therapeutic efficacy, and/or (b) increasing the tolerability of a bioconjugate according to the invention.

Thus, in one embodiment, the method according to the first aspect is for increasing the therapeutic efficacy of a bioconjugate according to the invention. Herein, "increasing the therapeutic efficacy" can also be worded as "lowering the effective dose" or "lowering the $ED_{50}$ value" or "increasing the protective index". Likewise, in one embodiment, the method according to the first aspect is for increasing the tolerability of a bioconjugate according to the invention. Herein, "increasing the tolerability" can also be worded as "increasing the maximum tolerated dose (MTD)", "increasing the $TD_{50}$ value" or "reducing the toxicity". In one especially preferred embodiment, the method according to the first aspect is for (a) increasing the therapeutic efficacy and (b) increasing the tolerability of a bioconjugate according to the invention.

Medical Use

The invention thus concerns in a sixth aspect a method for the treatment of a subject in need thereof, comprising the administration of the bioconjugate according to the invention as defined above. The subject in need thereof is most preferably a cancer patient. The use of bioconjugates, such as antibody-drug conjugates, is well-known in the field of cancer treatment, and the bioconjugates according to the invention are especially suited in this respect. The method as described is typically suited for the treatment of cancer. In the method according to the sixth aspect, the bioconjugate is typically administered in a therapeutically effective dose. The bioconjugate according to the invention is described a great detail above.

The sixth aspect of the invention can also be worded as a bioconjugate according to the invention for use in the treatment of a subject in need thereof, preferably for the treatment of cancer. In other words, the second aspect concerns the use of a bioconjugate according to the invention for the preparation of a medicament pharmaceutical for use in the treatment of a subject in need thereof, preferably for use in the treatment of cancer.

EXAMPLES

Examples 1-3: Preparation of Compound 25

The synthetic approach towards compound 25 is depicted here below.

sulfonyl isocyanate (14.3 μL, 0.164 mmol) and the resulting mixture was stirred for 15 min. Then, Et₃N (68 μL, 0.491 mmol) was added, followed by benzylamine (18 μL, 0.164 mmol). After 1 h, DCM (10 mL) and sat. NH₄Cl solution (10 mL) were added. The layers were separated and the water phase was extracted with DCM (2×10 mL) and EtOAc (3×10 mL). The combined organic layers were dried over sodium sulfate, filtered and concentrated in vacuo. Flash chromatography (10-50% EtOAc in pentane) afforded the product (72 mg, 0.14 mmol, 85%). LRMS (ESI+) calcd for $C_{22}H_{39}N_3O_7SSi$ (M+H⁺) 518.24, found 518.28.

Example 2: Preparation of Compound 22

To a solution of compound 21 (72 mg, 0.14 mmol) in DCM (1 mL) was added TFA (1 mL) and the reaction mixture was stirred at rt overnight. The reaction was concentrated and co-evaporated with toluene (2×15 mL) to

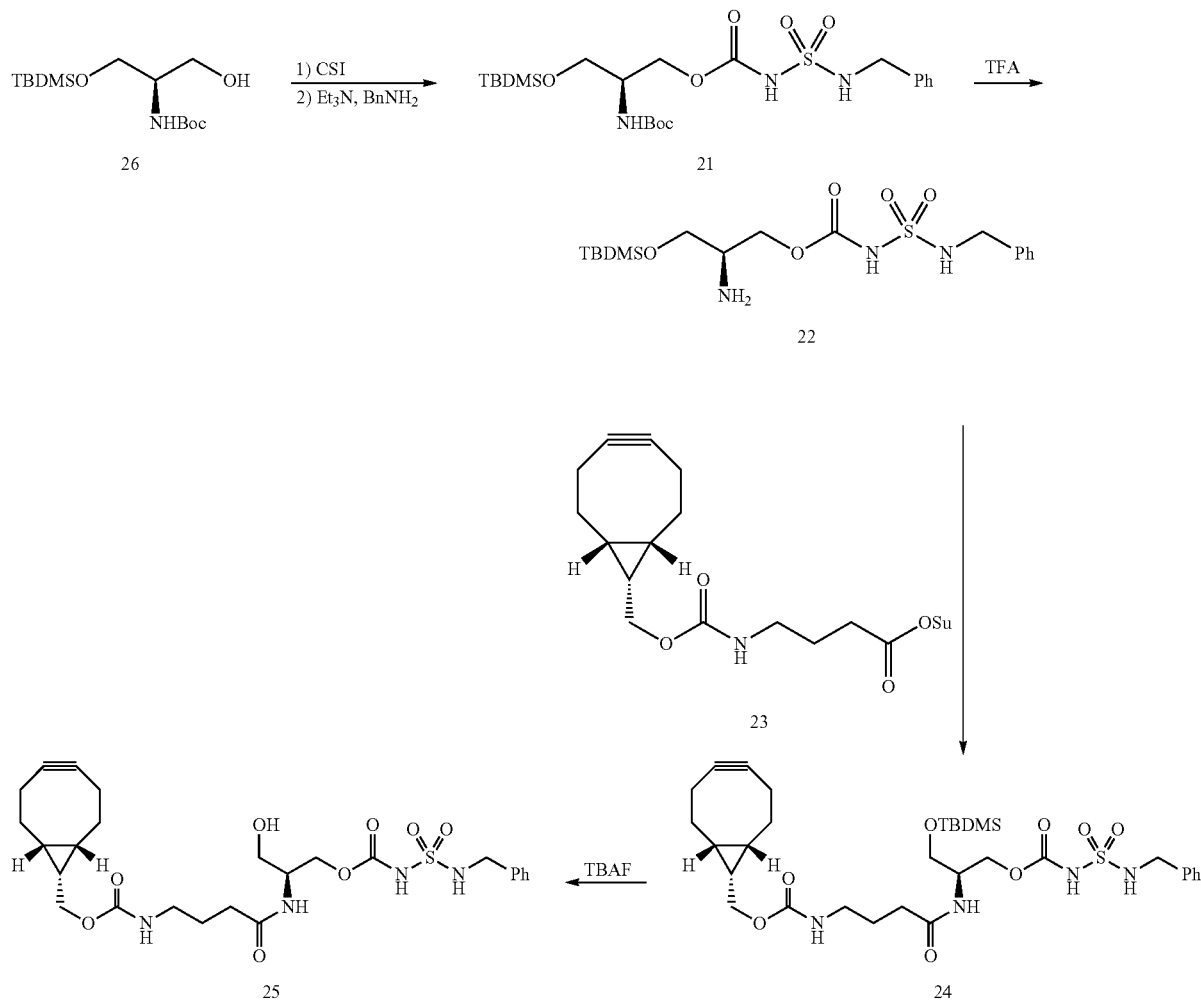

Example 1: Preparation of Compound 21

To a solution of (R)-(+)-N-(tert-butoxycarbonyl)-O-(tert-butyldimethylsilyl)serinol (26; 50 mg, 0.164 mmol) in DCM (1.6 mL) under a nitrogen atmosphere was added chloroafford the crude product. 1H-NMR (400 MHz, CD3OD): δ 7.38-7.24 (m, 5H), 4.29-4.18 (m, 4H), 3.91-3.64 (m, 3H), 3.54-3.43 (m, 1H), 0.98-0.86 (m, 5H), 0.15-0.04 (m, 5H). LRMS (ESI+) calcd for $C_{17}H_{31}N_3O_5SSi$ (M+H+) 418.18, found 418.20.

Example 3: Preparation of Compound 25

To a solution of the crude compound 22 (0.14 mmol) in MeCN (2 mL) under a nitrogen atmosphere, was added Et$_3$N (59 µL, 0.42 mmol), followed by addition of compound 23 (79 mg, 0.21 mmol) in dry DMF (0.5 mL). The resulting solution was stirred at rt overnight and concentrated to afford the crude product. LRMS (ESI+) calcd for C$_{32}$H$_{50}$N$_4$O$_8$SSi (M+H$^+$) 679.32, found 679.27.

The resulting compound 24 was dissolved in THF (1.5 mL) and TBAF (100 mg) was added. The reaction was allowed to stir at rt for 24 h with an extra addition of TBAF (200 mg) after 18 h. After 24 h, the reaction was concentrated, taken up in EtOAc (15 mL) and washed with H$_2$O (2×10 mL). The water phase was extracted with DCM (20 mL), the combined organic layers were dried over sodium sulfate, filtered and the solvent removed under reduced pressure. Flash chromatography (80-100% EtOAc in pentane) afforded the product. $^1$H-NMR (400 MHz, CDCl$_3$): δ 7.38-7.28 (m, 5H), 4.95 (t, J=6 Hz, 1H), 4.28-4.20 (m, 4H), 4.17-4.08 (m, 3H), 3.82-3.65 (m, 2H), 2.35-2.15 (m, 10H), 1.93-1.49 (m, 9H), 1.01-0.82 (m, 6H). LRMS (ESI+) calcd for C$_{26}$H$_{36}$N$_4$O$_8$S (M+H$^+$) 565.23, found 565.25.

Examples 4-9: Preparation of Compound 32

The synthetic approach towards compound 32 is depicted here below.

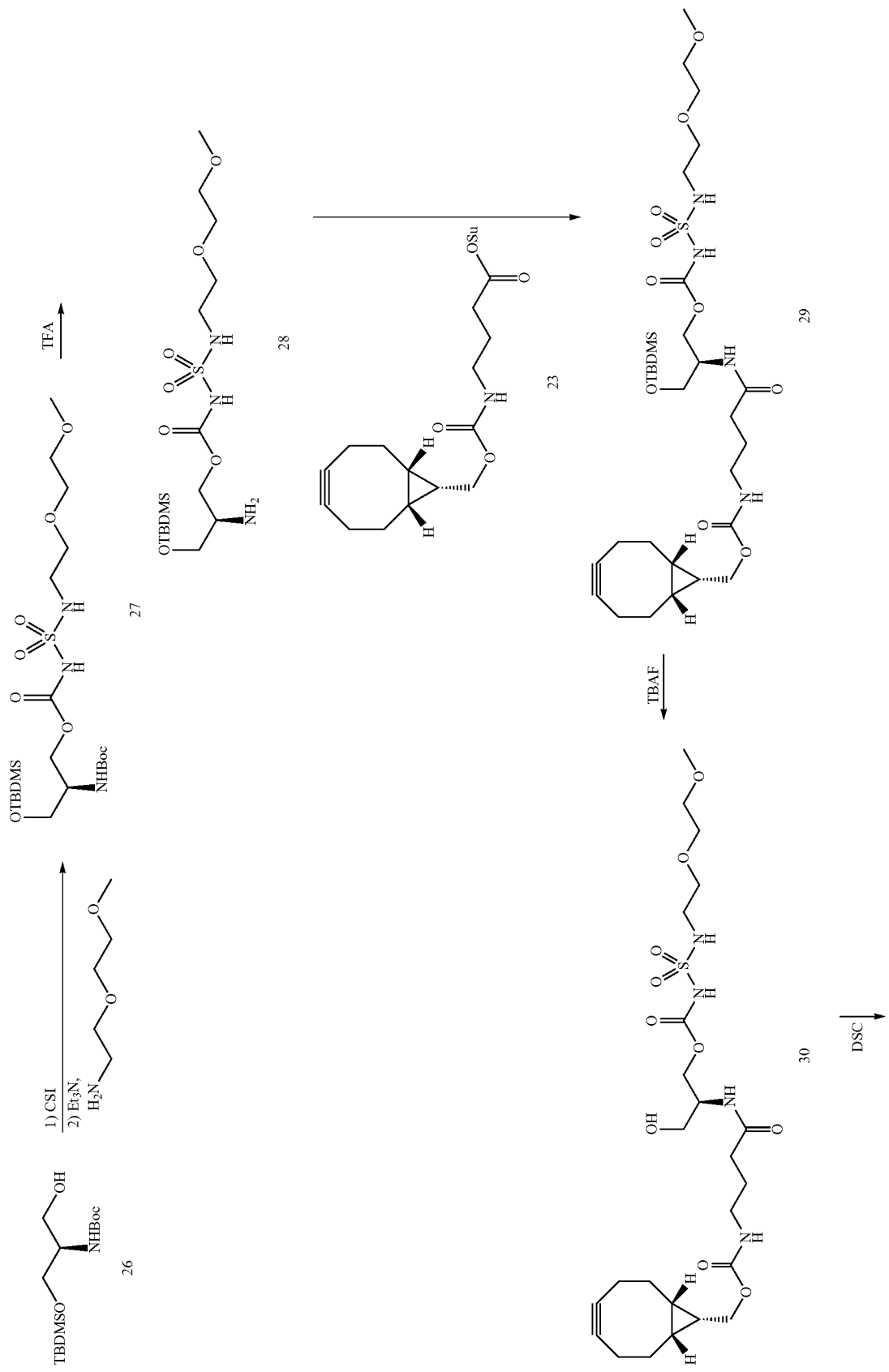

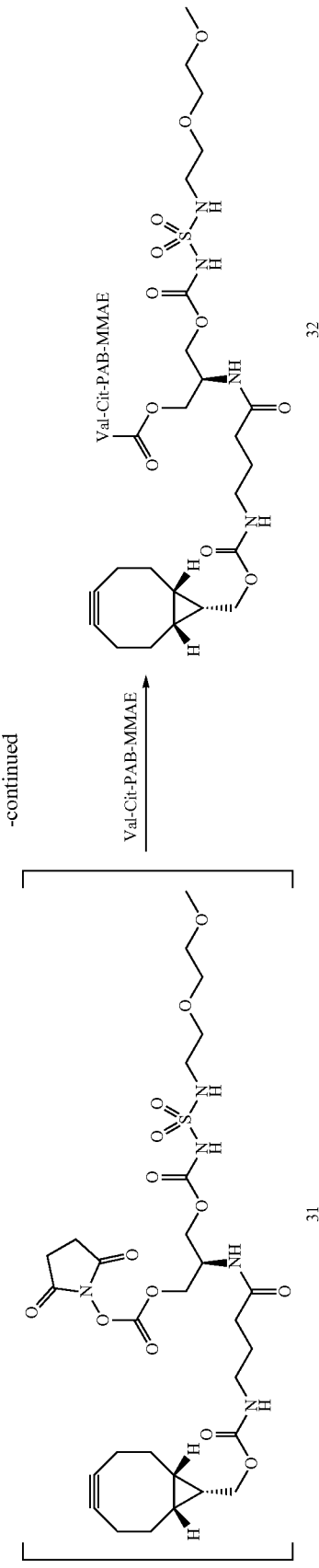
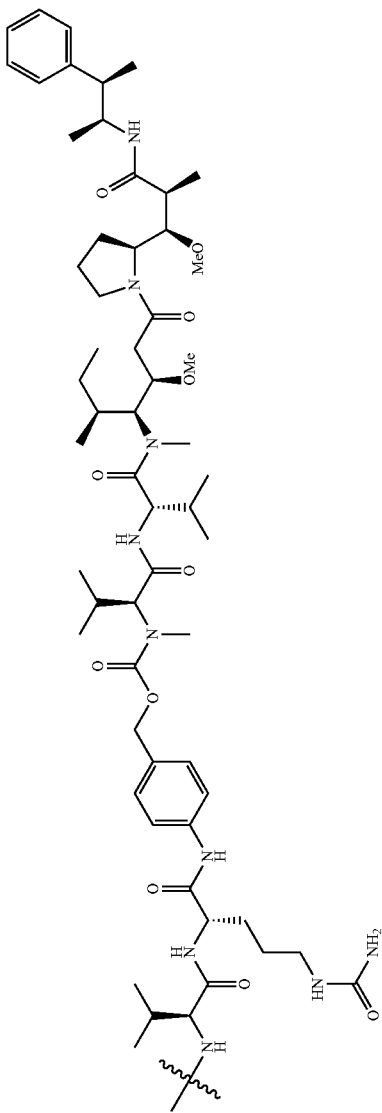

Example 4; Preparation of Compound 27

To a solution of compound 26 (200 mg, 0.65 mmol) in DCM (6.5 mL) under a nitrogen atmosphere was added chlorosulfonyl isocyanate (CSI, 63 µL, 0.72 mmol) and the resulting mixture was stirred for 30 min, when TLC showed consumption of the starting material. Then, Et$_3$N (270 µL, 1.95 mmol) was added followed by 2-(2-methoxyethoxy)ethanamine (83 µL, 0.65 mmol). After 45 min, DCM (15 mL) and sat. NH$_4$Cl solution (10 mL) were added. The layers were separated and the water phase was extracted with EtOAc (3×10 mL). The combined organic layers were dried over sodium sulfate, filtered and concentrated in vacuo. Flash chromatography (20-70% EtOAc in pentane) afforded the product (287 mg, 0.54 mmol, 73%). $^1$H-NMR (400 MHz, CDCl$_3$): δ 6.16 (brs, 1H), 5.04 (d, J=8.8 Hz, 1H), 4.29 (dd, J=11.2, 5.6 Hz, 1H), 4.22-4.15 (m, 1H), 3.95 (brs, 1H), 3.70 (dd, J=10, 3.2 Hz, 1H), 3.65-3.60 (m, 5H), 3.59-3.55 (m, 2H), 3.41 (s, 3H), 3.34 (br s, 2H), 1.45 (s, 9H), 0.89 (s, 9H), 0.06 (s, 6H). LRMS (ESI+) calcd for C$_{20}$H$_{43}$N$_3$O$_9$SSi (M+H$^+$) 530.26, found 530.21.

Example 5: Preparation of Compound 28

To a solution of compound 27 (287 mg, 0.54 mmol) in DCM (4 mL) was added TFA (1 mL) and the reaction mixture was stirred at rt for 1.5 h. The reaction was concentrated and co-evaporated with toluene (2×30 mL) to afford the crude product. LRMS (ESI+) calcd for C$_{15}$H$_{35}$N$_3$O$_7$SSi (M+H$^+$) 430.20, found 430.20.

Example 6: Preparation of Compound 29

To a solution of the crude amine (0.27 mmol) in DCM (2 mL) under a nitrogen atmosphere was added Et$_3$N (149 µL, 1.1 mmol), followed by addition of compound 23 (122 mg, 0.32 mmol) in DCM (1 mL). The resulting solution was stirred at rt overnight and analysed by mass spectrometry. All starting material was consumed, the coupled product and product containing the free alcohol were formed. The reaction mixture was used neat for flash chromatography (50-100% EtOAc in pentane, then 1-10% MeOH in EtOAc) to afford both observed products, OTBDMS derivative 29 (69 mg, 0.09 mmol, 37%) and OH derivative 30 (113 mg, 0.18 mmol, 65%). For 29: $^1$H-NMR (400 MHz, CDCl$_3$): δ 5.1 (br s, 1H), 4.32 (d, J=8.8 Hz, 2H), 4.23-4.11 (m, 3H), 3.70 (dd, J=10.4, 3.2 Hz, 1H), 3.66-3.58 (m, 8H), 3.57-3.51 (m, 2H), 3.40-3.34 (m, 4H), 3.30 (t, J=4.4 Hz, 2H), 3.24-3.18 (m, 2H), 2.34-2.15 (m, 8H), 1.90-1.73 (m, 2H), 1.64-1.50 (m, 2H), 1.42-1.28 (m, 2H), 0.99-0.80 (m, 11H), 0.06 (s, 6H). LRMS (ESI+) calcd for C$_{30}$H$_{54}$N$_4$O$_{10}$SSi (M+H$^+$) 691.34, found 691.35. For 30: LRMS (ESI+) calcd for C$_{24}$H$_{40}$N$_4$O$_{10}$S (M+H$^+$) 577.25, found 577.25.

Example 7: Preparation of Compound 30

To a solution of the protected alcohol 29 (69 mg, 0.099 mmol) in dry THF (1 mL) was added TBAF (120 µL, 1 M solution in THF) under a nitrogen atmosphere. The reaction was stirred at rt and the conversion monitored by mass spectrometry. After 3 h, complete conversion was observed and the reaction was concentrated to afford the crude product. LRMS (ESI+) calcd for C$_{24}$H$_{40}$N$_4$O$_{10}$S (M+H$^+$) 577.25, found 577.25.

Example 8: Preparation of Compound 31

To a solution of compound 30 (55 mg, 0.095 mmol) in DCM/DMF 9/1 (1 mL) were added DSC (20 mg, 0.076 mmol) and Et$_3$N (40 µL, 0.286 mmol). The reaction mixture was stirred at rt and the conversion monitored by mass spectrometry. After 3 h, 100 µL was taken out for the follow-up reaction (coupling to VC-PAB-MMAE). The remaining 900 µL was used neat for flash chromatography (0-10% MeOH in EtOAc) to afford the product (34 mg, 0.047 mmol, 50%). LRMS (ESI+) calcd for C$_{29}$H$_{43}$N$_5$O$_{14}$S (M+H$^+$) 718.26, found 718.35.

Example 9: Preparation of Compound 32

Val-Cit-PABC-MMAE (17 mg, 13 µmol) was dissolved in DMF (500 µL) and Et$_3$N (2.1 µL, 15 µmol) was added. Then, 100 µL of the reaction mixture of the DSC activation containing approx. 5 µmol activated alcohol, was added to the reaction and the mixture was allowed to stand overnight at rt. 2,2'-(ethylenedioxy)bis(ethylamine) (2.2 µL, 15 µmol) was added to quench possible remaining activated reagent. After 2 h, the resulting solution was purified by preparative HPLC (70:30-10:90 H$_2$O:MeCN+1% AcOH) to afford the product (3.8 mg, 2.2 µmol, approx. 44%). LRMS (ESI+) calcd for C$_{83}$H$_{132}$N$_{14}$O$_{23}$S (M+H$^+$) 1727.11, found 1727.09.

Examples 10-14: EndoSH

In one aspect, the invention concerns a fusion enzyme comprising two endoglycosidases. In a particular example the two endoglycosidases EndoS and EndoH are connected via a linker, preferably a -(Gly$_4$Ser)$_3$-(His)$_6$-(Gly$_4$Ser)$_3$-linker. The fusion enzyme according to the invention as also referred to as EndoSH. The enzyme according to the invention has at least 50% sequence identity with SEQ ID NO: 1, preferably at least 70%, more preferably at least 80% sequence identity with SEQ ID NO: 1, such as at least 81%, 82%, 83%, 84%, 85%, 86%, 87%, 88%, 89%, 90%, 91%, 92%, 93%, 94%, 95%, 96%, 97%, 98% or 99% sequence identity with SEQ ID NO: 1. Identity can be readily calculated by known methods and/or computer program methods known in the art such as BLASTP publicly available from NCBI and other sources (BLAST Manual, Altschul, S., et al., NCBI NLM NIH Bethesda, MD 20894; Altschul, S., et al, J. Mol. Biol. 215:403-410 (1990). Preferably, the enzyme of the invention, having the above indicated sequence identity to SEQ ID NO: 1, has EndoS and EndoH activity. Most preferably, the enzyme according to the invention has 100% sequence identity with SEQ ID NO: 1.

Also encompassed are fusion enzymes of EndoS and EndoH, wherein the linker is replaced by another suitable linker known in the art, wherein said linker may be a rigid, or flexible. Preferably, said linker is a flexible linker allowing the adjacent protein domains to move relative freely to one another. Preferably, said flexible linker is composed of amino residues like glycine, serine, histidine and/or alanine and has a length of 3 to 59 amino acid residues, preferably 10 to 45 or 15 to 40 amino acid residues, such as 15, 16, 17, 18, 19, 20, 21, 22, 23, 24, 25, 26, 27, 28, 29, 30, 31, 32, 33, 34, 35, 36, 37, 38, 39 or 40 amino acid residues, or 20 to 38, 25 to 37 or 30 to 36 amino acid residues. Optionally, the fusion enzyme is covalently linked to, or comprises, a tag for ease of purification and or detection as known in the art, such as an Fc-tag, FLAG-tag, poly(His)-tag, HA-tag and Myc-tag.

Trimming of glycoproteins is known in the art, from e.g. WO 2007/133855 or WO 2014/065661. The enzyme according to the invention exhibits both EndoS and EndoH activity, and is capable of trimming glycans on glycoproteins (such as antibodies) at the core GlcNAc unit, leaving only the core GlcNAc residue on the glycoprotein (EndoS activity) as well as well as splitting off high-manose glycans (EndoH activity). Surprisingly, both activities of the fusion enzyme function smoothly at a pH around 7-8, while monomeric EndoH requires a pH of 6 to operate optimally.

The fusion enzyme according to the invention can be prepared by routine techniques in the art, such as introducing an expression vector (e.g. plasmid) comprising the enzyme coding sequence into a host cell (e.g. *E. coli*) for expression, from which the enzyme can be isolated. A possible approach for the preparation and purification of the fusion enzyme according to the invention is given in examples 10-12, and its functioning is demonstrated in examples 13 and 14, wherein trastuzumab and high-mannose trastuzumab are efficiently trimmed in a single step. Another example of the efficient trimming of glycans by the fusion protein EndoSH is provided in example 17.

Example 10: Cloning of Fusion Protein EndoSH into (pET22B) Expression Vector A pET22B-vector containing an EndoS-$(G_4S)_3$-$(His)_6$-$(G_4S)_3$-EndoH (EndoSH) coding sequence (EndoSH being identified by SEQ ID NO: 1) between EcoRI-HindIII sites was obtained from Genscript. The DNA sequence for the EndoSH fusion protein consists of the encoding residues 48-995 of EndoS fused via an N-terminal linked glycine-serine (GS) linker to EndoH. The glycine-serine (GS) linker comprises a -$(G_4S)_3$-$(His)_6$-$(G_4S)_3$— format, allowing spacing of the two enzymes and at the same time introducing a IMAC-purification tag.

Example 11: *E. coli* Expression of Fusion Protein EndoSH

Expression of the EndoSH fusion protein (identified by SEQ ID NO: 1) starts with the transformation of the plasmid (pET22b-EndoSH) into BL21 cells. Next step is the inoculation of 500 mL culture (LB medium+Ampilicin) with BL21 cells. When the OD600 reached 0.7 the cultures were induced with 1 mM IPTG (500 µL of 1M stock solution).

Example 12: Purification of Fusion Protein EndoSH from *E. coli*

After overnight induction at 37° C. the cultures were pelleted by centrifugation. The pellets were resuspended in 40 mL PBS and incubated on ice with 5 ml lysozyme (10 mg/mL) for 30 minutes. After half an hour 5 ml 10% Triton-X-100 was added and sonicated (10 minutes) on ice. After the sonication the cell debris was removed by centrifugation (10 minutes 8000×g) followed by filtration through a 0.22 µM-pore diameter filter. The soluble extract was loaded onto a HisTrap HP 5 mL column (GE Healthcare). The column was first washed with buffer A (20 mM Tris buffer, 20 mM imidazole, 500 mM NaCl, pH 7.5). Retained protein was eluted with buffer B (20 mM Tris, 500 mM NaCl, 250 mM imidazole, pH 7.5, 10 mL). Fractions were analyzed by SDS-PAGE on polyacrylamide gels (12%). The fractions that contained purified target protein were combined and the buffer was exchanged against 20 mM Tris pH 7.5 and 150 mM NaCl by dialysis performed overnight at 4° C. The purified protein was concentrated to at least 2 mg/mL using an Amicon Ultra-0.5, Ultracel-10 Membrane (Millipore). The product is stored at −80° C. prior to further use.

Example 13: Trimming of Trastuzumab by EndoSH

Trastuzumab (obtained from Epirus biopharma (Utrecht, The Netherlands)) in 25 mM Tris buffer pH 8), (14 mg/mL) was trimmed using a concentration of either 0.1 or 1 w/w % EndoSH. The reactions, 350 µg trastuzumab (25 µL) and the appropriate amount of EndoSH, were stirred at 37° C. and analyzed by MS analysis overtime, 1 to 3 hours. Samples were subjected to Fabricator treatment prior to analysis. Full conversions to the trimmed product, which trimmed to the core GlcNAc sugar residue, was observed after 1 hour at 37° C. with 0.1 w/w % EndoSH.

Example 14: Trimming of High-Mannose Trastuzumab by Fusion Protein EndoSH

Trastuzumab having high-mannose glycans (obtained via transient expression in CHO K1 cells in the presence of kifunensine performed by Evitria (Zurich, Switzerland)) (14 mg/mL) in 25 mM Tris buffer pH 8, was trimmed using a concentration of either 0.1 or 1 w/w % EndoSH. The reactions, 350 µg high-mannose trastuzumab (25 µL) and the appropriate amount of EndoSH, were stirred at 37° C. and analyzed by MS analysis over time, 1-3 hours. Samples were subjected to Fabricator treatment prior to analysis. Full conversions to the trimmed product, which trimmed to the core GlcNAc sugar residue, was observed after 3 hours at 37° C. with 1 w/w % EndoSH.

RP-HPLC Analysis of Reduced Monoclonal Antibodies

Prior to RP-HPLC analysis samples were reduced by incubating a solution of 10 µg (modified) IgG for 15 minutes at 37° C. with 10 mM DTT and 100 mM Tris pH 8.0 in a total volume of 50 µL. A solution of 49% ACN, 49% MQ and 2% formic acid (50 µL) was added to the reduced sample. Reverse phase HPLC was performed on a Agilent 1100 HPLC using a ZORBAX Phoroshell 300SB-C8 1×75 5 µm (Agilent Technologies) column run at 1 ml/min at 70° C. using a 16.9 minute linear gradient from 25 to 50% buffer B (with buffer A=90% MQ, 10% ACN, 0.1% TFA and buffer B=90% ACN, 10% MQ, 0.1% TFA).

Mass Spectral Analysis of Monoclonal Antibodies

Prior to mass spectral analysis, IgGs were either treated with DTT, which allows analysis of both light and heavy chain, or treated with Fabricator™ (commercially available from Genovis, Lund, Sweden), which allows analysis of the Fc/2 fragment. For analysis of both light and heavy chain, a solution of 20 µg (modified) IgG was incubated for 5 minutes at 37° C. with 100 mM DTT in a total volume of 4 µL. If present, azide-functionalities are reduced to amines under these conditions. For analysis of the Fc/2 fragment, a solution of 20 µg (modified) IgG was incubated for 1 hour at 37° C. with Fabricator™ (1.25 U/µL) in phosphate-buffered saline (PBS) pH 6.6 in a total volume of 10 µL. After reduction or Fabricator-digestion the samples were washed trice with milliQ using an Amicon Ultra-0.5, Ultra-cel-10 Membrane (Millipore) resulting in a final sample volume of approximately 40 µL. Next, the samples were analyzed by electrospray ionization time-of-flight (ESI-TOF) on a JEOL AccuTOF. Deconvoluted spectra were obtained using Magtran software

Examples 15-19: Preparation of cAC10 Bioconjugate

The preparation of modified biomolecule 13d, is performed according to the procedure as is described below utilizing an endoglycosidase fusion protein EndoS-linker- EndoH (also referred to as EndoSH, identified by SEQ ID NO: 1) for trimming of the glycans of cAC10. In the second step the trimmed cAC10 was converted to the azido-modified mAb 13d through the action of His-TnGalNAcT in the presence of 6-N3-GalNAc-UDP (commercially available from GlycoHub) as a substrate.

Example 15: Transient Expression and Purification of cAC10 cAC10 was transiently expressed in CHO K1 cells by Evitria (Zurich, Switzerland) at 5 L scale. The supernatant was purified using a XK 26/20 column packed with 50 mL protein A sepharose. In a single run 5 L supernatant was loaded onto the column followed by washing with at least 10 column volumes of 25 mM Tris pH 7.5, 150 mM NaCl. Retained protein was eluted with 0.1 M Glycine pH 2.7. The eluted cAC10 was immediately neutralized with 1.5 M Tris-HCl pH 8.8 and dialyzed against 25 mM Tris pH 8.0. Next the IgG was concentrated to approximately 20 mg/mL using a Vivaspin Turbo 15 ultrafiltration unit (Sartorius) and stored at −80° C. prior to further use.

Example 16: Transient Expression and Purification of His-TnGalNAcT(33-421)

His-TnGalNAcT(33-421) (identified by SEQ ID NO: 2) was transiently expressed in CHO K1 cells by Evitria (Zurich, Switzerland) at 5 L scale. The supernatant was purified using a XK 16/20 column packed with 25 mL Ni sepharose excel (GE Healthcare). Each run approximately 1.5 L supernatant was loaded onto the column followed by washing with at least 10 column volumes of buffer A (20 mM Tris buffer, 5 mM imidazole, 500 mM NaCl, pH 7.5). Retained protein was eluted with buffer B (20 mM Tris, 500 mM NaCl, 500 mM imidazole, pH 7.5). The buffer of the eluted fractions was exchanged to 25 mM Tris pH 8.0 using a HiPrep H26/10 desalting column (GE Healthcare). The purified protein was concentrated to at least 3 mg/mL using a Vivaspin Turbo 4 ultrafiltration unit (Sartorius) and stored at −80° C. prior to further use.

Example 17: Preparation of Trimmed cAC10 by Means of Fusion Protein EndoSH

Glycan trimming of cAC10 (obtained via transient expression in CHO K1 cells performed by Evitria (Zurich, Switzerland) was performed with fusion protein EndoSH. Thus, cAC10 (14.5 mg/mL) was incubated with EndoSH (1 w/w %) in 25 mM Tris pH 7.5 with 150 mM NaCl for approximately 16 hours at 37° C. The trimmed IgG was dialyzed against 3×1 L of 25 mM Tris-HCl pH 8.0. Mass spectral analysis of a fabricator-digested sample showed three peaks of the Fc/2-fragment belonging to one major product (observed mass 24105 Da, approximately 80% of total Fc/2 fragment), corresponding to core GlcNAc(Fuc)-substituted cAC10, and two minor products (observed masses of 23959 and 24233 Da, approximately 5 and 15% of total Fc/2 fragment), corresponding to core GlcNAc-substituted cAC10 and core GlcNAc(Fuc)-substituted cAC10 with C-terminal lysine.

Example 18: Glycosyltransfer of the 6-N3-GalNAc-UDP to Trimmed cAC10 Under the Action of TnGalNAcT Substrate 6-N3-GalNAc-UDP (11 d) is used for the preparation of the modified biomolecule cAC10-(6-N3-GalNAc)2 13d, suitable as biomolecule in the context of the invention. Trimmed cAC10 (10 mg/mL), obtained by EndoSH treatment of cAC10 as described above in example 17, was incubated with the substrate 6-N3-GalNAc-UDP (2.5 mM, commercially available from GlycoHub) and 0.5 mg/mL His-TnGalNAcT(33-421) (5 w/w %) in 10 mM MnCl$_2$ and 25 mM Tris-HCl pH 8.0 at 30° C. After 3 hours the amount of His-TnGalNAcT(33-421) was increased to a final concentration of 1 mg/mL (10 w/w %) and the reaction was incubated overnight at 30° C. Biomolecule 13d was purified from the reaction mixture on a HiTrap MabSelect SuRe 5 ml column (GE Healthcare) using an AKTA purifier-10 (GE Healthcare). The eluted IgG was immediately neutralized with 1.5 M Tris-HCl pH 8.8 and dialyzed against PBS pH 7.4. Next the IgG was concentrated using an Amicon Ultra-0.5, Ultracel-10 Membrane (Millipore) to a concentration of 23.38 mg/mL. Mass spectral analysis of a fabricator-digested sample showed three peaks of the Fc/2-fragment belonging to one major product (observed mass 24333 Da, approximately 80% of total Fc/2 fragment), corresponding to core 6-N3-GalNAc-GlcNAc(Fuc)-substituted cAC10, and two minor products (observed masses of 24187 and 24461 Da, approximately 5 and 15% of total Fc/2 fragment), corresponding to core 6-N3-GalNAc-GlcNAc-substituted cAC10 and core 6-N3-GalNAc-GlcNAc(Fuc)-substituted cAC10 with C-terminal lysine.

Example 19: Conjugation of 13d with 32 to Obtain Conjugate 33

The bioconjugate according to the invention was prepared according to the following scheme, by conjugation of compound 32 to modified biomolecule 13d:

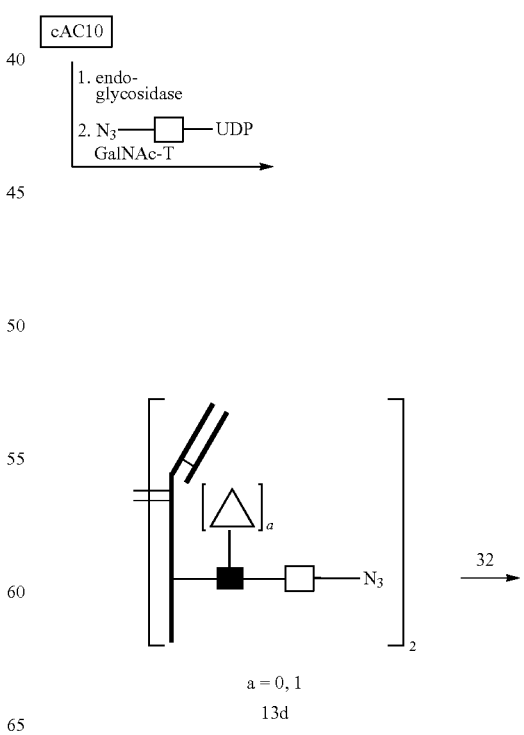

To a solution of cAC(azide)₂ (13d) (287 μL, 6.7 mg, 23.38 mg/ml in PBS pH 7.4) was added compound 32 (90 μL, 10 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 26092 Da, approximately 90% of total Fc/2 fragment), corresponding to the conjugated Fc/2 fragment. RP-HPLC analysis of the reduced sample indicated an average DAR of 1.81.

```
Sequence identification of fusion protein EndoSH (SEQ. ID NO: 1):
   1 MPSIDSLHYL SENSKKEFKE ELSKAGQESQ KVKEILAKAQ QADKQAQELA

51 KMKIPEKIPM KPLHGPLYGG YFRTWHDKTS DPTEKDKVNS MGELPKEVDL

101 AFIFHDWTKD YSLFWKELAT KHVPKLNKQG TRVIRTIPWR FLAGGDNSGI

151 AEDTSKYPNT PEGNKALAKA IVDEYVYKYN LDGLDVDVEH DSIPKVDKKE

201 DTAGVERSIQ VFEEIGKLIG PKGVDKSRLF IMDSTYMADK NPLIERGAPY

251 INLLLVQVYG SQGEKGGWEP VSNRPEKTME ERWQGYSKYI RPEQYMIGFS

301 FYEENAQEGN LWYDINSRKD EDKANGINTD ITGTRAERYA RWQPKTGGVK

351 GGIFSYAIDR DGVAHQPKKY AKQKEFKDAT DNIFHSDYSV SKALKTVMLK

401 DKSYDLIDEK DFPDKALREA VMAQVGTRKG DLERFNGTLR LDNPAIQSLE

451 GLNKFKKLAQ LDLIGLSRIT KLDRSVLPAN MKPGKDTLET VLETYKKDNK

501 EEPATIPPVS LKVSGLTGLK ELDLSGFDRE TLAGLDAATL TSLEKVDISG

551 NKLDLAPGTE NRQIFDTMLS TISNHVGSNE QTVKFDKQKP TGHYPDTYGK

601 TSLRLPVANE KVDLQSQLLF GTVTNQGTLI NSEADYKAYQ NHKIAGRSFV

651 DSNYHYNNFK VSYENYTVKV TDSTLGTTTD KTLATDKEET YKVDFFSPAD

701 KTKAVHTAKV IVGDEKTMMV NLAEGATVIG GSADPVNARK VFDGQLGSET

751 DNISLGWDSK QSIIFKLKED GLIKHWRFFN DSARNPETTN KPIQEASLQI

801 FNIKDYNLDN LLENPNKFDD EKYWITVDTY SAQGERATAF SNTLNNITSK

851 YWRVVFDTKG DRYSSPVVPE LQILGYPLPN ADTIMKTVTT AKELSQQKDK

901 FSQKMLDELK IKEMALETSL NSKIFDVTAI NANAGVLKDC IEKRQLLKKG

951 GGGSGGGGSG GGGSHHHHHH EFGGGGSGGG GSGGGGSAPA PVKQGPTSVA

1001 YVEVNNNSML NVGKYTLADG GGNAFDVAVI FAANINYDTG TKTAYLHFNE

1051 NVQRVLDNAV TQIRPLQQQG IKVLLSVLGN HQGAGFANFP SQQAASAFAK

1101 QLSDAVAKYG LDGVDFDDEY AEYGNNGTAQ PNDSSFVHLV TALRANMPDK

1151 IISLYNIGPA ASRLSYGGVD VSDKFDYAWN PYYGTWQVPG IALPKAQLSP

1201 AAVEIGRTSR STVADLARRT VDEGYGVYLT YNLDGGDRTA DVSAFTRELY

1251 GSEAVRTP
(linker is underlined, EndoH sequence is denoted in italics)
```

-continued

Sequence of His-TnGalNAcT(33-421) (SEQ. ID NO: 2):

```
  1 MGSSHHHHHH SSGLVPRGSH MSPLRTYLYT PLYNATQPTL RNVERLAANW PKKIPSNYIE

61 DSEEYSIKNI SLSNHTTRAS VVHPPSSITE TASKLDKNMT IQDGAFAMIS PTPLLITKLM

121 DSIKSYVTTE DGVKKAEAVV TLPLCDSMPP DLGPITLNKT ELELEWVEKK FPEVEWGGRY

181 SPPNCTARHR VAIIVPYRDR QQHLAIFLNH MHPFLMKQQI EYGIFIVEQE GNKDFNRAKL

241 MNVGFVESQK LVAEGWQCFV FHDIDLLPLD TRNLYSCPRQ PRHMSASIDK LHFKLPYEDI

301 FGGVSAMTLE QFTRVNGFSN KYWGWGGEDD DMSYRLKKIN YHIARYKMSI ARYAMLDHKK

361 STPNPKRYQL LSQTSKTFQK DGLSTLEYEL VQVVQYHLYT HILVNIDERS
```

---

The invention claimed is:

1. A compound comprising a target molecule D covalently connected to a reactive group Q' via a linker represented by the following formula:

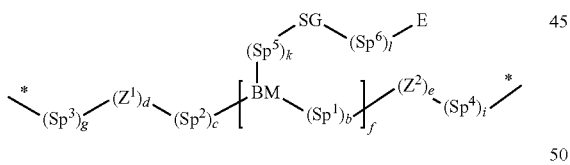

wherein:
BM is a branching moiety;
E is a capping group;
SG is a sulfamide group according to formula (1);
b is independently 0 or 1;
c is 0 or 1;
d is 0 or 1;
e is 0 or 1;
f is an integer in the range of 1 to 10;
g is 0 or 1;
i is 0 or 1;
k is 0 or 1;
l is 0 or 1;
$Sp^1$ is a spacer moiety;
$Sp^2$ is a spacer moiety;
$Sp^3$ is a spacer moiety;
$Sp^4$ is a spacer moiety;
$Sp^5$ is a spacer moiety;
$Sp^6$ is a spacer moiety;
$Z^1$ is a connecting group;
$Z^2$ is a connecting group,
wherein one of the bonds labelled with * is connected to reactive group $Q^1$ and one of the bonds labelled with * is connected to target molecule D, and wherein the sulfamide group SG is represented by formula (1):

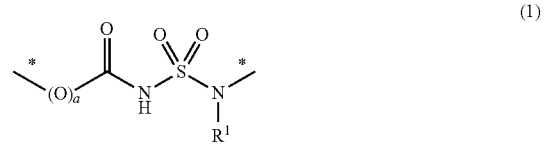

wherein
a is 0 or 1; and
$R^1$ is selected from the group consisting of hydrogen, $C_1$-$C_{24}$ alkyl groups, $C_3$-$C_{24}$ cycloalkyl groups, $C_2$-$C_{24}$ (hetero) aryl groups, $C_3$-$C_{24}$ alkyl (hetero) aryl groups and $C_3$-$C_{24}$ (hetero) arylalkyl groups, wherein the $C_1$-$C_{24}$ alkyl groups, $C_3$-$C_{24}$ cycloalkyl groups, $C_2$-$C_{24}$ (hetero) aryl groups, $C_3$-$C_{24}$ alkyl (hetero) aryl groups and $C_3$-$C_{24}$ (hetero) arylalkyl groups are optionally substituted and optionally interrupted by one or more heteroatoms selected from O, S and NR³ wherein R³ is independently selected from the group consisting of hydrogen and C₁-C₄ alkyl groups, or R¹ is a further target molecule D, wherein the target molecule is optionally connected to N via a spacer moiety, and wherein one of the bonds labelled with * is connected to the branching moiety, optionally via spacer Sp⁵, and the other bond labelled with * to a capping group E, optionally via spacer Sp⁶, and wherein the target molecule D is selected from the group consisting of active substances, reporter molecules, polymers, solid surfaces, hydrogels, nanoparticles, microparticles and biomolecules; and the reactive group Q¹ is selected from the group consisting of, optionally substituted, N-maleimidyl groups, halogenated N-alkylamido groups, sulfonyloxy N-alkylamido groups, ester groups, carbonate groups, sulfonyl halide groups, thiol groups or derivatives thereof, alkenyl groups, alkynyl groups, (hetero)cycloalkynyl groups, bicyclo[6.1.0]non-4-yn-9-yl groups, cycloalkenyl groups, tetrazinyl groups, azido groups, phosphine groups, nitrile oxide groups, nitrone groups, nitrile imine groups, diazo groups, ketone groups, (O-alkyl) hydroxylamino groups, hydrazine groups, halogenated N-maleimidyl groups, 1,1-bis(sulfonylmethyl)methylcarbonyl groups or elimination derivatives thereof, carbonyl halide groups, allenamide groups, 1,2-quinone groups, and triazine groups.

2. The compound according to claim 1, wherein the capping moiety E is selected from hydrogen, C₁-C₂₄ alkyl groups, C₃-C₂₄ cycloalkyl groups, C₂-C₂₄ (hetero) aryl groups, C₃-C₂₄ alkyl (hetero) aryl groups, C₃-C₂₄ (hetero) arylalkyl groups, wherein the C₁-C₂₄ alkyl groups, C₃-C₂₄ cycloalkyl groups, C₂-C₂₄ (hetero) aryl groups, C₃—C₂₄ alkyl (hetero) aryl groups and C₃-C₂₄ (hetero) arylalkyl groups are optionally substituted and optionally interrupted by one or more heteroatoms selected from O, S and NR³ wherein R³ is independently selected from the group consisting of hydrogen and C₁-C₄ alkyl groups, or E is a further target moiety D.

3. The compound according to claim 2, wherein capping moiety E is selected from a polyethylene glycol group represented by —(CH₂CH₂O)ₛCH₃, wherein s is an integer in the range of 1-10, a C₁-C₂₄ alkyl group, C₂-C₂₄ (hetero) aryl group or a C₃-C₂₄ alkyl(hetero)aryl group.

4. The compound according to claim 3, wherein capping moiety E is a polyethylene glycol group represented by —(CH₂CH₂O)ₛCH₃, wherein s is an integer in the range of 2-4, or a benzyl group.

5. The compound according to claim 1, wherein branching moiety BM is selected from a carbon atom, a nitrogen atom, a phosphorus atom, an aromatic ring, a (hetero)cycle or a polycyclic moiety.

6. The compound according to claim 1, wherein Sp⁵, Spa, Sp³ and Sp⁴, if present, are independently selected from the group consisting of linear or branched C₁-C₂₀ alkylene groups, the alkylene groups being optionally substituted and optionally interrupted by one or more heteroatoms selected from the group consisting of O, S and NR³, wherein R³ is independently selected from the group consisting of hydrogen and C₁-C₄ alkyl groups.

7. The compound according to claim 1, wherein Q¹ is according to formula (9a), (9q), (9n), (9o) or (9p):

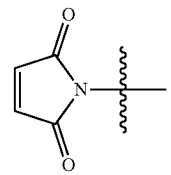
9a

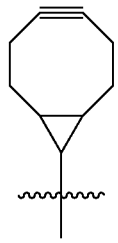
9q

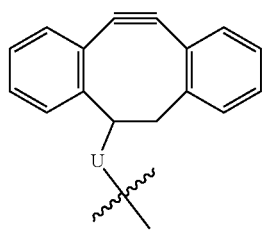
9n

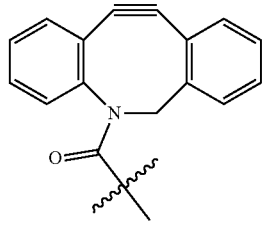
9o

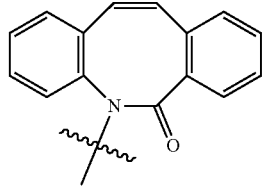
9p wherein U is O or NR⁹, and R⁹ is hydrogen, a linear or branched C₁-C₁₂ alkyl group or a C₄-C₁₂ (hetero)aryl group.

8. The compound according to claim 1, wherein target molecule D is a substance that is biologically and/or pharmaceutically active.

9. A compound comprising a target molecule D covalently connected to a biomolecule B via a linker represented by the following formula:

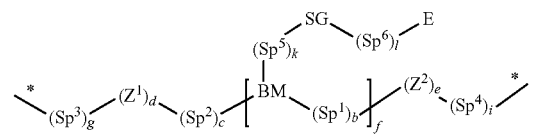

wherein:
BM is a branching moiety;
E is a capping group;
SG is a sulfamide group according to formula (1);

b is independently 0 or 1;
c is 0 or 1;
d is 0 or 1;
e is 0 or 1;
f is an integer in the range of 1 to 10;
g is 0 or 1;
i is 0 or 1;
k is 0 or 1;
l is 0 or 1;
$Sp^1$ is a spacer moiety;
$Sp^2$ is a spacer moiety;
$Sp^3$ is a spacer moiety;
$Sp^4$ is a spacer moiety;
$Sp^5$ is a spacer moiety;
$Sp^6$ is a spacer moiety;
$Z^1$ is a connecting group;
$Z^2$ is a connecting group,
wherein one of the bonds labelled with * is connected to biomolecule B and one of the bonds labelled with * is connected to target molecule D, and wherein the sulfamide group SG is represented by formula (1):

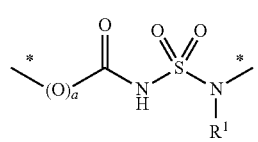

(1)

wherein
a is 0 or 1; and
is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups are optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a further target molecule D, wherein the target molecule is optionally connected to N via a spacer moiety,
and wherein one of the bonds labelled with * is connected to the branching moiety, optionally via spacer Spy, and the other bond labelled with * to a capping group E, optionally via spacer $Sp^6$,
and wherein the biomolecule B is selected from the group consisting of proteins, polypeptides, peptides, glycans, lipids, nucleic acids, oligonucleotides, polysaccharides, oligosaccharides, enzymes, hormones, amino acids and monosaccharides and the target molecule D is selected from the group consisting of active substances, reporter molecules, polymers, solid surfaces, hydrogels, nanoparticles, microparticles and biomolecules.

10. The compound according to claim 9, wherein the capping moiety E is selected from hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups, $C_3$-$C_{24}$ (hetero)arylalkyl groups, wherein the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups are optionally substituted and optionally interrupted by one or more heteroatoms selected from O, S and $NR^3$ wherein $R^3$ is independently selected from the group consisting of hydrogen and $C_1$-$C_4$ alkyl groups, or E is a further target moiety D.

11. The compound according to claim 9, wherein branching moiety BM is selected from a carbon atom, a nitrogen atom, a phosphorus atom, an aromatic ring, a (hetero)cycle or a polycyclic moiety.

12. The compound according to claim 9, wherein biomolecule B is a glycoprotein.

13. The compound according to claim 12, wherein biomolecule B is an antibody.

14. The compound according to claim 9, wherein target molecule D is a substance that is biologically and/or pharmaceutically active.

15. A method for:
(a) improving conjugation efficiency in the preparation of the bioconjugate,
(b) reducing aggregation during the preparation of the bioconjugate and/or of the bioconjugate,
(c) increasing stability of the bioconjugate, and/or
(d) increasing therapeutic index of the bioconjugate,
the method comprising conjugating a biomolecule (B) to a linker represented by the following formula:

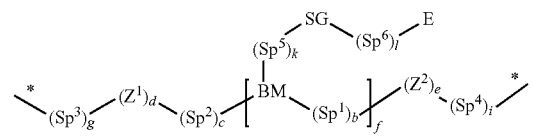

wherein:
BM is a branching moiety;
E is a capping group;
SG is a sulfamide group according to formula (1);
b is independently 0 or 1;
c is 0 or 1;
d is 0 or 1;
e is 0 or 1;
f is an integer in the range of 1 to 10;
g is 0 or 1;
i is 0 or 1;
k is 0 or 1;
l is 0 or 1;
$Sp^1$ is a spacer moiety;
$Sp^2$ is a spacer moiety;
$Sp^3$ is a spacer moiety;
$Sp^4$ is a spacer moiety;
$Sp^5$ is a spacer moiety;
$Sp^6$ is a spacer moiety;
$Z^1$ is a connecting group;
$Z^2$ is a connecting group,
wherein one of the bonds labelled with * is connected to biomolecule B and one of the bonds labelled with * is connected to target molecule D, and wherein the sulfamide group SG is represented by formula (1):

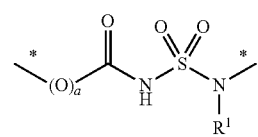

(1)

wherein
a is 0 or 1; and
R$^1$ is selected from the group consisting of hydrogen, C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups, wherein the C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups are optionally substituted and optionally interrupted by one or more heteroatoms selected from O, S and NR$^3$ wherein R$^3$ is independently selected from the group consisting of hydrogen and C$_1$-C$_4$ alkyl groups, or R$^1$ is a further target molecule D, wherein the target molecule is optionally connected to N via a spacer moiety, and wherein one of the bonds labelled with * is connected to the branching moiety, optionally via spacer Sp$^5$, and the other bond labelled with * to a capping group E, optionally via spacer Sp$^6$, and wherein the biomolecule B is selected from the group consisting of proteins, polypeptides, peptides, glycans, lipids, nucleic acids, oligonucleotides, polysaccharides, oligosaccharides, enzymes, hormones, amino acids and monosaccharides and the target molecule D is selected from the group consisting of active substances, reporter molecules, polymers, solid surfaces, hydrogels, nanoparticles, microparticles and biomolecules.

16. A method of treating cancer, the method comprising administering an effective amount of a compound according to claim 9 to a subject in need thereof.

17. The method according to claim 16, wherein the capping moiety E is selected from hydrogen, C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups, C$_3$-C$_{24}$ (hetero)arylalkyl groups, wherein the C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups are optionally substituted and optionally interrupted by one or more heteroatoms selected from O, S and NR$^3$ wherein R$^3$ is independently selected from the group consisting of hydrogen and C$_1$-C$_4$ alkyl groups, or E is a further target moiety D.

18. The method according to claim 16, wherein branching moiety BM is selected from a carbon atom, a nitrogen atom, a phosphorus atom, an aromatic ring, a (hetero)cycle or a polycyclic moiety.

19. The method according to claim 16, wherein target molecule D is a substance that is biologically and/or pharmaceutically active.

20. The method according to claim 16, wherein the compound is an antibody-drug-conjugate.

* * * * *